United States Patent
Langer et al.

(10) Patent No.: US 12,390,537 B2
(45) Date of Patent: Aug. 19, 2025

(54) COMPOSITIONS OF POLYMERIC MICRODEVICES AND METHODS OF USE THEREOF IN CANCER IMMUNOTHERAPY

(71) Applicant: Massachusetts Institute of Technology, Cambridge, MA (US)

(72) Inventors: Robert S. Langer, Cambridge, MA (US); Ana Jaklenec, Cambridge, MA (US); Xueguang Lu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 69 days.

(21) Appl. No.: 17/317,335

(22) Filed: May 11, 2021

(65) Prior Publication Data

US 2021/0354984 A1   Nov. 18, 2021

Related U.S. Application Data

(60) Provisional application No. 63/024,308, filed on May 13, 2020.

(51) Int. Cl.

| | |
|---|---|
| A61K 9/00 | (2006.01) |
| A61K 31/7084 | (2006.01) |
| A61K 31/7088 | (2006.01) |
| A61K 45/06 | (2006.01) |
| A61K 47/69 | (2017.01) |
| A61P 35/00 | (2006.01) |
| B82Y 5/00 | (2011.01) |
| B82Y 40/00 | (2011.01) |
| C07K 16/28 | (2006.01) |

(52) U.S. Cl.
CPC ...... *A61K 47/6937* (2017.08); *A61K 31/7084* (2013.01); *A61K 31/7088* (2013.01); *A61K 45/06* (2013.01); *A61P 35/00* (2018.01); *B82Y 5/00* (2013.01); *B82Y 40/00* (2013.01); *C07K 16/2818* (2013.01); *C07K 16/2827* (2013.01)

(58) Field of Classification Search
CPC .............. A61K 7/6937; A61K 31/7084; A61K 31/7088; A61K 45/06; A61K 9/0021; A61K 9/5031; A61K 9/5084; A61K 9/508; A61K 31/519; A61K 9/0019; A61K 2300/00; A61P 35/00; B82Y 5/00; B82Y 40/00; C07K 16/2818; C07K 16/2827

See application file for complete search history.

(56) References Cited

U.S. PATENT DOCUMENTS

| | | |
|---|---|---|
| 4,450,150 A | 5/1984 | Sidman |
| 6,312,731 B1 | 11/2001 | Staas |
| 6,565,532 B1 | 5/2003 | Yuzhakov |
| 7,411,051 B2 | 8/2008 | Rosen |
| 8,114,845 B2 | 2/2012 | Langermann |
| 9,040,090 B2 | 5/2015 | Desimone |
| 9,045,728 B2 | 6/2015 | Coffey |
| 9,695,212 B2 | 7/2017 | Dubensky, Jr. |
| 10,300,136 B2 | 5/2019 | Jaklenec |
| 10,384,372 B2 | 8/2019 | Vecchione |
| 10,450,341 B2 | 10/2019 | Biggadike |
| 10,478,398 B2 | 11/2019 | Park |
| 10,960,073 B2 | 3/2021 | Jaklenec et al. |
| 11,975,069 B2 | 5/2024 | Jaklenec et al. |
| 2002/0107470 A1 | 8/2002 | Richards |
| 2004/0033241 A1 | 2/2004 | Donovan |
| 2004/0166140 A1 | 8/2004 | Santini et al. |
| 2004/0175410 A1 | 9/2004 | Ashton et al. |
| 2004/0241236 A1 | 12/2004 | Li et al. |
| 2005/0050859 A1 | 3/2005 | Coppeta et al. |
| 2006/0043690 A1 | 3/2006 | Pankau |
| 2006/0099203 A1 | 5/2006 | Pease |
| 2007/0166281 A1 | 7/2007 | Kosak |
| 2008/0026040 A1 | 1/2008 | Farr |
| 2010/0278931 A1 | 11/2010 | Ashton et al. |
| 2011/0129474 A1 | 6/2011 | Shoemaker |
| 2013/0046182 A1 | 2/2013 | Hegg |

(Continued)

FOREIGN PATENT DOCUMENTS

| | | |
|---|---|---|
| CN | 103251941 | 8/2013 |
| JP | 2009035557 | 2/2009 |

(Continued)

OTHER PUBLICATIONS

Lee, Byung Kook, et al. "Fabrication of drug-loaded polymer microparticles with arbitrary geometries using a piezoelectric inkjet printing system." International journal of pharmaceutics 427.2 (2012): 305-310. (Year: 2012).*
Ramazani, Farshad, et al. "Strategies for encapsulation of small hydrophilic and amphiphilic drugs in PLGA microspheres: state-of-the-art and challenges." International journal of pharmaceutics 499.1-2 (2016): 358-367. (Year: 2016).*
Megahed et al., The Interactions between HBV and the Innate Immunity of Hepatocytes. Viruses. Mar. 5, 2020;12(3):285. (Year: 2020).*
Ablasser, et al., "cGAS produces a 2'-5'-linked cyclic dinucleotide second messenger that activates STING", Nature, 498(7454):380-4 (2013).

(Continued)

*Primary Examiner* — Abigail Vanhorn
(74) *Attorney, Agent, or Firm* — Pabst Patent Group LLP

(57) ABSTRACT

Microparticulate compositions and methods for delivery and pulsatile release of one or more sting agonists and/or receptors have been developed. The compositions include polymeric microdevices formed from biodegradable and biocompatible polymers or co-polymers thereof including a shell and compartment(s) or discrete regions in the compartment(s) formed by an additive process such as micromolding, three dimensional printing and lithography. The compositions include microdevices that release individual doses of incorporated STING agonist and/or receptors at defined times, for example, in pulses up to several months after administration with essentially no leakage between releases.

35 Claims, 21 Drawing Sheets

(56) References Cited

U.S. PATENT DOCUMENTS

| | | |
|---|---|---|
| 2013/0204233 A1 | 8/2013 | Zou |
| 2014/0005606 A1 | 1/2014 | Chen |
| 2014/0336487 A1 | 11/2014 | Wang et al. |
| 2015/0165020 A1 | 6/2015 | Jaklenec |
| 2016/0120799 A1 | 5/2016 | Chiang |
| 2016/0136406 A1 | 5/2016 | Berry |
| 2016/0287623 A1 | 10/2016 | Gajewski |
| 2017/0055499 A1 | 3/2017 | Peppou |
| 2017/0157036 A1 | 6/2017 | D'Souza |
| 2018/0296491 A1 | 10/2018 | Delouise |
| 2019/0015650 A1 | 1/2019 | Jaklenec et al. |
| 2019/0076631 A1 | 3/2019 | McHugh et al. |
| 2021/0290921 A1 | 9/2021 | McHugh et al. |
| 2024/0181047 A1* | 6/2024 | Jaklenec ............. A61P 31/00 |

FOREIGN PATENT DOCUMENTS

| | | |
|---|---|---|
| JP | 2012235899 A | 12/2012 |
| RU | 2508135 | 2/2014 |
| WO | 9511010 | 4/1995 |
| WO | 0126708 | 4/2001 |
| WO | 02064162 | 8/2002 |
| WO | 03092633 | 11/2003 |
| WO | 2005071088 | 8/2005 |
| WO | 2007005874 | 1/2007 |
| WO | 2007012114 | 2/2007 |
| WO | 2007027273 | 3/2007 |
| WO | 2007056539 | 5/2007 |
| WO | 2008083174 | 7/2008 |
| WO | 2009014708 | 1/2009 |
| WO | 2009073533 | 6/2009 |
| WO | 2009108689 | 9/2009 |
| WO | 2011156641 | 12/2011 |
| WO | 2013181107 | 12/2013 |
| WO | 2014004301 | 1/2014 |
| WO | 2018119274 | 6/2018 |
| WO | 2019069270 | 4/2019 |
| WO | 2019183578 | 9/2019 |
| WO | 2021136933 | 7/2021 |

OTHER PUBLICATIONS

Alcock, et al., "Long-term thermostabilization of live poxviral and adenoviral vaccine vectors at supraphysiological temperatures in carbohydrate glass", Science Translational Medicine, 2(19):19-19ra12 (2010).

Alieva, et al., "Potential impact of invasive surgical procedures on primary tumor growth and metastasis", Clin. Exp. Metastasis, 35(4):319-331 (2018).

Amini, et al., "Short-Term and Long-Term Effects of Orthopedic Biodegradable Implants", J. Long Term Eff. Med. Implants., 21(2):93-122 (2011).

Amodwala, et al., "Statistically optimized fast dissolving microneedle transdermal patch of meloxicam: A patient friendly approach to manage arthritis", European Journal of Pharmaceutical Sciences, 104:114-123 (2017).

Arthanari, et al., "Preparation and evaluation of sucrose stabilized tetanus toxoid encapsulated into chitosan microspheres", Genomic Medicine, Biomarkers, and Health Sciences, 3:91-97 (2011).

Audran, et al., "Encapsulation of peptides in biodegradable microspheres prolongs their MHC class-I presentation by dendritic cells and macrophages in vitro", Vaccine, 21(11-12):1250-1255 (2003).

Aznar, et al., "Intratumoral Delivery of Immunotherapy—Art Locally, Think Globally", J. Immunol., 198(1):31-39 (2017).

Barber, et al., "STING: infection, inflammation and cancer", Nat. Rev. Immunol., 15(12):760-70 (2015).

Boehm et al., "Modification of microneedles using inkjet printing", AIP Advances, 1:2, 022139 (2011).

Brambilla, et al., Small, John Wiley and Sons, Weinheim An Der Bergstrasse, 12(8):1053-1061 (2016).

Butte, et al., "Programmed Death-1 Ligand 1 Interacts Specifically with the B7-1 Costimulatory Molecule to Inhibit T Cell Responses", Immunity, 27(1):111-122 (2007).

Chen, et al., "Regulation and function of the cGAS-STING pathway of cytosolic DNA sensing", Nat. Immunol., 17(10):1142-9 (2016).

Cheng, et al., "A nanoparticle-incorporated STING activator enhances antitumor immunity in PD-L1-insensitive models of triple-negative breast cancer", JCI Insight, 3(22):120638 (2018).

Claxton, et al., "A systematic review of the associations between dose regimens and medication compliance", Clin. Ther., 23(8):1296-310 (2001).

Cleland, et al., "Development of a single-shot subunit vaccine for HIV-1: Part 4. Optimizing microencapsulation and pulsatile release of MN rgp120 from biodegradable microspheres", Journal of Controlled Release, 47(2): 135-150 (1997).

Cleland, et al., "Single-administration vaccines: controlled-release technology to mimic repeated immunizations", Trends in Biotechnology, 17(1): 25-29 (1999).

Corrales, et al., "Direct Activation of STING in the Tumor Microenvironment Leads to Potent and Systemic Tumor Regression and Immunity", Cell Rep., 11(7):1018-30 (2015).

Corrales, et al., "The host STING pathway at the interface of cancer and immunity", J. Clin. Invest., 126(7):2404-11 (2016).

Cubillos-Ruiz, et al., "Polyethylenimine-based siRNA nanocomplexes reprogram tumor-associated dendritic cells via TLR5 to elicit therapeutic antitumor immunity", J. Clin. Invest., 119(8):2231-2244 (2009).

Curran, et al., "STING Pathway Activation Stimulates Potent Immunity against Acute Myeloid Leukemia", Cell Rep., 15(11):2357-66 (2016).

Demaria, et al., "STING activation of tumor endothelial cells initiates spontaneous and therapeutic antitumor immunity", PNAS, 112(50):15408-13 (2015).

Deng, et al., "STING-Dependent Cytosolic DNA Sensing Promotes Radiation-Induced Type I Interferon-Dependent Antitumor Immunity in Immunogenic Tumors", Immunity, 41(5):843-52 (2014).

Erbe, et al., "Small molecule ligands define a binding site on the immune regulatory protein B7.1", J. Biol. Chem., 277(9):7363-7368 (2002).

Estourgie, et al., "High incidence of in-transit metastases after sentinel node biopsy in patients with melanoma", Br. J. Surg., 91(10):1370-1 (2004).

Farra, et al., "First-in-human testing of a wirelessly controlled drug delivery microchip", Sci. Transl. Med., 4(122):122ra21 (2012).

Freeman, "Structures of PD-1 with its ligands: sideways and dancing cheek to cheek", PNAS, 105(30):10275-10276 (2008).

Fu, et al., "STING agonist formulated cancer vaccines can cure established tumors resistant to PD-1 blockade", Sci. Transl. Med., 7(283):283ra52 (2015).

Gadkaree, et al., "Induction of tumor regression by intratumoral STING agonists combined with anti-programmed death-L1 blocking antibody in a preclinical squamous cell carcinoma model", Head & Neck, 39(6):1086-94 (2017).

Gajewski, et al., "Cancer immunotherapy strategies based on overcoming barriers within the tumor microenvironment", Curr. Opin. Immunol., 25(2):268-76 (2013).

Galon, et al., "Cancer classification using the Immunoscore: a worldwide task force", J. Transl. Med., 10:205 (2012).

Haithcox, et al., "The impact of frequent injections for hematopoietic growth factor support on patients receiving chemotherapy: an observational study", BMC Nurs., 2(1):2 (2003).

Han, et al., "Evaluation of 3 clinical dendritic cell maturation protocols containing lipopolysaccharide and interferon-gamma", J. Immunother., 32(4):399-407 (2009).

Hansen, et al., "Manipulation of the primary breast tumor and the incidence of sentinel node metastases from invasive breast cancer", Arch Surg., 139(6):634-9 (2004).

Harlin, et al., "Chemokine expression in melanoma metastases associated with CD8+ T-cell recruitment", Cancer Res., 69(7):3077-85 (2009).

He, et al., "STING signaling in tumorigenesis and cancer therapy: A friend or foe?", Cancer Lett., 402:203-12 (2017).

(56) References Cited

OTHER PUBLICATIONS

Hobson, et al., "Acute inflammation induced by the biopsy of mouse mammary tumors promotes the development of metastasis", Breast Cancer Res. Treat., 139(2):391-401 (2013).
International Search Report for PCT/US2021/031675 dated Sep. 15, 2021.
Iwasaki, et al., "Control of adaptive immunity by the innate immune system", Nat. Immunol., 16(4):343-53 (2015).
Jaklenec, et al., "Sequential release of bioactive IGF-I and TGF-beta1 from PLGA microsphere-based scaffolds", Biomaterials, 29(10):1518-1525 (2007).
Johansen, et al., "Improving Stability and Release Kinetics of Microencapsulated Tetanus Toxoid by Co-Encapsulation of Additives", Pharmaceutical Research, 15(7):1103-1110 (1998).
Junkins, et al., "A robust microparticle platform for a STING-targeted adjuvant that enhances both humoral and cellular immunity during vaccination", J. Control. Release, 270:1-13 (2018).
Kamaly, et al., "Degradable Controlled-Release Polymers and Polymeric Nanoparticles: Mechanisms of Controlling Drug Release", Chem. Rev., 116(4):2602-63(2016).
Kato, et al., "Structural insights into cGAMP degradation by Ectonucleotide pyrophosphatase phosphodiesterase 1", Nat. Commun., 9(1):4424(2018).
Koshy, et al., "Liposomal Delivery Enhances Immune Activation by STING Agonists for Cancer Immunotherapy", Adv. Biosyst., 1(1-2):1600013 (2017).
Luo, et al., "A STING-activating nanovaccine for cancer immunotherapy", Nat. Nanotechnol., 12(7):648-654 (2017).
Makadia, et al., "Poly Lactic-co-Glycolic Acid (PLGA) as Biodegradable Controlled Drug Delivery Carrier", Polymers (Basel)., 3(3):1377-1397 (2011).
Marcus, et al., "Tumor-Derived cGAMP Triggers a STING-Mediated Interferon Response in Non-tumor Cells to Activate the NK Cell Response", Immunity, 49(4):754-763.e4 (2018).
Mathes, et al., "Adherence influencing factors in patients taking oral anticancer agents: a systematic review", Cancer Epidemiol., 38(3):214-26 (2014).
McHugh, et al., "Fabrication of fillable microparticles and other complex 3D microstructures", Science, 357(6356):1138-1142 (2017).
Molnar, et al., "Crystal structure of the complex between programmed death-1 (PD-1) and its ligand PD-L2", PNAS, 105(30):10483-10488 (2008).
Murillo, et al., "Influence of the co-encapsulation of different excipients on the properties of polyester microparticle-based vaccine against brucellosis", International Journal of Pharmaceutics, 271(1-2):125-135 (2004).
Nandedkar, "Nanovaccines: recent developments in vaccination", J Biosci, 34(6):995-1003 (2009).
Nuxoll, et al., "BioMEMS in drug delivery", Advanced Drug Delivery Reviews, 65(11):1611-1625 (2013).
Ohkuri, et al., "Intratumoral administration of cGAMP transiently accumulates potent macrophages for anti-tumor immunity at a mouse tumor site", Cancer Immunol. Immunother., 66(6):705-716 (2017).
Osterberg, et al., "Adherence to medication", N. Engl. J. Med., 353(5):487-97 (2005).
Park, et al., "Polymer particle-based micromolding to fabricate novel microstructures", Biomed. Microdevices, 9(2):223-234 (2007).
Postow, et al., "Immune Checkpoint Blockade in Cancer Therapy", J. Clin. Oncol., 33(17):1974-82 (2015).
Puts, et al., "An update on a systematic review of the use of geriatric assessment for older adults in oncology", Ann. Oncol., 25(2):307-15 (2014).
Ramanjulu, et al., "Design of amidobenzimidazole STING receptor agonists with systemic activity", Nature, 564(7736):439-443 (2018).
Rudqvist, et al., "Radiotherapy and CTLA-4 Blockade Shape the TCR Repertoire of Tumor-Infiltrating T Cells", Cancer Immunol. Res., 6(2):139-150 (2018).
Sammartino, et al., "Anti-GBM disease following CTLA4 blockade in a patient with metastatic melanoma", Clinical Kidney Journal, 3(2):135-137 (2010).
Sanchez, et al., "Pulsed controlled-released system for potential use in vaccine delivery", J Pharm Sci., 85(6):547-52 (1996).
Shae, et al., "Endosomolytic polymersomes increase the activity of cyclic dinucleotide STING agonists to enhance cancer immunotherapy", Nat. Nanotechnol., 14(3):269-278 (2019).
Shahani, et al., "Highly loaded, sustained-release microparticles of curcumin for chemoprevention", J. Pharm. Sci., 100(7):2599-609 (2011).
Sharma, et al., "The future of immune checkpoint therapy", Science, 348(6230):56-61 (2015).
Sivick, et al., "Magnitude of Therapeutic STING Activation Determines CD8+ T Cell-Mediated Anti-tumor Immunity", Cell Rep., 25(11):3074-3085.e5 (2018).
Takada, et al., "Soluble micro needle array tip for delivering e.g. ophthalmic diagnostic fluorescein into human skin, performs attachments of skin on substrate, where target substance eluted from array is absorbed through perforation", Database WPI section Ch, week 201281 Thomson Scientific, London, GB, Class A96, an 2012-Q82066,XP002785753 (2017).
Tan, et al., "Impact of adherence to disease-modifying therapies on clinical and economic outcomes among patients with multiple sclerosis", Adv. Ther., 28(1):51-61 (2011).
Vatner, et al., "STING, DCs and the link between innate and adaptive tumor immunity", Mol. Immunol., 110:13-23 (2019).
Wang, et al., "cGAS is essential for the antitumor effect of immune checkpoint blockade", PNAS, 114(7):1637-1642 (2017).
Wang, et al., "Quantum anomalous Hall effect in intrinsic magnetic topological insulator MnBi2Te4", Science, 367(6480):895-900 (2020).
Woo, et al., "STING-dependent cytosolic DNA sensing mediates innate immune recognition of immunogenic tumors", Immunity, 41(5):830-42 (2014).
Xia, et al., "Recurrent Loss of STING Signaling in Melanoma Correlates with Susceptibility to Viral Oncolysis", Cancer Res. 76(22):6747-59 (2016).
Yeo, et al., "Control of encapsulation efficiency and initial burst in polymeric microparticle systems", Arch. Pharm. Res., 27(1):1-12 (2004).
Huang, et al., "Levofloxacin implants with predefined microstrucutre fabricated by three-dimensional printing technique", Int. J. of Pharm., 339:33-38 (2007).
International Search Report received for PCT Patent Application No. PCT/US2018/042322, mailed on Nov. 7, 2018, 5 pages.
Jang, et al., "Influence of fluid physical properties on ink-jet printability", Langmuir, 25:2629-2635 (2009).
CASTEM, "CASTEM ultra-fine 3D modeling service", CASTEM Co., Ltd. Tokyo Branch. Available at <https://www.castem.co.jp/frontend/download/file/bisai_3d.pdf?epository=page&saved_as=d63a0ab0a637829a75a894a13701c618.pdf&name=bisai_3d.pdf>, Sep. 19, 2024, 2 pages (Japanese Copy Only).

* cited by examiner

FIG. 5B  FIG. 5C

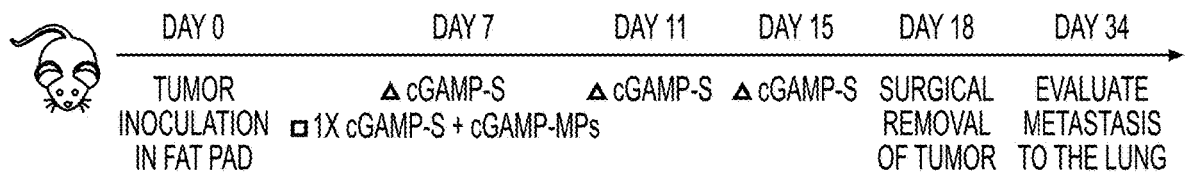
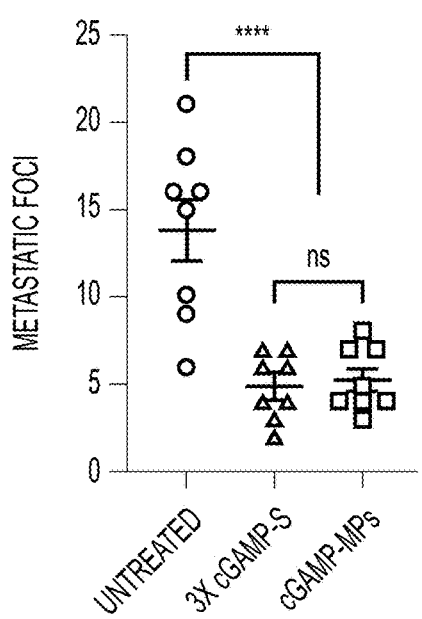
FIG. 5G
FIG. 5H
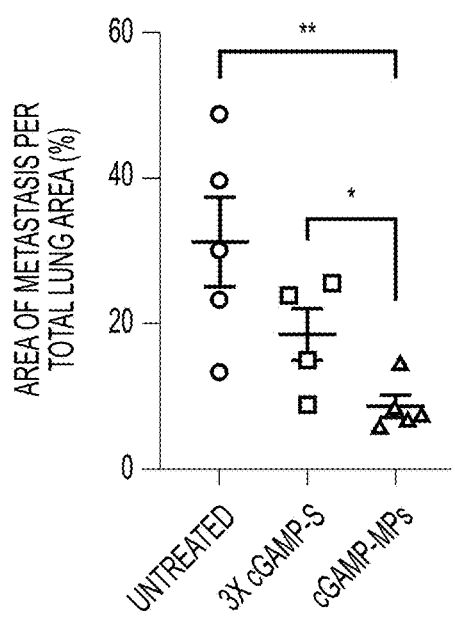
FIG. 5I

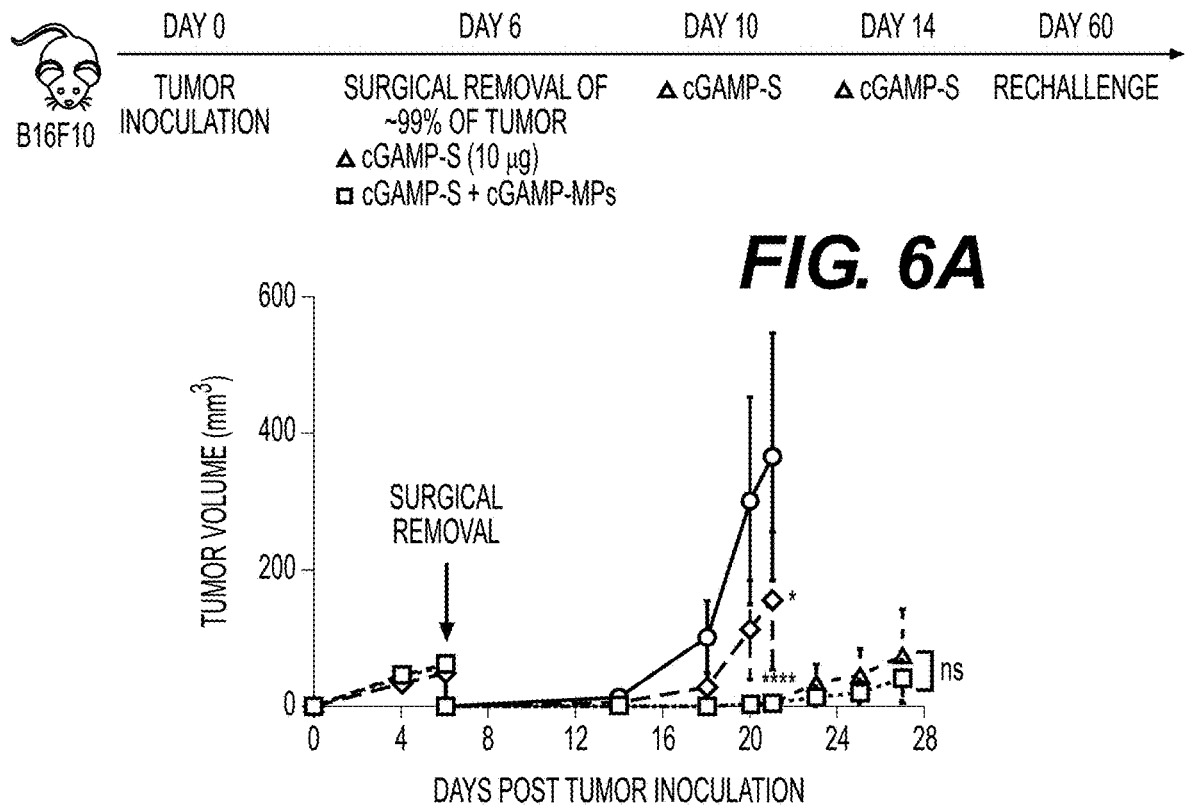
FIG. 6A
FIG. 6B
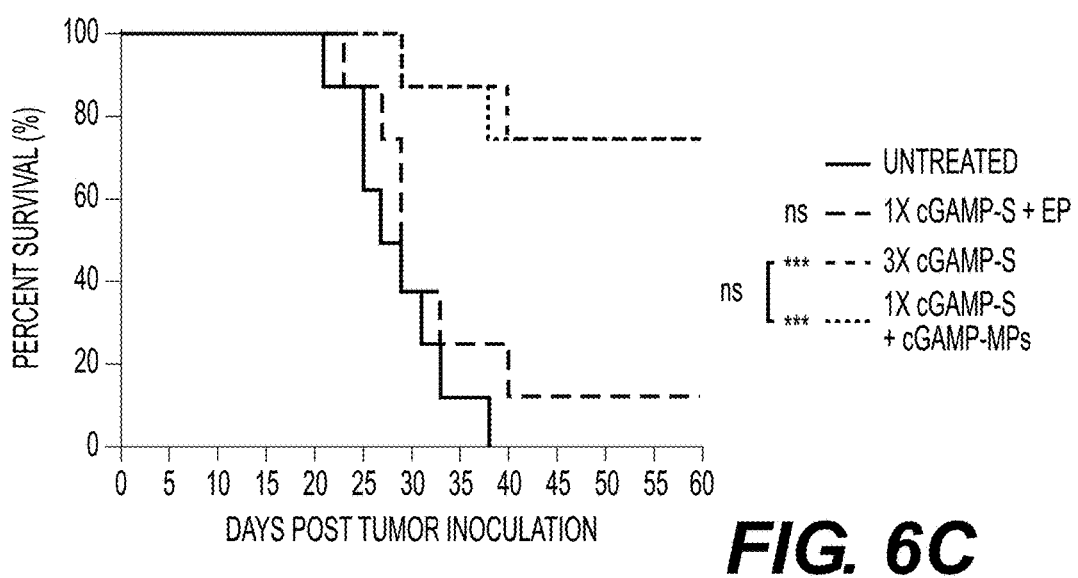
FIG. 6C

COMPOSITIONS OF POLYMERIC MICRODEVICES AND METHODS OF USE THEREOF IN CANCER IMMUNOTHERAPY

CROSS REFERENCE TO RELATED APPLICATIONS

This application claims priority to and benefit of U.S. Provisional Application No. 63/024,308 filed on May 13, 2020, the disclosure of which is hereby incorporated herein by reference in its entirety.

FIELD OF THE INVENTION

The invention is generally directed to compositions for delivery of therapeutic agents over a sustained period of time, and methods of use thereof, particularly in cancer therapy.

BACKGROUND OF THE INVENTION

The advent of immune checkpoint blockade therapy (ICBT) has had a profound impact on cancer treatment, with several drugs receiving approval from the United States Food and Drug Administration (FDA) (Postow M A., et al., *J Clin Oncol.*, 33(17):1974-82 (2015)). Despite significant promise, the clinical benefits of ICBT remain limited by a low response rate (Sharma P. and Allison J P., *Science*, 348:56-51 (2015)). Clinical studies have shown that patients who respond to ICBT have higher levels of tumor-infiltrating lymphocytes (TILs) and display a signature of type I interferon (IFN) producing genes indicative of innate immune system activation (Harlin H., et al., *Cancer Res.*, 69(7):3077-85 (2009); Gajewski T F., et al., *Curr Opin Immunol.*, 25(2):268-76 (2013); and Galon J., et al., *J Transl Med.*, 10:205 (2012). Strategies to improve TILs infiltration and innate immune system activation have been proposed as combination therapies to further improve the response rate of ICBT.

Among many innate immune pathways that are initiated through toll-like receptors (TLRs), mitochondrial antiviral-signaling protein (MAVS), or P2X purinergic receptor 7, activation of stimulator of interferon genes (STING) shows great promise for increasing TILs and improving the antitumor efficacy of ICBT (Wang H., et al., *Proc Natl Acad Sci USA*, 114(7):1637-1642 (2017); Corrales L., et al., *Cell Rep.*, 11(7):1018-30 (2015)). STING pathway activation is initiated through recognition of cytoplasmic DNA. Cyclic guanosine monophosphate-adenosine monophosphate (cGAMP) synthase senses cytoplasmic DNA and produces the second messenger cGAMP, which then binds to STING to trigger a signaling cascade through tank-binding kinase 1 (TBK1)/interferon regulatory factor 3 (IRF3) for production of type I IFNs and other cytokines (Chen Q., et al., Nat Immunol., 17(10):1142-9 (2016); Ablasser A., et al., *Nature*, 498(7454):380-4 (2013)). Substantial evidence has shown that intratumoral injections of a STING agonist stimulate potent antitumor immunity in clinically relevant tumor models (Corrales L., et al., 2015; Shae D. et al., *Nat Nanotechnol.*, 14(3):269-278 (2019); Fu J., et al., *Sci Transl Med.*, 7(283):283ra52 (2015); Curran E., et al., *Cell Rep.*, 15(11): 2357-66 (2016); and Luo M. et al., *Nat Nanotechnol.*, 12(7):648-654 (2017)). As a result, phase I clinical trials using STING agonist alone or in combination with ICBT are under investigation to treat patients with advanced solid tumors and lymphoma.

The dosing regimen of STING agonist in current clinical trials involves multiple intratumoral injections administered repeatedly (e.g., three injections over a 28-day period or one injection every week for 9 weeks per treatment cycle) for as long as two years to achieve therapeutic efficacy (see, e.g., Clinical Trial Identifier Nos.: NCT03010176 and NCT02675439 at http://www.clinicaltrials.gov). Such high dosing frequency over a long period of time can cause chronic injection pain, increase the risk of infection, and ultimately lead to poor adherence, especially when every dose requires a health care visit (Mathes T., et al, *Cancer Epidemiol.*, 38(3):214-26 (2014); Claxton A J., et al., *Clin Ther.*, 23(8):1296-310 (2001); and Puts M T., et al., *Ann Oncol.*, 25(2):307-15 (2014)). The adherence rates to cancer treatment are as low as ~52%, with similar levels (~50%) reported for patients with other chronic diseases (Osterberg L and Blaschke T, *N Engl J Med.*, 353(5):487-97 (2005); Puts M T., et al., *Ann Oncol.*, 25(3):564-77 (2014)). Poor adherence can lead to failed treatment and constitutes a financial burden of approximately $100 billion each year in the United States alone (Tan H., et al., *Adv Ther.*, 28(1):51-61 (2011)). In addition, multiple intratumoral injections also limit the scope of STING agonist-based therapies to readily accessible tumor types and introduce the risk of disrupting the tumor microenvironment (TME) and vascular network, potentially leading to cancer cell extravasation and metastases (Hobson J., et al., *Breast Cancer Res Treat.*, 139(2): 391-401 (2013); Hansen N M., et al., *Arch Surg.*, 139(6): 634-9 (2004); and Estourgie S H., et al., *Br J Surg.*, 91(10):1370-1 (2004)). Therefore, a delivery system that mimics current clinical dosage regimens within a single injection is an attractive solution to improve patient adherence, decrease risk of metastasis and therapeutic cost, and expand the scope of current STING agonist-based therapies.

There remains a need for drug delivery systems that improve patient compliance/adherence, minimize the number of injections a patient is subjected to, decrease risk of metastasis and therapeutic cost, and expand the scope of current STING agonist-based therapies to poorly accessible tumors.

It is therefore an object of the present invention to provide a drug delivery system that simplifies multiple injection dosage regimens.

It is a still further object of the present invention to provide compositions and methods for cancer therapy, particularly immunotherapy.

SUMMARY OF THE INVENTION

Compositions and methods for delivery and pulsatile release of one or more therapeutic and/or prophylactic agents to a site (e.g., tumor) are provided. The compositions typically include microfabricated particles ("microdevices") that remain at the site of injection and release incorporated therapeutic(s) as a programmable sequence of pulses at pre-determined time points that mimic multiple injections over days to weeks.

In preferred embodiments, the therapeutic agent stimulates an immune response, preferably an immune receptor binding agent, such as a STING agonist, and the release profile is designed to mimic repeated single dose administrations of the agent over a sustained period of time. Results show that a single intratumoral injection of such microdevices, loaded with a STING agonist, can trigger potent local and systemic antitumor immune responses, inhibit tumor growth and metastasis, and prolong survival as effectively as multiple doses of the soluble STING agonist.

The microdevices have a biocompatible, biodegradable polymeric shell and a compartment encapsulating a therapeutic agent such as a STING agonist. The shell can be formed of a biodegradable biocompatible polymer or co-polymer such as poly(lactic acid), poly(glycolic acid), and copolymers thereof. In some embodiments, the polymer is poly(lactic-co-glycolic acid) (PLGA). The microdevices can be formed by micromolding, 3D-printing or stereolithography the polymer, which can be used to form the microdevice into complex three-dimensional geometries.

The microdevices can have different shapes. For example, the microdevices can be box-shaped, such as a rectangular prism or cube. In some embodiments, the microdevices have at least one external dimension of between about 1 µm and 1000 µm, and/or the internal compartment has at least one dimension of between about 1 µm and 800 µm. In specific exemplary embodiments, sealed microdevices have external dimensions of 400×400×300 µm (length×width×height) and wall thickness of 100 µm in each dimension, optionally with an internal cavity of 200×200×100 µm (length×width×height), though as discussed in more detail below, alternative external and internal cavity dimensions are also provided.

The therapeutic agent, for example, a STING agonist, can be released from the microdevices in a defined time period in vitro or in vivo such as, about 1 day, about 4 days, about 8 days, about 11 days, about 15 days, about 18 days, about 97 days, about 1 month, about 2 months, about 3 months, about 4 months, about 5 months, about 6 months, or about 1 year. In particular embodiments, the rate of release of the STING agonist is controlled by number-averaged molecular weight of the polymer or co-polymer, weight-averaged molecular weight of the polymer or co-polymer, polydispersity index of the polymer or co-polymer, chain end functionality of the polymer or co-polymer, the ratio of co-polymers, the blending ratio of salts, polymer or co-polymer, thickness of the shell, and compartment matrix, or a combination thereof, as well as loading, and inclusion of excipients, if any.

In a preferred embodiment, the therapeutic agent is a STING agonist, which can be a nucleic acid or a small molecule. Preferably, the STING agonist is a cyclic dinucleotide or non-cyclic dinucleotide. Exemplary STING agonists include cGAMP, DMXAA, MK-1454, MK-2118, E7766, MIW815 (ADU-S100), BMS-986301, GSK3745417, IMSA-101, SYNB18911, SITX-799, and SB 11285.

Populations of microdevices can contain a homogeneous plurality of a microdevices and pharmaceutical compositions thereof. In some embodiments, a pharmaceutical composition includes two or more populations of microdevices and a pharmaceutically acceptable buffer, carrier, diluent or excipient. Each of the different populations of microdevices can release the incorporated agent or agents, preferably a STING agonist, in a time period distinct from the other population(s) in the pharmaceutical composition leading to a pulsatile release of the incorporated agent or agents over a sustained period.

The microdevices and compositions thereof can be used in a variety of methods. For example, a method of delivering one or more agents, particularly, STING agonists, to a subject can include administering to the subject a microdevice, or population, or pharmaceutical composition including two, three, four, or more populations of microdevices thereof. These may contain different therapeutic, prophylactic and/or diagnostic agents, or combinations thereof, or ratios thereof, and release at different or the same times.

Also provided are methods of inducing or modulating an immune response and/or an inflammatory response in a subject comprising. Typically, such methods involve administering to the subject a pharmaceutical composition preferably including two, three, four, or more populations of microdevices, in an effective amount to induce the immune response and/or inflammatory response, preferably over a sustained period of time, most preferably to a tumor when the microdevices are injected into the tumor.

Methods of treating a disease or disorder for other types of cancer are also described. A method of treating cancer in a subject in need thereof can include administering to the subject an effective amount of any of the pharmaceutical compositions to treat the cancer. In such methods, the therapeutic agent (e.g., an immune response stimulating therapeutic agent such as a STING agonist) is preferably released from the microdevices in a pulsatile manner in defined time periods post administration.

In a preferred embodiment, the pharmaceutical composition being administered contains two or more distinct populations of microdevices. For example, the composition can have three distinct populations of microdevices, wherein a first population releases the incorporated STING agonist in about 4 days post administration, a second population releases the incorporated STING agonist in about 8 days post administration, and a third population releases the incorporated STING agonist in about 11 days post administration. Alternative pulsatile release profiles are also provided, and can be achieved by, for example, tuning the number-averaged molecular weight of the polymer or co-polymer, weight-averaged molecular weight of the polymer or co-polymer, polydispersity index of the polymer or co-polymer, chain end functionality of the polymer or co-polymer, the ratio of co-polymers, the blending ratio of salts, polymer or co-polymer, thickness of the shell, and compartment matrix, or a combination thereof. The distinct populations of microdevices can contain the same or different STING agonist.

Generally, the compositions are administered (e.g., locally) in an effective amount to induce a local or systemic immune response and/or inflammatory response, to induce or increase STING pathway activity, to induce or increase an interferon response, to induce infiltration into the tumor microenvironment (e.g., by lymphocytes, basophils, macrophages, and/or dendritic cells), and/or to reduce immunosuppression within the tumor microenvironment. Such effects or responses to administration can last for variable periods of time, including, for about 1 day to about 30 days, about 21 days to about 28 days, about 1 week to about 4 weeks, about 1 month to about 6 months, or about 6 months to about 1 year post administration.

Administration of the microdevice compositions can also reduce or prevent tumor recurrence and/or metastasis.

In some embodiments, particularly those where the subject suffers from cancer, the composition is administered intratumorally. The composition can be administered as a single injection.

The methods of treatment can include further administering an additional cancer therapy to the subject, such as, but not limited to, surgery, radiotherapy, chemotherapy, immunotherapy, cryotherapy or gene therapy. For example, the subject can be further administered one or more STING agonists, one or more immune-checkpoint blockage agents, or a combination thereof. Immune-checkpoint blockage agents can include an antibody or antigen-binding fragment thereof. Suitable antibodies or antigen-binding fragments thereof preferably include inhibitors of CTLA-4, PD-1, PD-L1, PD-L2, TIM-3, LAGS, or a combination thereof.

In some embodiments, the subject has a cancer such as melanoma, cervical cancer, breast cancer, ovarian cancer, prostate cancer, pancreatic cancer, kidney cancer, liver cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, hepatocellular cancer, malignant mesothelioma, leukemia, lymphoma, multiple myeloma, transitional cell carcinoma, neuroblastoma, plasma cell neoplasms, Wilm's tumor, astrocytoma, ependymoma, glioma, meningioma, medulloblastoma, neuroblastoma, or hepatocellular carcinoma. In some embodiments, the cancer is a solid tumor(s) or is lymphoma.

The compositions and methods for pulsatile release over a sustained period of time are believed to be particularly advantageous for treating hard-to-reach tumors with a single dose, particularly where a practitioner would struggle using a conventional method of administering multiple doses of agent to the same region to achieve the same sustained therapy over the desired therapeutic time period.

BRIEF DESCRIPTION OF THE DRAWINGS

FIG. 1A is a schematic of the single injection drug delivery platform for cancer immunotherapy. Different PLGA microdevices reside in the tumor after a single intratumoral injection, release incorporated STING agonist in pulses at discrete time points, and promote infiltration of tumor-infiltrating lymphocytes (TILs). FIG. 1B is a schematic representation of the fabrication process of PLGA microdevices, prepared by filling cargo of interest into microdevice bases and then sealing the base with corresponding microdevice caps by briefly applying heat. FIGS. 1C-1D are representative SEM images of empty microdevice bases (FIG. 1C) and sealed microdevices (FIG. 1D). FIG. 1E is a representative high resolution X-ray computed tomography image of sealed microdevice encapsulating 3'3'-cGAMP. Red color represents dried 3'3'-cGAMP.

FIGS. 2A-2G are graphs showing cumulative in vitro release kinetics of AF647-dextran from PLGA microdevices, PLGA-1 through PLGA-7, respectively. (n=6 to 8). Data represent average±s.e.m. FIGS. 2H-2I are graphs showing cumulative in vitro release kinetics of pemetrexed (FIG. 2H) and Cy5-labeled CpG DNA (FIG. 2I) from PLGA-2 (n=6 to 10). Data represent average±s.e.m. FIGS. 2J-2K are graphs showing cumulative in vitro (FIG. 2J) and in vivo (FIG. 2K) release kinetics of AF647-dextran from PLGA-1, 2, and 3. PLGA-MPs were administered subcutaneously. (n=6-8). Error bars represent standard error of the mean (s.e.m.). FIG. 2L is a graph showing cumulative in vivo release kinetics of AF647-dextran-loaded PLGA-2 that were administered subcutaneously (n=8) or intratumorally in B16F10 melanoma model (n=4) and 4T1 breast cancer model (n=4). Error bars represent s.e.m.

FIG. 4A is a schematic showing the treatment scheme of B16F10 tumor-bearing mice receiving a single injection of cGAMP-S, cGAMP-loaded PLGA-1 and 2 at day 7 or three injections of soluble 3'3'-cGAMP at day 7, 11, and 15 after tumor inoculation. Tumors were isolated on day 16. FIGS. 4B-4C are bar graphs showing qPCR analysis of CXCL10 (FIG. 4B) and IRF7 (FIG. 4C) mRNA expression in tumors (n=4). Data represents mean±s.e.m. FIGS. 4D-4G are bar graphs showing the percentage of infiltrating lymphocytes including CD8+CD3+ T cells (FIG. 4D), CD4+CD3+ T cells (FIG. 4E), and NK1.1+CD3-NK cells (FIG. 4F), and CD11b-CD11c+ dendritic cells, and myeloid cells including CD11b+F4/80+macrophages, CDA-4I11b+F4/80-Ly6c+Ly6g+neutrophils, CD11b+F4/80-Ly6c+Ly6g-monocytes, CD11b+Gr-1-CD200R3+basophils, and CD11b+Gr-1-CD170+eosinophils (FIG. 4G) in TME among all live cells (n=4 to 5). Data represent mean±standard deviation (s.d.). FIG. 4H is a representative flow cytometry histogram of DCs (CD86+CD11c+CD11b-) in tumors treated with different groups (n=4 to 5). Quantitative analysis is shown in the bar graph on the right. Data represent average±s.d. FIG. 4I shows representative flow cytometry histograms of M1 (CD86+CD11b+F4/80+) and M2 (CD206+CD11b+F4/80+) macrophages in tumors treated with different groups. The ratio of M1/M2 macrophages was calculated and presented on the right (n=4). Data represent average±s.d. Statistical significance was calculated by one-way ANOVA or Student's T test when comparing multiple or two groups. Data were compared with untreated group if there is no specific indication. $*P<0.05$, $P<0.01$, $*P<0.001$, $****P<0.0001$.

FIGS. 5B-5C are bar graphs showing the number of effective memory CL62L-CD44+CD4+CD3+ T cells (FIG. 5B) and CL62L-CD44+CD8+CD3+ T cells (FIG. 5C) in the TME at day 16 (treatment scheme shown in FIG. 4A). FIG. 5G is a schematic of treatment regimen on a metastatic 4T1 model. FIG. 5H is a graph showing the number of metastatic foci on lung surfaces after treatments (n=8). FIG. 5I is a graph showing the percentage of tumor area within total lung area after treatments (n=4 to 5). Statistical significance was calculated by t-test and two-way ANOVA: *$P<0.05$, $P<0.01$, *$P<0.001$, ****$P<0.0001$.

FIGS. 6A-6H demonstrate that a single injection of PLGA-MPs induces systemic antitumor immunity and inhibits metastasis. FIG. 6A is a schematic representation of the treatment regimen in a surgical removal B16F10 model. Approximately 99% of the tumor mass was surgically removed at day 6 after tumor inoculation. cGAMP-MPs and cGAMP-S were directly deposited at the surgical bed. FIGS. 6B-6C are graphs showing the average tumor growth curve (FIG. 6B) and survival analysis (FIG. 6C) of treated mice (n=8). FIGS. 6D-6E are graphs showing tumor growth (FIG. 6D) and survival (FIG. 6E) monitored over time (n=6) in tumor-free mice after cGAMP-MPs and 3×cGAMP-S treatments, which were rechallenged with B16F10 cells at day 60 post tumor inoculation. Data represent average±s.e.m. FIG. 6F is a schematic representation of the treatment regimen on an orthotopic pancreatic tumor model. FIGS. 6G-6H show representative images (FIG. 6G) and weight analysis (FIG. 6H) of isolated tumors from pancreas. Statistical significance was calculated by one way or two-way ANOVA and Tukey's multiple comparisons test: *$P<0.05$, $P<0.01$, *$P<0.001$, ****$P<0.0001$.

DETAILED DESCRIPTION OF THE INVENTION

I. Definitions

Figure 1A:
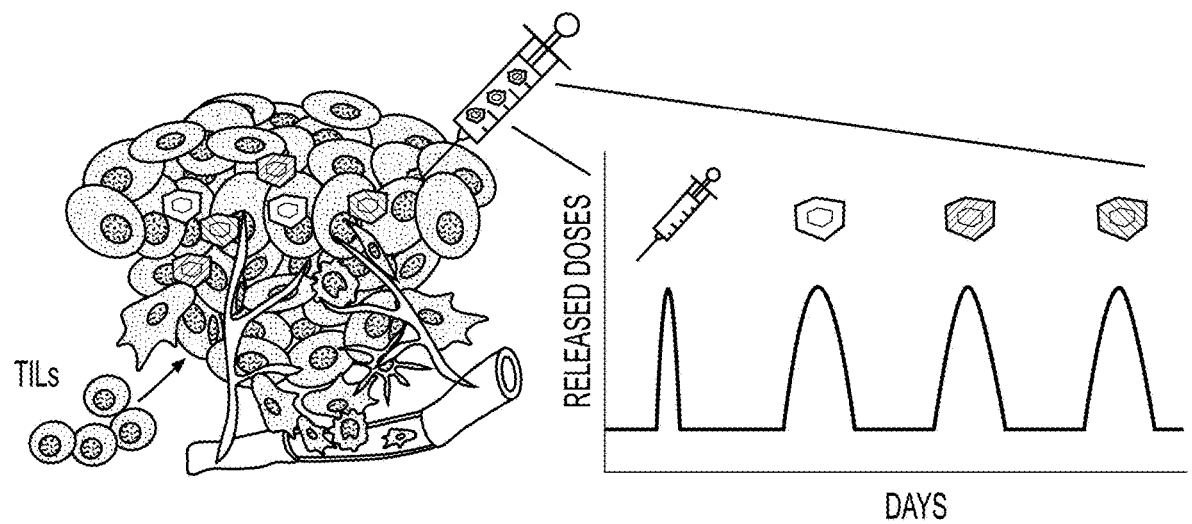
FIGS. 1A-1E are diagrams showing the design and fabrication of PLGA microdevices (PLGA-MPs).

As used herein, "microdevice" refers to microstructures with diverse or complex three-dimensional geometric shapes which cannot be formed using standard techniques such as emulsion or solvent evaporation techniques. The microdevices may have one or more internal compartments, with an outer shell that is formed by solvent and/or heat bonding of discrete powder or suspensions to form the desired shape and dimension. The microdevices may have diverse compartment geometries, external shell geometries, or diverse geometries of both the compartment and the external shell. For example, the compartment and the shell may have the same geometric shape, such as a cube-shaped compartment, and a cube-shaped shell. The compartment and the shell may have different geometric shapes, such as the compartment may be a cube, while the shell may be star-shaped, or a cone. The devices may be formed by bringing together a "base" device and a cap. Although described with reference to "a compartment", it is understood that there may be multiple compartments, of the same or different dimensions and shapes.

The microdevices have microscale external dimensions, such as a length, width, height, or diameter, up to less than one centimeter in at least one dimension, more preferably having a maximum diameter between 1 micrometer (μm) and 1000 μm. As used herein, the "diameter" of a non-spherical microdevice refers to the largest linear distance between two points on the surface of the microdevice, or between two points of a non-spherical compartment. When referring to multiple microdevices or multiple compartments, the diameter of the microdevices or compartments typically refers to the average diameter of the microdevices. Diameter of microdevices or compartments can be measured using a variety of techniques, including, but not limited to, optical or electron microscopy. The diameter of microdevices can measured with dynamic light scattering. For spherical microparticles, the "diameter" is used in the art-recognized definition.

As used herein "base", or "bases" in a context of a microdevice refers to the base of the microdevice.

As used herein, "cap" or "caps" refers to a structure that is used to cap the base or bases. The cap may have any geometric shape, and the geometric shape may be the same as that of the base, or different.

"Additive manufacturing" or "3D printing" as used herein refers to a process of making a three-dimensional solid object of virtually any shape from a digital model. 3D printing is achieved using an additive process, where successive layers of material are laid down in different shapes or thicknesses. In some embodiments, "3D printing" uses an extruded or solvent based polymer-containing ink (e.g., PLGA, poly(L-lactide) ("PLLA"), etc.) that is jetted or extruded through a nozzle and solidified into a desired shape. The shape can be controlled in the x, y and z directions.

"Micromolding," as used herein, generally refers to processes suitable for manufacturing parts or devices on a microscale, or processes suitable for manufacturing parts or devices having features or tolerances on a microscale. Exemplary techniques include, but are not limited to, lithography.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrade or break down into their component subunits in the body, as a function of hydrolysis and/or enzymatic degradation.

The term "homogeneous" as used in the context of microdevices refers to a collection of two or more individual microdevices that are of the same kind. For example, the homogeneous microdevices can have a uniform composition (e.g., formed from the same polymer or co-polymer), structure (e.g., 3D geometry), agent (e.g., encapsulating the same therapeutic and/or prophylactic agent), and combinations thereof. "Heterogeneous" as used in the context of microdevices means not homogeneous. For example, in some embodiments, heterogeneous microdevices do not have a uniform composition (e.g., formed from the same polymer or co-polymer), structure (e.g., 3D geometry), agent (e.g., encapsulating the same therapeutic and/or prophylactic agent), and combinations thereof.

As used herein, the term "agonist" refers to a molecule that binds to a receptor and activates the receptor to produce a biological response. Receptors can be activated by either an endogenous or an exogenous agonist. The agonist can be a full, partial, or inverse agonist.

"Immune response," as used herein, typically refers to responses that induce, increase, or perpetuate the activation or efficiency of innate and/or adaptive immunity. The immune response can be a specific response to an antigen, including cancer antigens, or vaccine that produces immunity to a current or future exposure in a host, such as a mammal.

"Hydrophilic," as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic," as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

"Treatment" or "treating" means to administer a composition to a subject or a system with an undesired condition (e.g., cancer). The condition can include one or more symptoms of a disease, pathological state, or disorder. Treatment includes medical management of a subject with the intent to cure, ameliorate, stabilize, or prevent a disease, pathological condition, or disorder. This includes active treatment, that is, treatment directed specifically toward the improvement of a disease, pathological state, or disorder, and also includes causal treatment, that is, treatment directed toward removal of the cause of the associated disease, pathological state, or disorder. In addition, this term includes palliative treatment, that is, treatment designed for the relief of symptoms rather than the curing of the disease, pathological state, or disorder; preventative treatment, that is, treatment directed to minimizing or partially or completely inhibiting the development of the associated disease, pathological state, or disorder; and supportive treatment, that is, treatment employed to supplement another specific therapy directed toward the improvement of the associated disease, pathological state, or disorder. It is understood that treatment, while intended to cure, ameliorate, stabilize, or prevent a disease, pathological condition, or disorder, need not actually result in the cure, amelioration, stabilization or prevention. In some embodiments, treatment means to administer a composition in an amount sufficient to reduce, alleviate or ameliorate one or more symptoms of a disorder, disease, or condition being treated. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

"Prevention" or "preventing" means to administer a composition to a subject or a system at risk for an undesired condition (e.g., cancer). The condition can include one or more symptoms of a disease, pathological state, or disorder. The condition can also be a predisposition to the disease, pathological state, or disorder. The effect of the administration of the composition to the subject can be the cessation of a particular symptom of a condition, a reduction or prevention of the symptoms of a condition, a reduction in the severity of the condition, the complete ablation of the condition, a stabilization or delay of the development or progression of a particular event or characteristic, or reduction of the chances that a particular event or characteristic will occur.

As used herein, the terms "effective amount" or "therapeutically effective amount" means a quantity sufficient to alleviate or ameliorate one or more symptoms of a disorder, disease, or condition being treated, or to otherwise provide a desired pharmacologic and/or physiologic effect. Such amelioration only requires a reduction or alteration, not necessarily elimination. The precise quantity will vary according to a variety of factors such as subject-dependent variables (e.g., age, immune system health, weight, etc.), the disease or disorder being treated, as well as the route of administration, and the pharmacokinetics and pharmacodynamics of the agent being administered.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites.

The term "small molecule," as used herein, generally refers to an organic molecule that is less than about 2000 g/mol in molecular weight, less than about 1500 g/mol, or less than about 1000 g/mol. Small molecules are non-polymeric and/or non-oligomeric.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

Use of the term "about" is intended to describe values either above or below the stated value in a range of approximately +/−10%; in other embodiments the values may range in value either above or below the stated value by approximately +/−5%.

II. Compositions

Polymeric microdevices and compositions thereof suitable for delivering one or more therapeutic and/or prophylactic agents which bind to a receptor, particularly one or more STING agonists, have been developed for use as a delivery system that provides sustained and/or intermittent or pulsatile release of the agent over a period of time through a single injection.

A. Polymeric Microdevices

Polymeric microdevices, and compositions and formulations containing such microdevices, can have diverse three-dimensional geometries, and contain one or more discrete internal cavities, such as a compartment. The compartment may contain a therapeutic and/or prophylactic agent such as a STING agonist, as well as excipients or other inert ingredients and release controlling materials.

1. Polymers

The microdevices are formed from one or more polymers or co-polymers. In preferred embodiments, the polymer is biocompatible and biodegradable. The microdevices can be made with hydrophobic polymers, hydrophobic polymers blended with hydrophilic polymers, amphiphilic polymers, or mixtures thereof.

Hydrophilic polymers include cellulosic polymers such as starch and polysaccharides, hydrophilic polypeptides, poly(amino acids) such as poly-L-glutamic acid (PGS), gamma-polyglutamic acid, poly-L-aspartic acid, poly-L-serine, or poly-L-lysine, polyalkylene glycols and polyalkylene oxides such as polyethylene glycol (PEG), polypropylene glycol (PPG), and poly(ethylene oxide) (PEO), poly(oxyethylated polyol), poly(olefinic alcohol), polyvinylpyrrolidone), poly(hydroxyalkylmethacrylamide), poly(hydroxyalkylmethacrylate), poly(saccharides), poly(hydroxy acids), poly(vinyl alcohol), and copolymers thereof.

Examples of hydrophobic polymers include polyhydroxyacids such as poly(lactic acid), poly(glycolic acid), and poly(lactic acid-co-glycolic acid), polyhydroxyalkanoates such as poly3-hydroxybutyrate or poly4-hydroxybutyrate, polycaprolactones, poly(orthoesters), polyanhydrides, poly(phosphazenes), poly(lactide-co-caprolactones), polycarbonates such as tyrosine polycarbonates, polyamides (including synthetic and natural polyamides), polypeptides, and poly(amino acids), polyesteramides, polyesters, poly(dioxanones), poly(alkylene alkylates), hydrophobic polyethers, polyurethanes, polyetheresters, polyacetals, polycyanoacrylates, polyacrylates, polymethylmethacrylates, polysiloxanes, poly(oxyethylene)/poly(oxypropylene) copolymers, polyketals, polyphosphates, polyhydroxyvalerates, polyalkylene oxalates, polyalkylene succinates, poly(maleic acids), as well as copolymers thereof. In certain embodiments, the hydrophobic polymer is an aliphatic polyester. In preferred embodiments, the hydrophobic polymer is poly(lactic acid), poly(glycolic acid), or poly(lactic-co-glycolic acid)(PLGA).

Biodegradable polymers can include polymers that are insoluble or sparingly soluble in water that are converted chemically or enzymatically in the body into water-soluble materials. Biodegradable polymers can include soluble polymers crosslinked by hydrolyzable cross-linking groups to render the crosslinked polymer insoluble or sparingly soluble in water.

Amphiphilic polymers are polymers containing a hydrophobic polymer block and a hydrophilic polymer block. The hydrophobic polymer block can contain one or more of the hydrophobic polymers above or a derivative or copolymer thereof. The hydrophilic polymer block can contain one or more of the hydrophilic polymers above or a derivative or copolymer thereof.

In particularly preferred embodiments, the biodegradable polymers are polyesters or polyanhydrides such as poly(lactic acid), poly(glycolic acid), and poly(lactic-co-glycolic acid). Polyester homopolymers include glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA," and caprolactone units, such as poly(ε-caprolactone), collectively referred to herein as "PCL," and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA," and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers." In certain embodiments, the PEG region can be covalently associated with polymer to yield "PEGylated polymers" by a cleavable linker.

The polymers may undergo a phase change based on physical or chemical changes of the environment. Exemplary environmental triggers that may change the polymer's physical or chemical characteristics, such as solubility, degradation rate, crosslinking, and rate of erosion, include changes in temperature, changes in pH, and changes in ionic strength.

The polymer can contain be a blend or copolymers of two or more polymers. The polymer may also contain other entities such as stabilizers, surfactants, or lipids.

2. Structure

The microdevices can have a complex three-dimensional geometry. The microdevices may be solid, layered and/or include a compartment. Typically, the microdevice contains a shell/base, which has one or more internal compartment, and a cap sealing the compartment (see e.g., FIG. 1B). The layers and/or compartment may contain an agent (see e.g., FIG. 1B).

The microdevices can have a geometrical shape including, but not limited to, a cube, cuboid, star, cylinder, rectangular prism, triangular prism, pentagonal prism, octahedron, diamond, ellipsoid, and sphere. The compartment(s) of the microdevices can contain one or more discrete regions within one or more compartments, and have a complex 3D geometry.

Microdevices generally have external dimensions, such as a length, width, height, or diameter, each between 50 micrometer (μm) and 1000 μm, 50 micrometer (μm) and 550 μm, 50 micrometer (μm) and 500 μm, 50 micrometer (μm) and 450 μm, 50 micrometer (μm) and 400 μm, between 50 μm and 350 μm, between 50 μm and 300 μm, between 50 μm and 250 μm, between 50 μm and 200 μm, between 50 μm and 150 μm, and between 50 μm and 100 μm. For example, external dimensions for a cuboid-shaped microdevice may be about 250 μm, about 300 μm, or about 400 μm for length, about 250 μm, about 300 μm, or about 400 μm for width, and about 250 μm, about 300 μm, or about 400 μm for height.

The compartment can generally have microscale dimensions, such as a length, width, height, or diameter, each between 10 μm and 850 μm, between 10 μm and 800 μm, between 10 μm and 750 μm, between 10 μm and 700 μm, between 10 μm and 650 μm, between 10 μm and 600 μm, between 10 μm and 550 μm, between 10 μm and 500 μm, between 10 μm and 450 μm, between 10 μm and 400 μm, between 10 μm and 350 μm, between 10 μm and 300 μm, between 10 μm and 250 μm, between 10 μm and 200 μm, between 10 μm and 150 μm, between 10 μm and 100 μm, between 10 μm and 50 μm.

Exemplary dimensions for a cube- or cuboid-shaped compartment include length, width, and height of about 10 μm, about 20 μm, about 30 μm, about 40 μm, about 50 μm, about 60 μm, about 70 μm, about 80 μm, about 90 μm, about 100 μm, about 110 μm, about 120 μm, or about 130 μm, or about 140 μm, about 150 μm, about 200 μm, about 250 μm, or about 300 μm. For example, dimensions for a cuboid-shaped compartment may be about 100 μm, about 150 μm, about 200 μm, or about 250 μm for length, about 100 μm, about 150 µm, about 200 µm, or about 250 µm for width, and about 100 µm, about 150 µm, about 200 µm, or about 250 µm for height.

The experiments in the working Examples below utilized sealed microdevices having external dimensions of 400×400×300 µm (length×width×height), a wall thickness of 100 µm in each dimension, and with an internal cavity of 200×200×100 µm (length×width×height). However, alternative external and internal cavity dimensions are also provided, and can be independently selected by the practitioner, to fine tune microdevices to different external and/or internal cavity shapes and sizes, with different wall thicknesses, and combinations thereof.

3. Microdevice Composition

The different components of the microdevices may be formed of the same polymer composition, different polymers and/or a blend of two or more polymer compositions in one microdevice shell or walls of the inner compartment. For example, in a microdevice having a shell/base and a cap, the base may be formed form one polymer or co-polymer, while the cap may be formed from another polymer or co-polymer. For example, the cap may be of the same polymer composition as that used for forming the base but with chemically modified ends. In another example, the cap may be formed of a polymer that differs from the polymer used for forming the shell/base by inclusion of different monomers, different co-polymers, having a different degree of polymerization, a different co-polymer ratio, a different blend, or a combination thereof.

In one embodiment, the polymer for forming the microdevice shell/base is PLGA, and the PLGA polymer for forming the cap has modified ends, such as ester ends, to aid sealing with the shell/base at lower sealing temperature. Maintaining a low sealing temperature minimizes stress on the agent incorporated in the compartment. PLGA caps with ester ends also have increased hydrophobicity, which delays the onset of release of a therapeutic and/or prophylactic agent contained within the compartment.

B. Therapeutic and Prophylactic Agents

The microdevices may enclose one or more agents (e.g., therapeutic and/or prophylactic agents) which bind to a receptor to inhibit or activate the receptor. Typically, the agent is present in or incorporated with the compartment of the microdevice. Agents to be included in the microdevices can be proteins or peptides, sugars or carbohydrate, nucleic acids or oligonucleotides, lipids, small molecules (e.g., molecular weight less than 2000 Daltons, preferably less than 1500 Daltons, more preferably 300-700 Daltons), or combinations thereof.

Immunomodulatory Agents

In some preferred embodiments, the microdevices contain one or more immune receptor binding agents such as STING agonists as an immunomodulatory therapeutic and/or prophylactic agent.

In some embodiments, the agent is not a vaccine antigen, adjuvant, or combination, thereof.

STING Agonists

Stimulator of interferon genes (STING) is a cytosolic receptor that senses both exogenous and endogenous cytosolic cyclic dinucleotides (CDNs), activating TBK1/IRF3 (interferon regulatory factor 3), NF-κB (nuclear factor κB), and STAT6 (signal transducer and activator of transcription 6) signaling pathways to induce robust type I interferon and proinflammatory cytokine responses. STING is encoded by the TMEM173 gene. It works as both a direct cytosolic DNA sensor (CDS) and an adaptor protein in Type I interferon signaling through different molecular mechanisms. It has been shown to activate downstream transcription factors STAT6 and IRF3 through TBK1, which are responsible for antiviral response and innate immune response against intracellular pathogen.

STING resides in the endoplasmic reticulum, but in the presence of cytosolic DNA, the sensor cGAS binds to the DNA and produces cyclic dinucleotides. This di-nucleotide binds to STING and promotes its aggregation and translocation from the ER through the Golgi to perinuclear sites. There, STING complexes with TBK1 and promotes its phosphorylation. Once TBK1 is phosphorylated, it phosphorylates the transcription factor IRF3, which dimerizes and translocates to the nucleus, where it activates the transcription of type I IFN and other innate immune genes.

STING induces antitumor CD8 T responses in mouse models of cancer. In the tumor microenvironment, T cells, endothelial cells, and fibroblasts, stimulated with STING agonists ex vivo produce type-I IFNs (Corrales, et al., Cell Rep (2015) 11(7):1018-30). In contrast, tumor cells can inhibit STING pathway activation, potentially leading to immune evasion during carcinogenesis (He, et al., Cancer Lett (2017) 402:203-12; Xia, et al., Cancer Res (2016) 76(22):6747-59). Evidence shows that activation of the STING pathway correlates with the induction of a spontaneous antitumor T-cell response involving the expression of type-I IFN genes (Chen, et al., Nat Immunol (2016) 17(10): 1142-9; Barber, et al., Nat Rev Immunol (2015) 15(12):760-70; Woo, et al., Immunity (2014) 41(5):830-42). Furthermore, host STING pathway is required for efficient cross-priming of tumor-Ag specific CD8+ T cells mediated by DCs (Woo, et al., Immunity (2014) 41(5):830-42; Deng, et al., Immunity (2014) 41(5):843-52). Based on these results, direct pharmacologic stimulation of the STING pathway has been explored as a cancer therapy.

Any STING agonists known in the art can be used in accordance with the compositions and methods. The STING agonist can be a nucleic acid, a protein, a peptide, a polymer, or a small molecule. The STING agonist can be natural or synthetic. In some embodiments, the STING agonist is hydrophilic.

Suitable STING agonists include cyclic dinucleotides (CDNs) or non-cyclic dinucleotide agonists. Cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAIMP), and any analogue thereof, can be used. The CDNs may have 2'3', 2'5', 3'3', or 3'5' bonds linking the cyclic dinucleotides, or any combination thereof. For example, 2'3'-cGAMP or 3'3'-cGAMP can be used. Cyclic purine dinucleotides may be modified via standard organic chemistry techniques to produce analogues of purine dinucleotides. Suitable purine dinucleotides include, but are not limited to, adenine, guanine, inosine, hypoxanthine, xanthine, isoguanine, or any other appropriate purine dinucleotide known in the art. The cyclic dinucleotides may be modified analogues. Any suitable modification known in the art may be used, including, but not limited to, phosphorothioate, biphosphorothioate, fluorinate, and difluorinate modifications.

In some embodiments, the cyclic dinucleotides may include modified cyclic dinucleotides, such as a compound of the formula:

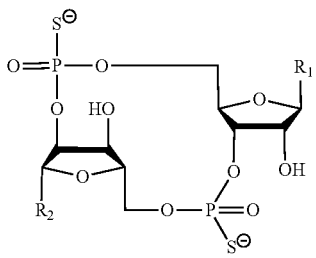

In further embodiments, R1 and R2 may be independently 9-purine, 9-adenine, 9-guanine, 9-hypoxanthine, 9-xanthine, 9-uric acid, or 9-isoguanine.

Suitable STING agonists include stereoisomers of cyclic purine dinuclotides (e.g., substantially pure Rp,Rp or Rp,Sp diastereomers thereof). c-di-AMP, c-di-GMP, c-di-IMP, c-AMP-GMP, c-AMP-IMP, and c-GMP-IMP, and analogs thereof including, but not limited to, phosphorothioate analogues, referred to herein as "thiophosphates" can be used. Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA POL 1 exonuclease, nucleases 51 and P1, RNases, serum nucleases and snake venom phosphodiesterase. In addition, the potential for crossing the lipid bilayer increases.

A phosphorothioate linkage is inherently chiral. The skilled artisan will recognize that the phosphates in this structure may each exist in R or S forms. Thus, Rp,Rp, Sp,Sp, and Rp,Sp forms are possible. In each case, preferred are substantially pure Rp,Rp and Rp,Sp diastereomers of these molecules.

Suitable cyclic purine dinuclotides also include 2'-O-substituted forms of CDNs, and in particular CDN thiophosphates. Additional stability and bioavailability can be provided by the substitution of the 2'-OH of the ribose moiety. Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino (=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_b$) and sulfonamidyl (—S(O)$_2$N($R_{bb}$)($R_{cc}$) or N($R_{bb}$)S(O)$_2R_{bb}$). Wherein each $R_{aa}$, $R_{bb}$ and $R_{cc}$ is, independently, H, an optionally linked chemical functional group or a further substituent group such as, H, alkyl, alkenyl, alkynyl, aliphatic, alkoxy, acyl, aryl, aralkyl, heteroaryl, alicyclic, heterocyclic and heteroarylalkyl. Suitable cyclic purine dinuclotides also include S-substituent forms of CDNs, and in particular CDN thiophosphates, which can advantageously provide prodrugs with improved bioavailability.

Non cyclic dinucleotide agonists may also be used, such as 5,6-Dimethylxanthenone-4-acetic acid (DMXAA; also known as Vadimezan or ASA404), or any other non-cyclic dinucleotide agonist known in the art.

Exemplary STING agonists include, but are not limited to, STING agonist-1, ML RR-S2 CDA, ML RR-S2c-di-GMP, ML-RR-S2 cGAMP, 2' 3'-c-di-AM(PS)2, 2'3'-cGAMPdFHS, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 2'3'-cGsAsMP (bisphosphothioate analog of 2'3'-cGAMP), 3'3'-cGAMP, c-di-AMP, 2'3'-c-di-AMP, 2'3'-c-di-AM(PS)2, c-di-GMP, 2'3'-c-di-GMP, c-di-IMP, c-di-UMP, MK-2118, GSK3745417, TAK-676, CRD5500, SB 11325, SB 11396, TTI-10001, MAVU-104 (ENPP1 inhibitor), Dispiro diketopiperzine (DSDP) (see Antiviral research. 2017 Nov. 1; 147:37-46), Benzo[b][1,4]thiazine-6-carboxamide (indirect STING agonist), a-Mangostin (human STING-preferring agonist), Benzamide and its analogues (see ACS Infect Dis 2019; 5; 1139-49), Bicyclic benzamides, and Benzothiophene derivatives. Suitable STING agonists also include those disclosed in US 2016/0287623, WO 2019/183578, WO 2019/069270, WO 2019/069275, U.S. Pat. Nos. 9,695,212, 9,724,408, 10,450,341, WO 2019/079261, WO 2018/234805, WO 2018/234808, WO 2018/067423 and Ramanjulu J M., et al., Nature, 564(7736):439-443 (2018) which discloses amidobenzimidazole (ABZI) compounds as STING agonists, all of which are hereby incorporated by reference in their entirety.

In a preferred embodiment, the STING agonist is selected from the group including cGAMP, DMXAA, MK-1454, MK-2118, E7766, MIW815 (ADU-S100), BMS-986301, GSK3745417, IMSA-101, SYNB1891 (E. coli), SITX-799 (Silicon Therapeutics), and SB 11285.

The STING agonists can be functionalized, for example with ether, ester, or amide linkage, if desired. For example, DMXAA can be modified to DMXAA ester, DMXAA ether, or DMXAA amide.

C. Additional Agents

The compositions and methods optionally include one or more additional therapeutic agents. The additional therapeutic agent can be administered in particulate or soluble form, using the same or a different delivery system, in the same or different pharmaceutical composition, and delivered to the subject in need thereof at the same or different time from the microdevices loaded with the first therapeutic agent, e.g., a STING agonist.

Thus, in some embodiments, the same or different microdevices are used to deliver one or more additional agents, particularly one or more active agents to prevent or treat one or more symptoms of a disease (e.g., cancer). The additional active agent can be co-loaded into the same microdevice, or microdevices of the same or different formulation.

Suitable additional therapeutic and/or prophylactic agents can be a biomolecule, such as an enzyme, protein, polypeptide, antibody or fragment thereof, or nucleic acid (e.g., a functional RNAs such as siRNA or miRNA), or a small molecule agent (e.g., molecular weight less than 2000 Daltons, preferably less than 1500 Daltons, more preferably 300-700 Daltons), including organic, inorganic, and organometallic agents. The agent(s) can be incorporated within the microdevice compartment.

1. Representative Additional Agents

The microdevices can also include one or more therapeutic and/or prophylactic agents that are immunomodulatory agents. Representative additional agents include, but are not limited to, chemotherapeutic agents, immunomodulatory agents, including Toll-like receptor 9 (TLR9) agonists (e.g., CpG DNA) which stimulate the immune response, and combinations thereof. The additional agents can be provided with STING agonists or by themselves in microdevices.

2. Immunomodulatory Agents

The terms "immunomodulatory agent" and "immunotherapeutic agent" refer an active agent that elicits a specific effect upon the immune system of the recipient. Immunomodulation can include suppression, reduction, enhancement, prolonging or stimulation of one or more physiological processes of the innate or adaptive immune response, as compared to a control. Typically, immunomodulatory agents can modulate immune microenvironment for a desired immunological response (e.g., increasing anti-tumor activity, or increasing inflammatory activities at sites in need thereof) by targeting one or more immune cells or cell types at a target site, and thus, are not necessarily specific to any cancer type. In some embodiments, the immunomodulatory agents specifically kill, inhibit, or reduce activity or quantity of suppressive immune cells, such as tumor associated macrophages, for an enhanced anti-tumor response at a tumor site. In some embodiments, the immunomodulatory agents specifically enhance activity or quantity of cytotoxic immune cells, such as CD8+ T cells, for an enhanced anti-tumor response at a tumor site.

3. Chemotherapeutic Agents

In some embodiments, the additional therapeutic agents are any inhibitors targeting one or more of EGFR, ERBB2, VEGFRs, Kit, PDGFRs, ABL, SRC and mTOR. In some embodiments, the additional therapeutic agents are tyrosine kinase inhibitors such as HER2 inhibitors, EGFR tyrosine kinase inhibitors. Exemplary EGFR tyrosine kinase inhibitors include gefitinib, erlotinib, afatinib, dacomitinib, and osimertinib.

The majority of chemotherapeutic drugs can be divided into alkylating agents, antimetabolites, anthracyclines, plant alkaloids, topoisomerase inhibitors, and other antitumour agents. These drugs affect cell division or DNA synthesis and function in some way. Thus in some embodiments, chemotherapeutic agents that can be included include, but are not limited to, alkylating agents, antimetabolites, antimitotics, anthracyclines, cytotoxic antibiotics, topoisomerase inhibitors, and combinations thereof. Monoclonal antibodies and the tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors) can also be used. Other suitable anti-cancer agents include angiogenesis inhibitors including antibodies to vascular endothelial growth factor (VEGF) such as bevacizumab (AVASTIN®) and rhuFAb V2 (ranibizumab, LUCENTIS®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (NEXAVAR®), erlotinib (TARCEVA®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Representative chemotherapeutic agents that can be used include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarbamide, idarubicin, ifosfamide, innotecan, leucovorin, liposomal doxorubicin, liposomal daunorubici, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2)5 and combinations thereof.

4. Immune Checkpoint Modulators

Strategies that combine STING immunotherapy with other immunomodulatory agents are being explored. The enforced activation of STING by intratumoral injection of cyclic dinucleotide GMP-AMP (cGAMP), potently enhanced antitumor CD8 T cell responses leading to growth control of injected and contralateral tumors in mouse models of melanoma and colon cancer. The ability of cGAMP to trigger antitumor immunity was further enhanced when combined with anti-programmed death-1 (PD-1) and anti-cytotoxic T-lymphocyte associated-4 (CTLA-4) antibodies (Demaria, et al., Proc Natl Acad Sci USA (2015) 112(50): 15408-13). In other studies, cyclic dinucleotides (CDNs) together with anti-programmed death-L1 blocking antibody incited much stronger antitumor effects than monotherapy in a mouse model of squamous cell carcinoma model as well as of melanoma (Gadkaree, et al., Head Neck (2017) 39(6): 1086-94; Wang, et al., Proc Natl Acad Sci USA (2017) 114(7):1637-42). Luo et al. showed that combining a STING-activating nanovaccine and an anti-PD1 antibody generated long-term antitumor memory in TC-1 tumor model (Luo, et al., Nat Nanotechnol (2017) 12(7):648-54). Thus, in some embodiments, a STING agonist is combined with another immunomodulator agent, for example, one that uses the same or a different mechanism to enhance the immune response, preferably against cancer.

In preferred embodiments, the additional agent is an inhibitor of checkpoint proteins such as components of the PD-1/PD-L1 axis or CD28-CTLA-4 axis (e.g., PD-1 antagonists, PD-1 ligand antagonists, and CTLA4 antagonists). Exemplary immune checkpoint inhibitors include Pembrolizumab (anti-PD1 mAb), Durvalumab (anti-PDL1 mAb), PDR001 (anti-PD1 mAb), Atezolizumab (anti-PDL1 mAb), Nivolumab (anti-PD1 mAb), Tremelimumab (anti-CTLA4 mAb), Avelumab (anti-PDL1 mAb), Ipilimumab (anti-CTLA4 mAb), and RG7876 (CD40 agonist mAb), and other described in more details below.

In some embodiments, the active agent is a PD-1 antagonist. Activation of T cells normally depends on an antigen-specific signal following contact of the T cell receptor (TCR) with an antigenic peptide presented via the major histocompatibility complex (MHC) while the extent of this reaction is controlled by positive and negative antigen-independent signals eminating from a variety of co-stimulatory molecules. The latter are commonly members of the CD28/B7 family. Conversely, Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U. S. A*, 105:10275-10276 (2008)). Therefore, proteins, antibodies or small molecules that prevent co-ligation of PD-1 and TCR on the T cell membrane are also useful PD-1 antagonists.

In preferred embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods include antibodies that bind to PD-1 or ligands of PD-1, and other antibodies.

Suitable anti-PD-1 antibodies include, but are not limited to, those described in the following publications:
PCT/IL03/00425 (Hardy et al., WO/2003/099196)
PCT/JP2006/309606 (Korman et al., WO/2006/121168)
PCT/US2008/008925 (Li et al., WO/2009/014708)
PCT/JP03/08420 (Honjo et al., WO/2004/004771)
PCT/JP04/00549 (Honjo et al., WO/2004/072286)
PCT/IB2003/006304 (Collins et al., WO/2004/056875)
PCT/US2007/088851 (Ahmed et al., WO/2008/083174)
PCT/US2006/026046 (Korman et al., WO/2007/005874)
PCT/US2008/084923 (Terrett et al., WO/2009/073533)
Berger et al., *Clin. Cancer Res.*, 14:30443051 (2008).

A specific example of an anti-PD-1 antibody is MDX-1106 (see Kosak, US 20070166281 (pub. 19 Jul. 2007) at par. 42), a human anti-PD-1 antibody, preferably administered at a dose of 3 mg/kg.

Exemplary anti-B7-H1 antibodies include, but are not limited to, those described in the following publications:
PCT/US06/022423 (WO/2006/133396, pub. 14 Dec. 2006)
PCT/US07/088851 (WO/2008/083174, pub. 10 Jul. 2008)
US 2006/0110383 (pub. 25 May 2006)

A specific example of an anti-B7-H1 antibody is MDX-1105 (WO/2007/005874, published 11 Jan. 2007)), a human anti-B7-H1 antibody.

For anti-B7-DC antibodies see U.S. Pat. Nos. 7,411,051, 7,052,694, 7,390,888, and U.S. Published Application No. 2006/0099203.

The antibody can be a bi-specific antibody that includes an antibody that binds to the PD-1 receptor bridged to an antibody that binds to a ligand of PD-1, such as B7-H1. In some embodiments, the PD-1 binding portion reduces or inhibits signal transduction through the PD-1 receptor.

Other exemplary PD-1 receptor antagonists include, but are not limited to, B7-DC polypeptides, including homologs and variants of these, as well as active fragments of any of the foregoing, and fusion proteins that incorporate any of these. In a preferred embodiment, the fusion protein comprises the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, preferably from mouse or primate, preferably human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., *PNAS*, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., *J. Clin. Invest.* 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

In some embodiments, the molecule is an agent binds to an immune response mediating molecule that is not PD-1. In a preferred embodiment, the molecule is an antagonist of CTLA4, for example an antagonistic anti-CTLA4 antibody. An example of an anti-CTLA4 antibody contemplated for use in the provided methods includes an antibody as described in PCT/US2006/043690 (Fischkoff et al., WO/2007/056539).

Dosages for anti-PD-1, anti-B7-H1, and anti-CTLA4 antibody, are known in the art and can be in the range of 0.1 to 100 mg/kg, with more narrow ranges of 1 to 50 mg/kg preferred and ranges of 10 to 20 mg/kg being more preferred. An appropriate dose for a human subject is between 5 and 15 mg/kg, with 10 mg/kg of antibody (for example, human anti-PD-1 antibody, like MDX-1106) most preferred.

Specific examples of an anti-CTLA4 antibody are Ipilimumab, also known as MDX-010 or MDX-101, a human anti-CTLA4 antibody, preferably administered at a dose of about 10 mg/kg, and Tremelimumab a human anti-CTLA4 antibody, preferably administered at a dose of about 15 mg/kg. See also Sammartino, et al., *Clinical Kidney Journal*, 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.*, 277:7363-7368 (2002). Such small organics could be administered alone or together with an anti-CTLA4 antibody to reduce inhibitory signal transduction of T cells.

III. Pharmaceutical Formulations

Pharmaceutical compositions contain microdevices including one or more agents and a pharmaceutically acceptable buffer, carrier, diluent or excipient. Pharmaceutical compositions may be formulated in a conventional manner using one or more physiologically acceptable carriers including excipients and auxiliaries which facilitate processing of the active agents and microdevices into preparations which can be used pharmaceutically.

Pharmaceutically acceptable excipients include compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. Pharmaceutically acceptable excipients include, but are not limited to, carriers, thickeners, diluents, buffers, preservatives, binders, lubricants, disintegrators, swelling agents, fillers, stabilizers, and combinations thereof. These include suspending agents such as sterile water, phosphate buffered saline, saline, or a non-aqueous solution such as glycerol.

Proper formulation is dependent upon the route of administration chosen. In preferred embodiments, the compositions are formulated for local administration. In some embodiments, the compositions are formulated for intratumoral injection, intramuscular injection, or subcutaneous injection. Typically the compositions will be formulated in sterile saline or buffered solution or methyl cellulose solution for injection into the tissues to be treated. The compositions can be stored lyophilized in single use vials for rehydration immediately before use. Other suitable means for rehydration and administration known to those skilled in the art can be used.

Other representative excipients include solvents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the agent with a suitable organic ligand (e.g., quaternary ammonium salts). Lists of suitable salts are found, for example, in Remington's Pharmaceutical Sciences, 20th ed., Lippincott Williams & Wilkins, Baltimore, MD, 2000, p. 704.

Stabilizing Agents/Excipients

The agents to be incorporated into and/or delivered from the microdevice may be in combination with one or more stabilizing excipients. Alternatively, the stabilizing excipients may be included in the polymer shell, instead of the compartment of the microdevices. In other forms, the stabilizing excipients are present in both the compartment and the polymer of the microdevices.

The stabilizing excipients can increase the structural stability of thermolabile and/or pH sensitive agents. Exemplary stabilizing agents include sugars, sugar alcohols, amino acids, vitamins, anti-oxidants, salts, buffering agents, polysaccharides, oils, and combinations thereof. Agents that may benefit from stabilization include proteins, peptides, and nucleic acids.

Sugars are a typical group of stabilizing agents for proteins. Examples include simple sugars such as sorbitol, sucrose, fructose, mannitol, glucose, maltose, dextrose, and trehalose as well as more complex sugars. See Alcock et al., Long-term thermostabilization of live poxviral and adenoviral vaccine vectors at supraphysiological temperatures in carbohydrate glass. *Science Translational Medicine,* 2(19): 19-19ra12 (2010). Exemplary salts useful as stabilizing excipients, or stabilizing excipients, include magnesium chloride, calcium chloride, monosodium glutamate, potassium phosphate, and combinations thereof.

Exemplary buffering agents include $MgCO_3$, $CaCO_3$, $Mg(OH)_2$, $Al(OH)_3$, myristic acid, polymers such as poly-L-lysine, and combinations thereof. When incorporated into microdevices, the buffering agents minimize changes in pH of release medium. $Al(OH)_3$ is a known adjuvant and can increase immunogenicity. Other agents suitable as stabilizing agents excipients include maltodextrin, methyl cellulose, (hydroxypropyl)methyl cellulose (HPMC), calcium helptagluconate, carboxymethylcellulose (CMC), silk, glycerol, alginate, ectoines, ubiquitin, gelatin, threonine, peptone, glycine, glutamine, serum albumin, and combinations thereof.

The stabilizing excipients may be used in any combination and in any amount effective to stabilize the agent against temperature, storage, humidity, pH, and oxidation insults. For example, stabilizing agents sucrose, monosodium glutamate, magnesium chloride may be used in effective amounts to stabilize the agent. The buffering agent aluminum hydroxide may be included with the stabilizing agents to control changes in environment's pH as the polymer degrades, or as the microdevice passes through a digestive tract.

Stability of the incorporated agent(s) can be evaluated during each step of the encapsulation and/or manufacturing process, during storage (at 25° C., room temp, high humidity/high temp conditions, under physiological conditions (pH 7.2, 37° C.) and in vivo (animal models).

In some embodiments, the compositions are administered locally, for example, by injection directly into a site to be treated. Typically, local administration causes an increased localized concentration of the compositions which is greater than that which can be achieved by systemic administration. In some embodiments, the compositions are injected directly into a tumor (intratumoral injection). In some embodiments, the compositions are injected or otherwise administered onto vascular tissue at or adjacent to a site (e.g., tumor, surgery site).

A. Combinatorial Microdevice Formulations

As introduced above, microdevices of the same or different polymer composition, and/or having the same or different agent(s) may be combined within one formulation. In some embodiments, microdevices enclosing the same or different agent(s) are combined within a single formulation.

In some embodiments, microdevices differing in polymer composition may be combined within a single formulation.

The rate of release of agent(s) incorporated within the microdevices (e.g., STING agonist) can be tuned by the molecular weight (e.g., number-averaged molecular weight of the polymer or co-polymer, weight-averaged molecular weight of the polymer or co-polymer), polydispersity index of the polymer or co-polymer, chain end functionality of the polymer or co-polymer, the ratio of co-polymers, or a combination thereof. In some embodiments, the release kinetics can be tuned by the shell composition including 1) blending different ratios of PLA, PGA, or PLGA, and 2) blending different ratios of hydrophilic polymer, hydrophobic polymer, salts. The release kinetics can also be tuned by the wall thickness of a surface eroding polymer, such as polyanhydride or polyorthoester. Accordingly, the formulations can contain a population of microdevices that are homogeneous in terms of their polymer composition (and therefore, properties) and/or incorporated agent(s). In some embodiments, the formulations contain two or more (e.g., 2, 3, 4, 5 or more) populations of microdevices that are heterogeneous in terms of their polymer composition (and therefore, properties) and/or incorporated agent(s). In some embodiments, the formulations contain two or more (e.g., 2, 3, 4, 5 or more) different agents.

Formulations containing microdevices of the same polymeric composition but enclosing different agents may be formulated to provide two or more different agents simultaneously as the polymer degrades. The formulations may be useful for combination therapies, for co-delivery of drugs, with only a single administration.

Formulations containing microdevices with different polymeric composition but enclosing the same agent(s) may be formulated for providing two or more pulsatile releases at two or more time points following a single administration. As shown in the Examples, such formulations are useful for cancer therapies. A single administration of such formulations, allow for mimicking the repeat administration of drug or other agent as the timing of the pulsatile releases of incorporated agent(s) may be tuned.

Formulations containing microdevices with different polymeric composition and enclosing different agents may be formulated for providing two or more pulsatile releases at two or more time points as polymers of the different compositions degrade, releasing the different (e.g., 2, 3, 4, 5, or more) agents. Based on the composition of the microdevices, the formulations may release the two or more agents with each pulsatile release, or release only one type of agent with one release, and another type of agent with the subsequent release, following a single administration.

These formulations may be useful for cancer therapies, vaccination, or therapies for autoimmune diseases.

IV. Methods of Making the Microdevices

The methods used to manufacture the microdevices should maintain agent stability, both during processing and at body temperature, and that leakage following formation and administration are minimized. Post-formulation sterilization can typically be accomplished through a combination of sterile manufacturing conditions in combination with methods such as gamma irradiation. The microdevices can be made using any suitable technique known in the art, including, but not limited to micromolding.

Typically, a method of making the microdevice involves micromolding a polymeric base having a compartment therein, inserting agent into the compartment, placing a polymeric cap on the polymeric base, and sealing the polymeric cap to the polymeric base. Micromolding the polymeric base can involve layer-by-layer sintering under microscopic alignment. Suitable methods for manufacturing the microdevices are described in more detail below.

The microdevice compartment may be empty or contain one or more agents (e.g., solid or liquid agent). The agent is typically loaded into the compartment during the process of microdevice formation. The agent may be injected into the channel during or after formation of the microdevice, e.g., after formation of the shell/base. The volume of the compartment's void space varies with the size of the compartment, with the size of the microdevice, or both. Typically, the void space allows for loading of between pictogram (pg) and milligram (mg) of agent(s). Exemplary loadings include between 10 µg and 1 mg, such as about 100 µg, 1 µg, 2 µg, 3 µg, 4 µg, 5 µg, 10 µg, 100 µg, and 1 mg. Suitable ranges include between about 100 µg and 10 µg, between 1 µg and 5 µg, between 5 µg and 20 µg, between 15 µg and 50 µg, and between 50 µg and 150 µg.

Generally, the microdevices with compartments have a loading capacity between 1 percent weight to weight (% w/w) and 90% w/w, between 1% w/w and 85% w/w, between 1% w/w and 80% w/w, between 1% w/w and 75% w/w, between 1% w/w and 70% w/w, between 1% w/w and 65% w/w, between 1% w/w and 60% w/w, between 1% w/w and 55% w/w, between 1% w/w and 50% w/w, between 1% w/w and 45% w/w, between 1% w/w and 40% w/w, between 1% w/w and 35% w/w, between 1% w/w and 30% w/w, between 1% w/w and 25% w/w, between 1% w/w and 20% w/w, between 1% w/w and 15% w/w, between 1% w/w and 10% w/w, or between 1% w/w and 5% w/w for loading an agent. For example, individual microdevices may contain about 2% w/w, 4% w/w, 8% w/w, 5% w/w, 13% w/w, 19% w/w, 20% w/w, or 22% w/w loading capacity for loading an agent.

In some embodiments, the loading capacity of each microdevice is expressed as a fraction of the volume of the microdevice. The microdevices can have a loading capacity of between 1% and 80% by volume, between 1% and 75% by volume, between 1% and 70% by volume, between 1% and 65% by volume, between 1% and 60% by volume, between 1% and 55% by volume, between 1% and 50% by volume, between 1% and 45% by volume, between 1% and 40% by volume, between 1% and 35% by volume, between 1% and 30% by volume, between 1% and 25% by volume, between 1% and 20% by volume, between 1% and 15% by volume, between 1% and 10% by volume, or between 1% and 5% by volume for loading an agent. For example, the loading capacity of each microdevice can be about 8%-10% by volume, e.g., about 8.4% by volume.

An exemplary loading capacity is a loading of approximately 1 µg, 2 µg, 3 µg, 4 µg, 5 µg, 6 µg, 7 µg, 8 µg, 9 µg, or 10 µg of agent in each microdevice.

Solvents should be biocompatible, since some residue may be present in the polymeric formulations. Acceptable solvent residue should meet the Food and Drug Administration ("FDA") guidelines. Representative polymer solvents include organic solvents such as chloroform, dichloromethane, tetrafluoroethylene, and acyl acetate. The agent can be dissolved in aqueous or aqueous miscible solvents such as acetone, ethanol, methanol, isopropyl alcohol, and mixtures thereof.

Micromolding

Park et al., *Biomed. Microdevices*, 9:223-234 (2007), describes using micromolding to fabricate polymer microstructures having sophisticated designs. Micromolds were filled with polymer microdevices, to produce microstructures composed of multiple materials, having complex geometries, and made using mild processing conditions. These microdevices are typically prepared using an oil-water, double-emulsion system; spray drying methods; supercritical conditioning methods; and milling methods. In a preferred embodiment, micromolds can be prepared by photolithographically creating a female master mold made of photoresist, molding a male master structure out of polydimethylsiloxane (PDMS) from the female master mold and molding a female replicate mold out of PDMS from the male master structure. Polymer microdevices can be micromolded using temperature/press methods and/or from solvent.

Polymeric microdevices of 1 to 30 μm in size can be made from PLA, PGA and PLGA using spray drying and emulsion techniques. These polymer microdevices are filled into PDMS micromolds at room temperature and melted or bonded together, for example, by ultrasonically welding microdevices together in the mold while maintaining the voids inherent in their packing structure. Molds can be filled with solid polymer microdevices instead of a polymer melt to copy microstructures with complex geometries and composed of multiple materials using mild processing conditions. Microdevices can flow easily into the cavities of micromolds at room temperature and low pressure, which facilitates making microstructures with high aspect ratios. Moreover, polymer microdevices can incorporate chemical compounds, such as drugs, and can be filled into molds in sequential layers to accommodate multiple material compositions. After filling the mold, the final microstructures can be created by welding the microdevices within the mold by plastic welding methods, including thermal and ultrasonic welding as well as solvent and gas based welding.

These same techniques can be used to prepare the microdevice compositions having the polymeric materials and conditions required to exhibit a narrow time of release of an incorporated agent at specific time points following administration.

StampEd Assembly of polymer Layers (SEAL)

The microdevices can be produced using StampEd Assembly of polymer Layers (SEAL). See McHugh K J., et al., *Science*, 357(6356):1138-1142 (2017). The SEAL method creates an array of compartment-shell polymer devices. First, the polymer of choice, e.g., PLGA, is melt pressed using a prefabricated silicone mold. The mold is then transferred to another substrate where it is peeled off, leaving behind an array of polymer bases. These are then filled with any drug or other agents using an ink jet piezoelectric nozzle and then dried. Caps are then aligned with the base devices and sealed. The resulting array of compartment-shell microdevices are then removed from the base and stored until use.

1. Molds

In some embodiments, molds are formed as follows. Two or more silicon molds with complementary patterns is etched using standard microfabrication techniques. Polydimethylsiloxane (PDMS) is then cured on the surface of each silicon wafer to produce inverse elastomeric molds. A polymer is then heated and pressed into the PDMS molds to produce laminar microstructure components of interest.

The first layer is then delaminated onto a separate surface, such as glass, using heat-assisted microtransfer molding. Subsequent layers of the final structure are then assembled using a layer-by-layer sintering process under microscopic alignment to produce a large array of microstructures. This process draws on elements from existing technology, including laminated object manufacturing, microfabrication-based surface patterning, and thermal bonding of PLGA, to create polymeric microdevices with well-defined geometry.

2. Layer-by-Layer Alignment and Sintering

To ensure high-fidelity microdevice fabrication, a technique to align layers during sintering with high precision is used. In some embodiment, this approach uses a photomask aligner (MA4, Karl Suss, Sunnyvale, CA) retrofitted with a Peltier heater, temperature controller, relay, and voltage source to enable simultaneous alignment and thermal bonding. The mask holder vacuum is applied to hold a glass slide containing the first microstructure layer facing down while the next layer, still in the PDMS mold, is held on the wafer chuck. After optically aligning adjacent features using the mask aligner's microscope and alignment knobs, the layers are brought into contact and heated to just above the polymer's glass transition temperature for up to 3 minutes. The sealing process is continuously monitored during this time by observing the disappearance of light diffraction patterns As two layers came into contact, the small air gap between them produces diffraction that resolves when the heated polymer flows to close the gap. After cooling samples to room temperature, the PDMS micromold containing the second layer is peeled off to yield a multi-layered microstructure. Individual microdevices are then removed from the glass slide.

3. Filling and Capping

The micromolded microdevice shells/bases are filled prior to sealing using a BioJet Ultra ink jet piezoelectric nozzle that can rapidly dispense picoliter volumes of a drug or other agent into a microdevice compartment. To seal the filled devices, a cap mold is aligned, sealed with the shell/base, and delaminated. The resulting array of compartment-shell devices is then removed from the base and stored until use.

4. Removing Scrum

In some cases, the polymer used to fill the micromolds forms a "scrum" at the top which should be removed before capping.

V. Methods of Use

Methods of using the microdevices, and compositions or formulations thereof are also described. In some embodiments, the microdevices including one or more agents are used to treat cancer. In other embodiments, the microdevices including one or more agents are used to treat immune diseases. In other embodiments, the microdevices including one or more agents are used to treat a disease or disorder in which modulating the STING pathway is beneficial. The methods typically include administering to a subject in a need thereof an effective amount of a composition including microdevices and one or more active agents to modulate an immune response and/or inflammatory response, e.g., to reduce immunosuppression with the tumor microenvironment, and/or increase and anti-tumor response. The compositions are preferably administered locally including, but not limited to, via subcutaneous, intratumoral, and intramuscular injections. In some embodiments, upon release from the microdevices, the incorporated agent(s) can distribute systemically.

In some embodiments, the methods include locally administering to a subject in need thereof an effective amount of a composition including microdevices and one or more active agents to induce a local or systemic immune response and/or inflammatory response in the subject, to induce or increase STING pathway activity in the subject, to induce or increase the secretion of type I IFNs and/or an interferon response in the subject, to induce infiltration into the tumor microenvironment (e.g., by lymphocytes, basophils, macrophages, and/or dendritic cells), and/or to reduce immunosuppression within the tumor microenvironment.

In some embodiments, the subject to be treated is a human. In some embodiments, the compositions are administered by injection using a regular needle and completely degrade over time (and thus do not require removal). These features are believed to be advantageous for patient compliance.

All the methods described can include the step of identifying and selecting a subject in need of treatment, or a subject who would benefit from administration with the compositions.

A. Methods of Treatment

1. Treatment of cancer

In preferred embodiments, the compositions are used in methods of treating cancer. Preferably, the compositions are administered locally (e.g., via injection directly at a site of interest such as a tumor). Such methods include administering to the subject the compositions (e.g., via intratumoral injection) in an effective amount to treat and/or alleviate one or more symptoms associated with cancer. Typically, the methods induce immunogenicity and/or induce or increase an anti-tumor immune response.

In some embodiments of the method of treating cancer in a subject, the method involves administering to the subject a therapeutically effective amount of the compositions, wherein the composition is capable of up-regulating a STING-mediated immune response in the subject, thereby enhancing the tumor targeting of the subject's immune system. The composition is administered intra-tumorally to the subject.

Also provided herein are methods of preventing metastasis of cancer in a subject. The method comprises administering to the subject a therapeutically effective amount of the compositions to prevent one or more tumors at one location in the subject from promoting the growth of one or more tumors at another location in the subject. In some embodiments, the composition is administered intratumorally in a first tumor in one location to prevent metastasis of one or more tumors at a second location.

Administration of the compositions can reduce cancer cell proliferation or viability, increase apoptosis within a tumor, and/or reduce tumor burden in the subject. In some embodiments, the tumor growth (e.g., tumor volume or weight) is reduced by at least about 5%, at least about 10%, at least about 20%, at least about 30%, at least about 40%, at least about 50%, at least about 60%, at least about 70%, at least about 80%, at least about 90%, or about 100% compared to a reference (e.g., tumor growth in a corresponding subject after administration of free STING agonist or tumor growth in an untreated subject).

In some embodiments, the subjects to be treated have been diagnosed with stage I, stage II, stage III, or stage IV cancer.

Cancers to be Treated

Cancer is a disease of genetic instability, allowing a cancer cell to acquire the hallmarks proposed by Hanahan and Weinberg, including (i) self-sufficiency in growth signals; (ii) insensitivity to anti-growth signals; (iii) evading apoptosis; (iv) sustained angiogenesis; (v) tissue invasion and metastasis; (vi) limitless replicative potential; (vii) reprogramming of energy metabolism; and (viii) evading immune destruction (*Cell.*, 144:646-674, (2011)).

Tumors which may be treated in accordance with the methods are classified according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The methods can be used to treat solid tumors. The term "solid tumor" refers to an abnormal mass of tissue that usually does not contain cysts or liquid areas. Solid tumors may be benign or malignant. Different types of solid tumors are named for the type of cells that form them. Examples of solid tumors include but are not limited to, sarcomas, carcinomas, and lymphomas. Examples of solid tumor cancers include, but are not limited to, colon, breast, gastric, ovarian, lung, cervical, melanoma, renal, prostate, lymphoma, neuroblastoma, pancreatic and bladder cancers. Exemplary cancers that can be treated include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers.

In some preferred embodiments, the cancer/tumor to be treated is a hard-to-reach cancer/tumor or a cancer/tumor that is less amenable to multiple invasive procedures or injections (e.g., pancreatic cancer, brain cancer such as glioma or Glioblastoma multiforme). In preferred embodiments, the cancer is melanoma, cervical cancer, breast cancer, ovarian cancer, prostate cancer, pancreatic cancer, kidney cancer, liver cancer, testicular cancer, urothelial carcinoma, bladder cancer, lung cancer (e.g., non-small cell lung cancer, small cell lung cancer), sarcoma, colorectal adenocarcinoma, gastrointestinal stromal tumors, gastroesophageal carcinoma, colorectal cancer, hepatocellular cancer, malignant mesothelioma, leukemia, lymphoma, multiple myeloma, transitional cell carcinoma, neuroblastoma, plasma cell neoplasms, Wilm's tumor, or hepatocellular carcinoma.

More particular examples of cancers include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as, but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, and carcinosarcoma. For a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

2. Other uses

Because STING agonists modulate the innate immune response, STING agonists can be used as a therapeutic strategy for the treatment or prevention of other diseases, such as viral infections. For example, STING agonist has been shown to potentiate the immune response of flu vaccines (Wang J., et al., *Science,* 367(6480). pii: eaau0810. (2020)). Wang et al., show that the use of cGAMP as an adjuvant vigorously augmented influenza vaccine-induced humoral and $CD8^+$ T cell immune responses in mice by simulating the early phase of viral infection without concomitant excess inflammation. Thus, the compositions enclosing one or more STING agonists could be used as a vaccine adjuvant.

Methods of treating an infectious disease (e.g., flu) in a subject in need thereof include administering to the subject an effective amount of any of the compositions. In some embodiments, administration of the composition is capable of up-regulating a STING-mediated immune response (e.g., type I interferon) in the subject. Methods of vaccinating a subject against an infectious agent by administering to the subject an effective amount of any of the compositions have been developed, as well as methods of improving or increasing a humoral and/or cellular immune response to an antigen in a subject in need thereof, by administering to the subject an effective amount of any of the compositions. Methods of improving or increasing vaccine-induced humoral and/or cellular (e.g., $CD8^+$ T cell) immune responses in a subject in need thereof, include administering to the subject an effective amount of any of the compositions (e.g., a pharmaceutical composition including microdevices encapsulating one or more STING agonists). Preferably, the vaccine is a flu (i.e., influenza) vaccine.

B. Effective Amounts

Dosage and dosing regimens are dependent on the severity and location of the disorder or injury and/or methods of administration, and is known to those skilled in the art. The effective amount or therapeutically effective amount can be a dosage sufficient to treat, inhibit, or alleviate one or more symptoms of a disease or disorder, or to otherwise provide a desired pharmacologic and/or physiologic effect, for example, reducing, inhibiting, or reversing one or more of the underlying pathophysiological mechanisms underlying a disease or disorder such as cancer. For example, a therapeutically effective amount of the microdevice compositions used in the treatment of cancer is typically sufficient to reduce or alleviate one or more symptoms of cancer in a subject. In some embodiments, the subjects are mammals, most preferably, humans.

Symptoms of cancer may be physical, such as tumor burden, or biological such as proliferation of cancer cells. Accordingly, the amount of composition can be effective to, for example, kill tumor cells or inhibit proliferation or metastasis of the tumor cells. Preferably the composition including microdevices encapsulating one or more active agents, for example immunomodulatory agents (e.g., STING agonist), are preferentially delivered to cells in and around tumor tissues, for example cancerous cells or immune cells associated with tumor tissues (e.g. the tumor microenvironment) locally, for example by intratumoral injection. In some embodiments, the agents do not target or otherwise modulate the activity or quantity of healthy cells not within or associated with tumor tissues, or do so at a reduced level compared to cancer or cancer-associated cells. In this way, by-products and other side effects associated with the compositions are reduced, preferably leading directly or indirectly to cancer cell death. In some embodiments, the therapeutic and/or diagnostic agent directly or indirectly reduces cancer cell migration, angiogenesis, immune escape, radioresistance, or a combination thereof. In some embodiments, the agent directly or indirectly induces a change in the cancer cell itself or its microenvironment that reduces immunosuppression or induces activation of an immune response against the cancer cells. For example, in some embodiments, the composition is administered in an effective amount to enhance and/or prolong the activation, proliferation, and/or function of T cells (i.e., increasing tumor-specific proliferation of T cells, enhance cytokine production by T cells, stimulate differentiation, stimulate effector functions of T cells and/or promote T cell survival).

In some in vivo approaches, the compositions are administered to a subject in a therapeutically effective amount to reduce tumor size. In some embodiments, an effective amount of the composition is used to put cancer in remission and/or keep the cancer in remission. Also provided are effective amounts of the compositions to reduce or stop cancer stem cell proliferation.

The amount of a composition administered can be expressed as the amount effective to achieve the desired effect in the recipient. For example, in preferred embodiments, the microdevices including one or more STING agonists are administered in an amount effective to induce/enhance expression of interferon stimulated genes, inhibit or reduce cancer cell proliferation and/or viability, inhibit tumor growth, reduce tumor size, reduce tumor burden, to induce/enhance infiltration by lymphocytes (e.g., CD8+ and/or CD4+ T cells), natural killer cells, dendritic cells, basophils, and/or macrophages into the tumor or tumor microenvironment, improve response to immune checkpoint blockade, induce immunological memory that protects against tumor re-challenge, and/or improve cancer patient survival.

The actual effective amounts of the compositions can vary according to factors including the specific active agent administered, the particular composition formulated, the mode of administration, and the age, weight, condition of the subject being treated, as well as the route of administration and the disease or disorder (e.g., and the type, stage, and location of a cancer/tumor to be treated). Thus, it is not possible to specify an exact amount for every therapeutic composition. However, an appropriate amount can be determined by one of ordinary skill in the art using only routine experimentation given the teachings herein. For example, effective dosages and schedules for administering the therapeutics may be determined empirically, and making such determinations is within the skill in the art. The dosage ranges for the administration of the compositions are those large enough to affect the desired response. For example, the dosage ranges for the administration of the compositions are those large enough to affect reduction in cell proliferation or viability in target cancer cells or to reduce tumor burden for example.

The dosage should not be so large as to cause adverse side effects, such as unwanted cross-reactions, anaphylactic reactions, and the like. The dosage can be adjusted by the individual physician in the event of any counter-indications. It will also be appreciated that the effective dosage of the composition used for treatment may increase or decrease over the course of a particular treatment. Changes in dosage may result and become apparent from the results of diagnostic assays.

In certain embodiments, a subject is administered a composition having about micrograms, milligrams, μg/kg, micrograms/kg/minute, mg/kg/min, micrograms/kg/hour, or mg/kg/hour, or any range derivable therein of one or more therapeutic and/or diagnostic agent (e.g., STING agonist). Exemplary dosages of STING agonist include between 1 μg and 3 mg, such as about 1 μg to 10 μg, 10 μg to 50 μg, 50 μg to 100 μg, 100 μg to 500 μg, 500 μg to 1 mg, 1 mg to 2 mg, and 1 mg to 3 mg. Preferred ranges include between about 100 μg and 500 μg, between 500 μg and 1 mg.

Preferred dosing and release schedules for using the STING agonist compositions and methods for the treatment of cancer are discussed in more detail below, and exemplified in the working examples. However, in general, the timing and frequency of administration can be adjusted to balance the efficacy of a given treatment. Preferably, the methods involve a single administration. However, in some embodiments two or more administrations can be used, e.g., depending on the length of time for which treatment is desired. Exemplary dosing frequencies include single and multiple administrations such as hourly, daily, weekly, monthly or yearly dosing, or every other day, two days, three days, four days, five days, or six days. In some embodiments, dosages are administered about once or twice every week, every two weeks, every three weeks, or every four weeks. In some embodiments, dosages are administered about once or twice every month, every two months, every three months, every four months, every five months, or every six months.

It will be understood by those of ordinary skill that a dosing regimen can be any length of time sufficient to treat the disease or disorder in the subject. In some embodiments, the regimen includes one or more cycles of a round of therapy followed by a drug holiday (e.g., no drug). The drug holiday can be 1, 2, 3, 4, 5, 6, or 7 days; or 1, 2, 3, 4 weeks, or 1, 2, 3, 4, 5, 6, 7, 8, 9, 10, 11, or 12 months.

The microdevices allow for controlled release of incorporated agents. Particularly, the injectable formulations of polymeric microdevices release the enclosed agent(s) at two or more times, within a short period of time, and in the absence of agent leakage from the microdevices between releases.

The controlled release can be achieved by incorporating microdevices of different polymeric compositions (i.e., two or more different populations of microdevices) in one formulation. The controlled release can also be achieved from the geometric design of the microdevices. For example, in the microdevices having a compartment, the agent is enclosed in the compartment, where it is stable and protected from the external environment. It is also prevented from leaking from the microdevice until the microdevice shell is degraded. Once the shell is degraded, the release is rapid (e.g., for PLGA microdevices, complete release of the agent can be achieved within hours to days in vitro or in vivo). The rapid release may be characterized by releasing substantially all of the enclosed agent within a short period of time, such as within an hour, hours, a day, or a week. Unlike solvent evaporation microencapsulation, where the agent is incorporated with the polymer into a microsphere, the formulations provide de-coupling of device loading and release kinetics.

The microdevices also display no measurable leakage of the agent between bursts of release. No measurable leakage may be characterized by less than 10%, 9%, 8%, 7%, 6%, 5%, 4%, 3%, 2%, 1%, or less than 0.5% of the total agent released prior to the burst release. No measurable leakage may also be characterized by undetectable amounts of agent released prior to the burst release.

The formulations display rapid release after material-dependent delay. The delay in agent release is dependent on the shell thickness in the compartment-shell device, on shell polymer composition, on the geometry of the compartment-shell device, and other factors.

By combining microdevices of various polymer compositions, compartment-shell geometry, or microdevice size, the pulsatile release of the agent(s) can be tailored to a desired controlled release regimen. This dosing regimen advantageously mimics and simplifies dosing schedules typically requiring repeated administrations of the agent(s). Typical dosing schedules for STING agonists in clinical trials include:

(a) intratumoral administration on days 1, 8 and 15 of each 21-day cycle for cycles 1, 2 and 3 and then on day 1 of each 21-day cycle for cycles 4 and beyond for up to 35 cycles (up to approximately 2 years) (see ClinicalTrials.gov Identifier: NCT03010176);

(b) intratumoral administration on day 1 of each 21-day cycle for up to 35 cycles, then days 1 and 8 of each 21-day cycle for two cycles, then day 1 of each 21 day cycle up to 35 cycles, then days 1, 8 and 15 of each 21-day cycle for two cycles followed by day 1 of each 21-day cycle up to 35 cycles (see ClinicalTrials.gov Identifier: NCT03010176);

(c) intratumoral administration on days 1, 8 and 15 of each 28-day cycle with a starting dose of 50 micrograms (see ClinicalTrials.gov Identifier: NCT02675439);

(d) intratumoral administration on days 1 and 8 of each 21-day cycle with a starting dose of 200 micrograms (see ClinicalTrials.gov Identifier: NCT02675439);

(e) intramuscular or intratumoral administration on day 1 and day 22 of cycle 1 (see ClinicalTrials.gov Identifier: NCT03956680);

(f) IV infusion on days 1, 8, 15 and 22 on repeated 28-day cycles in escalating doses (0.3-14 µg/Kg of SB 11285; see ClinicalTrials.gov Identifier: NCT04096638); and (g) IV infusion on days 1, 8, 15 and 22 on repeated 28-day cycles in escalating doses (0.3-3.0 SB 11285 µg/Kg; see ClinicalTrials.gov Identifier: NCT04096638).

Thus, in some embodiments of the methods, microdevice formulations are administered locally (e.g., intratumorally) to achieve pulsatile release of the agent(s) (e.g., STING agonist), wherein the release of the agent(s) mimic any of the above dosing regimens but fewer, preferably only a single local administration of the microdevice composition is required relative to administration of soluble drug.

C. Combination Therapies and Procedures

The compositions can be administered alone or in combination with one or more conventional therapies, for example, a conventional cancer therapy. In some embodiments, the conventional therapy includes administration of one or more of the compositions in combination with one or more additional active agents. The combination therapies can include administration of the active agents together in the same admixture, or in separate admixtures. Therefore, in some embodiments, the pharmaceutical composition includes two, three, or more active agents. The additional active agent(s) can have the same, or different mechanisms of action. In some embodiments, the combination results in an additive effect on the treatment of the cancer. In some embodiments, the combinations result in a more than additive effect on the treatment of the disease or disorder.

The additional therapy or procedure can be simultaneous or sequential with the administration of the microdevice composition. In some embodiments the additional therapy is performed between drug cycles or during a drug holiday that is part of the composition dosage regime.

Combination therapy may be achieved by use of a single pharmaceutical composition that includes the therapeutic agents, or by administering two or more distinct compositions at the same or different time. The multiple therapies may be given in either order and may precede or follow the other treatment by intervals ranging from minutes to weeks. In embodiments where the other agents are applied separately, it is preferable to administer the therapies in time frames, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several days (e.g., 2, 3, 4, 5, 6, 7, 8, 9, 10, or more) to several weeks (e.g., 1, 2, 3, 4, 5, 6, 7, 8 or more) lapse between the respective administrations.

In some embodiments, the additional therapy or procedure is surgery, radiotherapy, chemotherapy, immunotherapy, cryotherapy or gene therapy. Immunotherapy includes, but is not limited to, administration of one or more STING agonists, one or more immune-checkpoint blockage agents, or a combination thereof. Exemplary immune-checkpoint blockage agents include, but are not limited to, an antibody or antigen-binding fragment thereof, such as an antibody or antigen-binding fragment thereof that is an inhibitor of CTLA-4, PD-1, PD-L1, PD-L2, TIM-3, LAGS, or a combination thereof, such as Pembrolizumab (anti-PD1 mAb), Durvalumab (anti-PDL1 mAb), PDR001 (anti-PD1 mAb), Atezolizumab (anti-PDL1 mAb), Nivolumab (anti-PD1 mAb), Tremelimumab (anti-CTLA4 mAb), Avelumab (anti-PDL1 mAb), Ipilimumab (anti-CTLA4 mAb), and RG7876 (CD40 agonist mAb), and any of those specifically introduced above or otherwise mentioned herein.

In some embodiments, the compositions and methods are used prior to or in conjunction with an immunotherapy, such as adoptive T cell therapy, and/or a cancer vaccine.

Additional therapeutic agents that are suitable for used in combination therapy include conventional cancer therapeutics such as chemotherapeutic agents, cytokines, and chemokines, including, but not limited any of those specifically introduced above or otherwise mentioned herein.

In some embodiments, the compositions and methods are used prior to or in conjunction with surgical removal of tumors, for example, in preventing primary tumor metastasis. In some embodiments, the compositions and methods are used to enhance the body's own anti-tumor immune functions.

VI. Kits

The microdevices and formulations and other materials can be packaged together in any suitable combination as a kit useful for performing, or aiding in the performance of, the methods. It is useful if the kit components in a given kit are designed and adapted for use together in the method. For example, kits with one or more dosages packed for injection into a subject, may include a pre-measured dosage of a microdevice formulation in a sterile needle, ampule, tube, container, or other suitable vessel. The kits may include instructions for dosages and dosing regimens.

The present invention will be further understood by reference to the following non-limiting examples.

Examples

The Examples show demonstrate development and use of a multidose drug delivery platform through engineering polylactic-co-glycolic acid (PLGA), an FDA-approved and commercially available polymer, into cubic microdevices (FIG. 1A). Unlike commonly used local drug delivery materials, such as hydrogels or microdevices produced using a double emulsion-solvent evaporation technique, which exhibit sustained drug release kinetics (see Kamaly N., et al., Chem Rev., 116(4):2602-63(2016); Li J. and Mooney D J, Nat Rev Mater., 1(12). pii: 16071 (2016); Lin C C. and Anseth K S., Pharm Res., 26(3):631-43 (2009); Wang H. and Mooney D J, Nat Mater., 17(9):761-772 (2018)), these microfabricated PLGA microdevices (PLGA-MPs) release individual doses of incorporated STING agonist in pulses up to several months with essentially no leakage. The Examples show that in several tumor models, a single injection containing multiple populations of STING agonist-loaded PLGA-MPs inhibits tumor growth and improves survival as effectively as multiple injections of soluble STING agonist. The ability to combine multiple doses into single injection PLGA-MPs also decreases metastasis and expands the potential applications of current STING agonist-based therapy to hard-to-reach tumors. This is the first demonstration of an injectable and fully degradable drug delivery platform that can mimic the kinetics of multiple injections for effective cancer immunotherapy.

Example 1: Fabrication of PLGA Microdevices with Different Release Kinetics

Materials and Methods
Microdevice Fabrication

PLGA was purchased from Evonik (Germany) and PolySciTech (West Lafayette, IN). PLGA microdevices were fabricated through the Stamp Assembly of Polymer Layers (SEAL) process (McHugh K J., et al., Science, 357(6356): 1138-1142 (2017)). Photomasks with microscale patterns of bases and caps were made by Front Range Photomask (Palmer Lake, CO). Positive master molds of microdevice base and cap were created by SU-8 lithography on silicon wafers. The mixture of PDMS base and curing agent (Sylgard 184, Dow Corning, Midland, Michigan) were then poured onto the silicon master mold following with high vacuum for 1 h. A glass slide with two cover slips at each end was then pushed against the silicon mold while curing in the oven for 2 h at 150° C. to yield a thin PDMS mold. The obtained PDMS molds were then used as negative molds to press desired microdevices. PLGA films were prepared by solvent casting 60% weight/volume PLGA in acetone solution. The thickness of PLGA films were ~1650-1750 µm. For molding the cap of the microdevices, a small piece of PLGA film was placed between the PDMS cap mold and a Teflon film, and covered with a glass slide. A pair of spring-loaded clamps was then used to fix and compress the microdevices in a 120° C. vacuum oven for 2 h. PLGA film melted and flowed in the cap PDMS mold during heating. The setup was then allowed to cool down to room temperature and separated to yield the PLGA caps in the PDMS mold. For molding the base of the microdevices, the above steps were repeated without using the Teflon film. Therefore, the PLGA base will separate from PDMS base mold and stick to the covering glass slide. The cargos of interest were filled into the PLGA microdevices using a BioJet Ultra picoliter dispensing instrument (Biodot, CA). The aqueous solutions of cargos were dispensed for multiple 15-drop cycles of 180-200 µL drops. Filled microdevices were then aligned and sintered with corresponding PLGA caps using a photomask aligner (MA4, Karl SUSS, Sunnyvale, CA) retrofitted with a Peltier heater to enable simultaneous alignment and sealing. Sealed microdevices were then separated from glass slide using a razor blade. SEM images were collected using a JSM-5600LV SEM (JEOL, Tokyo, Japan) with an acceleration voltage of 5 kV. High resolution X-ray CT image was collected at the Biotechnology Resource Center of Cornell University.

Results

Figure 1B:
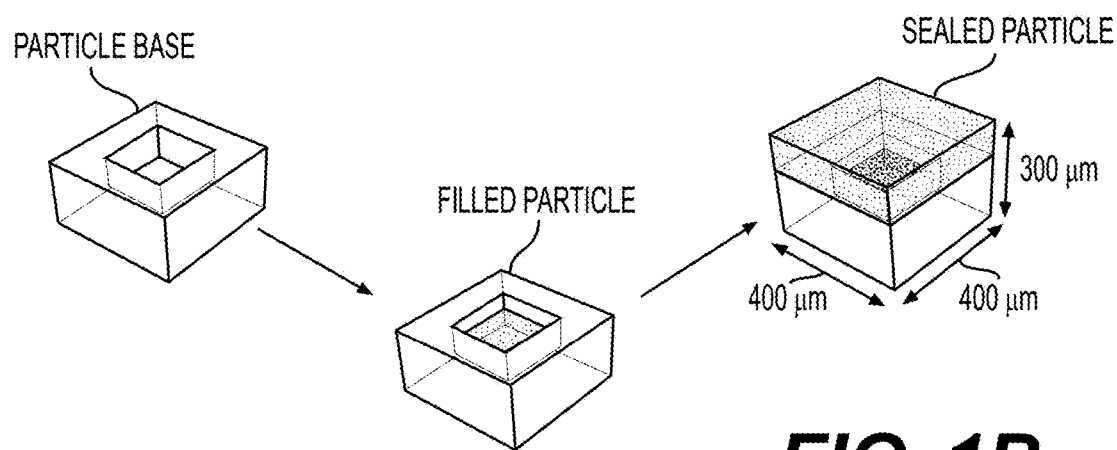
Figure 1C:
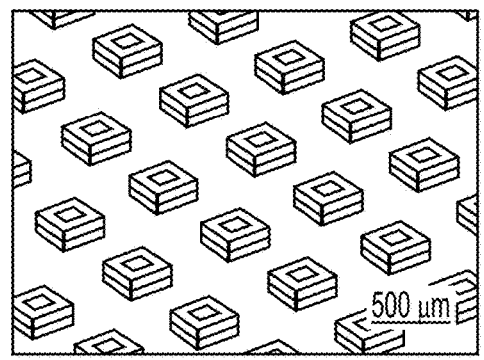
Figure 1D:
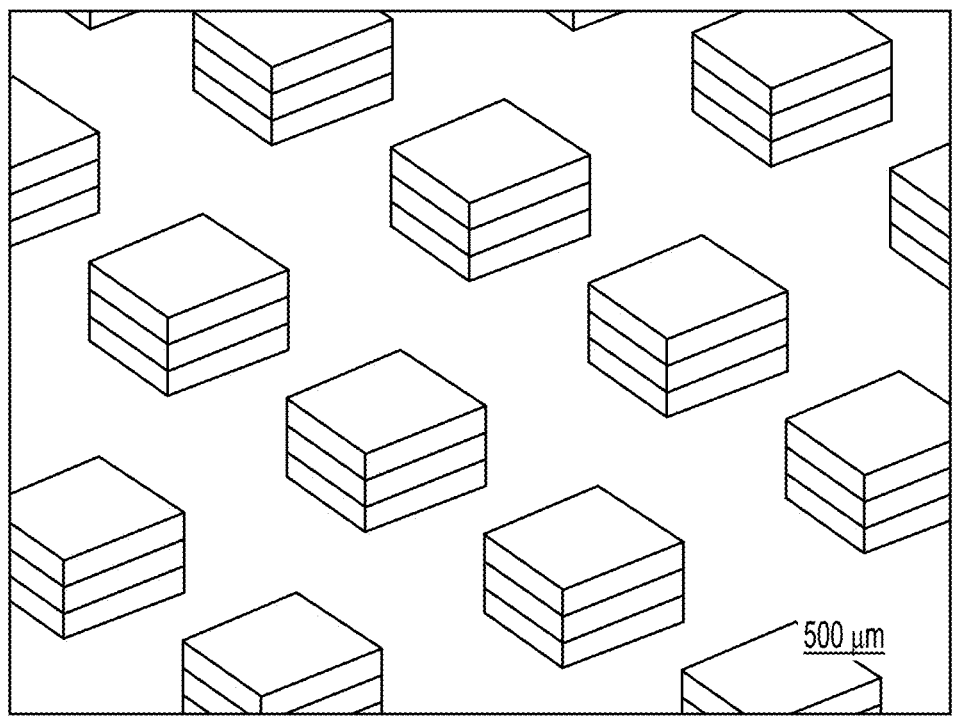
Figure 1E:
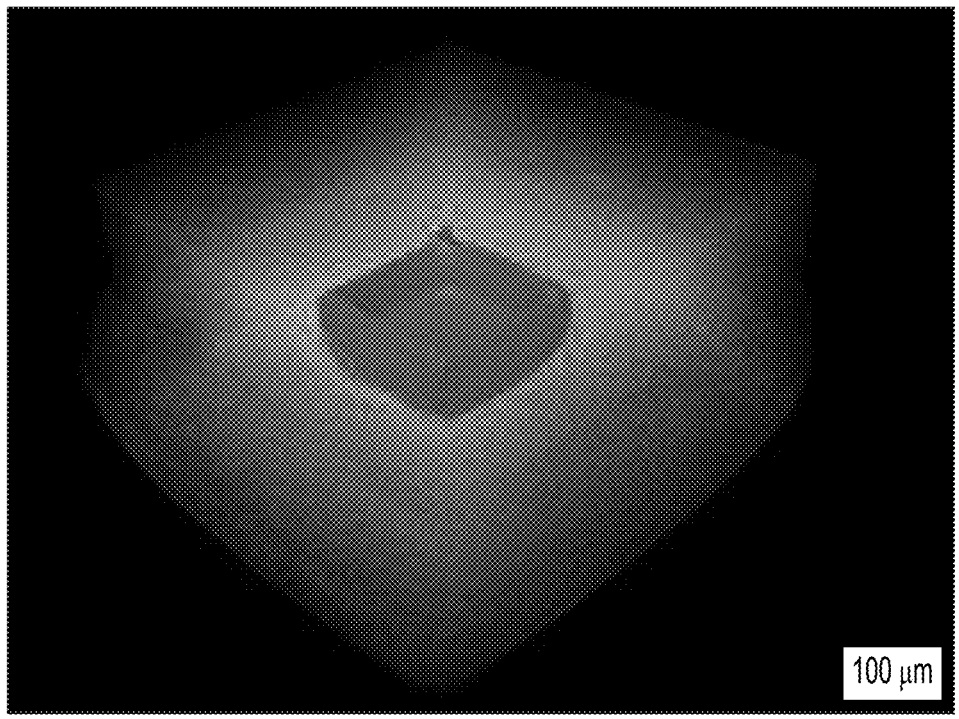

Soft lithography techniques were utilized to fabricate arrays of cubic PLGA microdevices with a fully enclosed cavity for drug loading (FIG. 1B). Briefly, PLGA was heated and pressed into a polydimethylsiloxane (PDMS) mold to form microdevice bases with internal cavities (200×200× 100 µm by length×width×height), which corresponds to a volumetric capacity of 4 nL. Aqueous drug or model drug was then filled into bases using a piezoelectric dispenser that can dispense volumes on the order of 100 picoliter (pL). The water component of the drug solutions evaporated rapidly due to the small volume, which provided space for filling additional cargo. Multiple filling and drying cycles were used to achieve maximum cargo loading. Filled microdevices were then aligned with PLGA caps embedded in a PDMS mold and sealed by heating above the glass transition temperature (approximately 50° C.) of PLGA. Sealed microdevices had external dimensions of 400×400×300 µm (length×width×height) and wall thickness of 100 µm in each dimension. The loading capacity of each microdevice was 8.4% by volume. Scanning electron microscopy (SEM), high resolution X-ray computed tomography (CT), and optical images showed that microdevices can be made in large arrays (over 300 per array) with high fidelity (FIGS. 1C-1D).

Example 2: PLGA Microdevices Exhibit Similar Release Kinetics In Vitro and In Vivo Materials and Methods
Microdevice Fabrication PLGA microdevices were fabricated as described in Example 1.

In Vitro Release Kinetics

To study the in vitro release kinetics, the following agents were obtained from the indicated vendors: AF647-dextran (Life Technologies, Carlsbad, CA), 3'3'-cGAMP (Invivogen, San Diego, CA), Cy5-CpG DNA (5'-TCC ATG ACG TTC CTG ACG TT-Cy5-3', IDT Inc. Coralville, Iowa), and pemetrexed (Sigma-Aldrich, MO). PLGA microdevices were separately filled with 1 μg of AF647-dextran, 2 μg of 3'3-cGMAP, 1 μg of Cy5-CpG, or 2 μg of pemetrexed, respectively. To determine the cargo loading in microdevices, filled microdevices were suspended in 200 μL of PBS buffer individually, vortexed for 15 seconds, and centrifuged at 14000 rcf for 1 minute. The supernatants were then analyzed by a microplate reader (AF647, AF647-dextran, Cy5-CpG), HPLC (pemetrexed) and Nanodrop™ (3'3'-cGAMP, absorbance at 260 nm). The results were quantified using a standard curve of a serial dilution of stock solutions. Filled microdevices were then sealed with corresponding PLGA caps. Each microdevice was placed into 200 μL of PBS (pH=6.84) in a 0.5 mL microcentrifuge tube (Eppendorf, Hamburg, Germany) and incubated on an orbital shaker at 37° C. The supernatant of each centrifuge tube was collected at predetermined time points. The supernatants of AF-647 dextran and Cy5-CpG groups were analyzed by a microplate reader (Tecan Infinite M200 spectrophotometer, excitation/emission=640/680 nm). The supernatants of 3'3'-cGAMP and pemetrexed were analyzed via HPLC (Alliance HPLC systems, Waters Co., MA, USA) using a C-18 column (Acclaim™ PolarAdvantage II, 3 μm, 4.6×150 mm) and a photodiode detector at 260 nm for 3'3'-cGAMP and 254 nm for pemetrexed. Water and acetonitrile were used as mobile phases. The results were quantified using a standard curve of a serial dilution of stock solutions and normalized to total cumulative release (n=6-8). The actual release day of each PLGA was determined as the day at which more than 50% of cargo was released.

In Vivo Release Kinetics

One PLGA microdevice encapsulating AF647-dextran (1 μg) was tip-loaded into an 18-gauge Monoject filter needle (Covidien, Dublin, Ireland) in approximately 20 μl of 15 mg/ml methyl cellulose (MC, Sigma Aldrich) used as a viscosity enhancer. Microdevices were then injected subcutaneously into the left and rear flanks (1 microdevice per side) of hairless mice (SKH1-E) or intratumorally into tumor-bearing mice. Mice were imaged every 1-2 days using a PerkinElmer Spectrum In vivo Imaging System (excitation/emission=640/700 nm, IVIS, Hopkinton, MA).

Cumulative release was normalized to the maximum and minimum total fluorescence in the region of interest corresponding to a particular microdevice's complete release and background signal, respectively. Because fluorescence dropped after release due to biological clearance, values after the highest signal were set to 100% in FIG. 2. Release timing was considered to be the day on which fluorescence achieved half of its final maximum value above background. To evaluate the amount of released cargo in tumors, 10 AF647-loaded PLGA-1 (0.5 μg AF647 per microdevice) were intratumorally injected into B16F10 tumor-bearing mice at day 0. Free cGAMP were also administered intratumorally at days 0 and 4 to control tumor growth. Four mice were euthanized and tumors and serum were isolated every day until day 7. The tumors were homogenized in PBS buffer. Unreleased AF647-PLGA-1 were physically broken to release AF647 during homogenization. The supernatant containing unreleased AF647 and serum sample were analyzed by a microplate reader (excitation/emission=640/680 nm).

Micro-CT Analysis of Microdevice Distribution

5% of phosphotungstic acid (PTA) was doped into PLGA-1 during making PLGA-1 films to increase the contrast for microCT imaging. PTA-doped PLGA-1 were intratumorally injected into B16F10 tumor-bearing mice. Mice were then euthanized 1 h post injection. The tumors were isolated and imaged by a Bruker Skyscan 1276 microCT imaging system. The reconstructed images were analyzed by MicroView.

Results

Figure 2A:
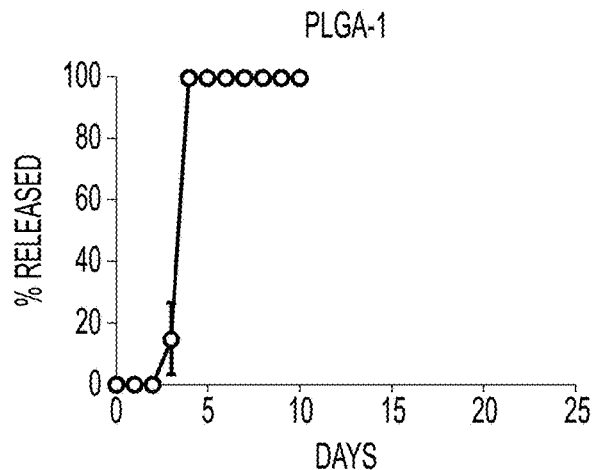
FIGS. 2A-2L illustrate quantification of release kinetics of PLGA-MPs.
Figure 2B:
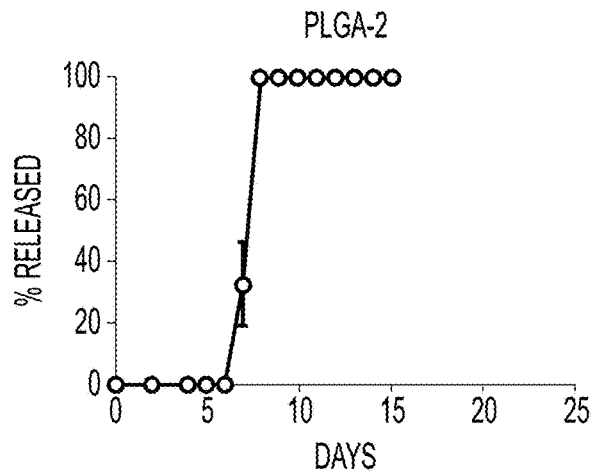
Figure 2C:
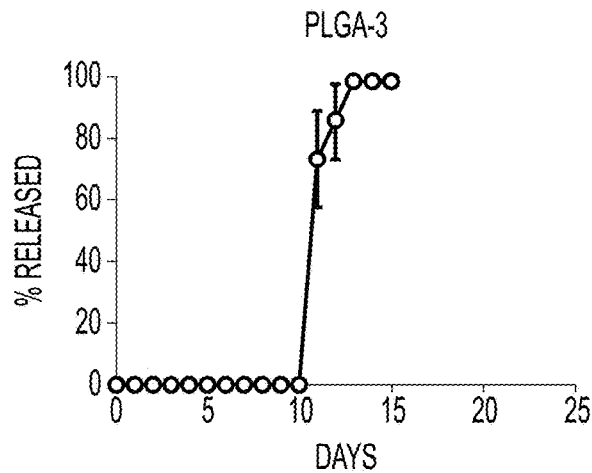
Figure 2D:
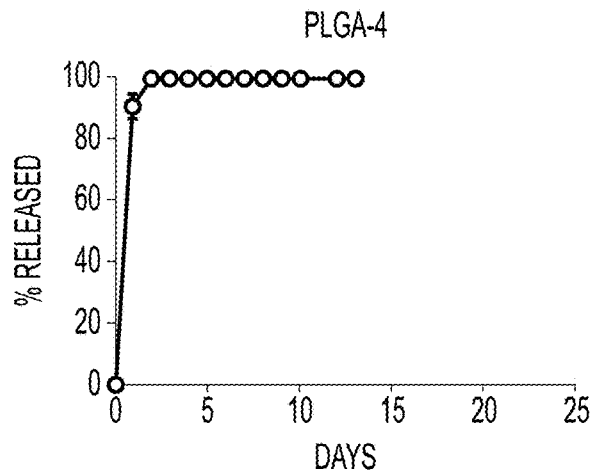
Figure 2E:
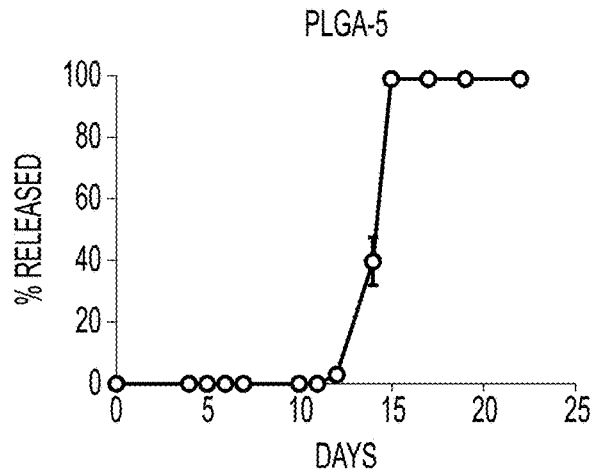
Figure 2F:
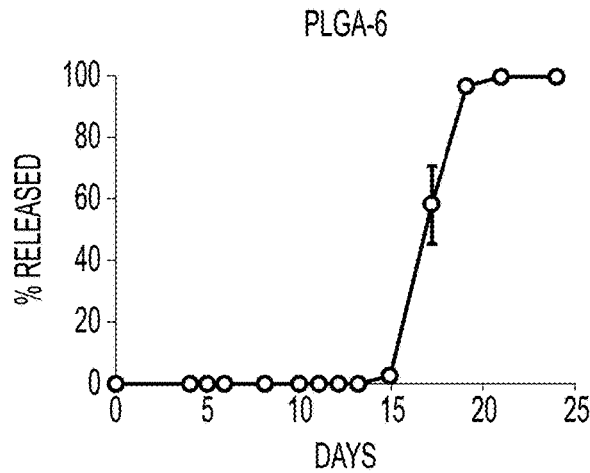
Figure 2G:
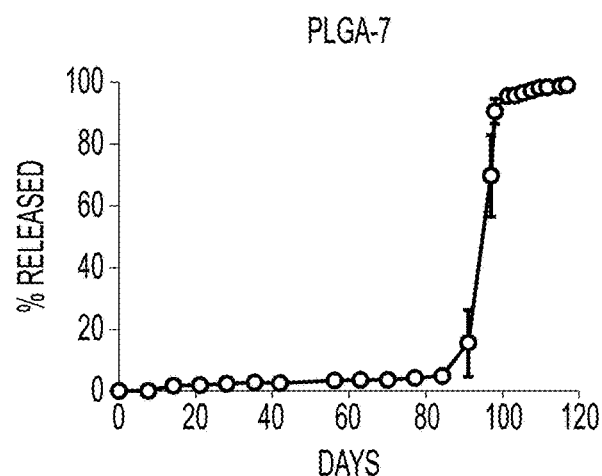
Figure 2H:
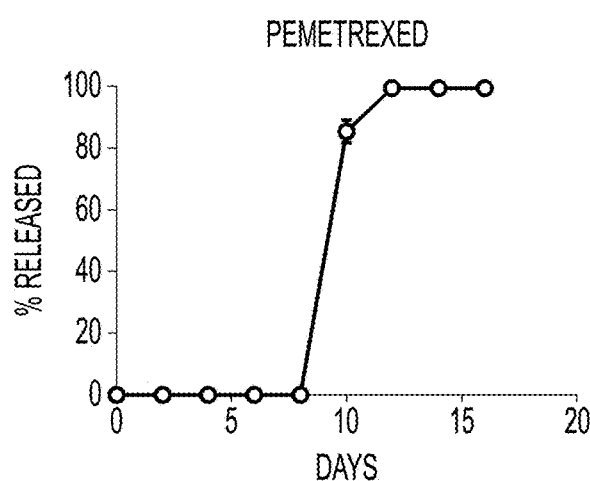
Figure 2I:
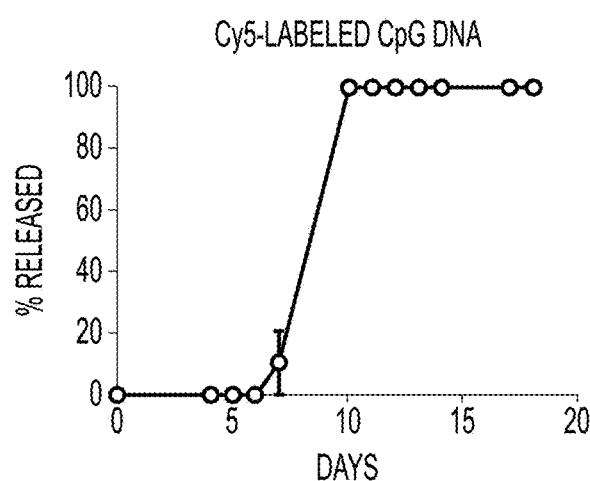
Figure 2J:
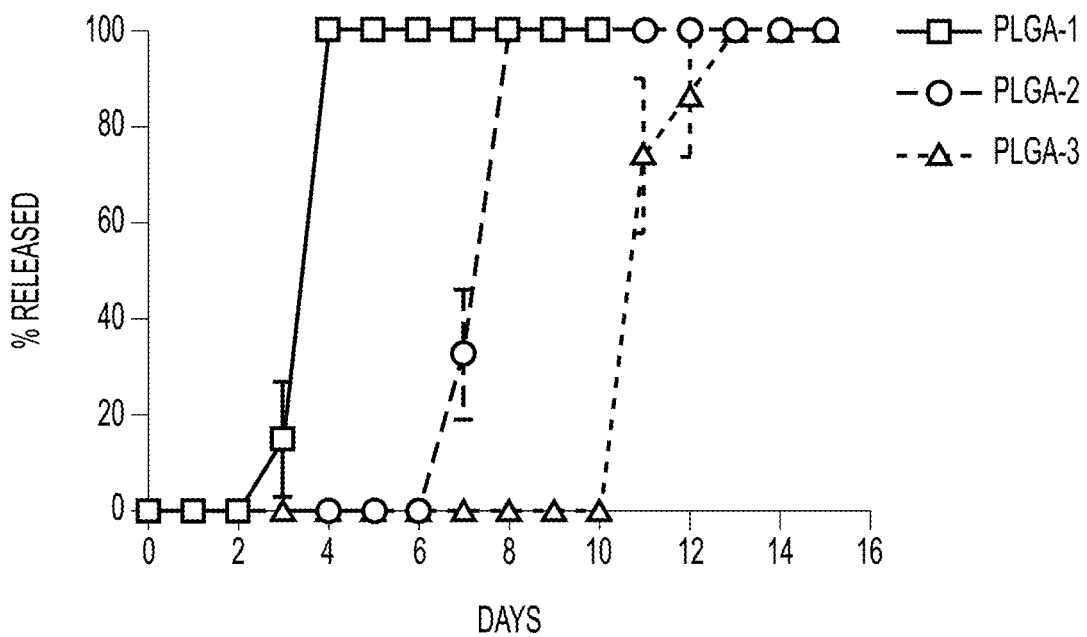
Figure 2K:
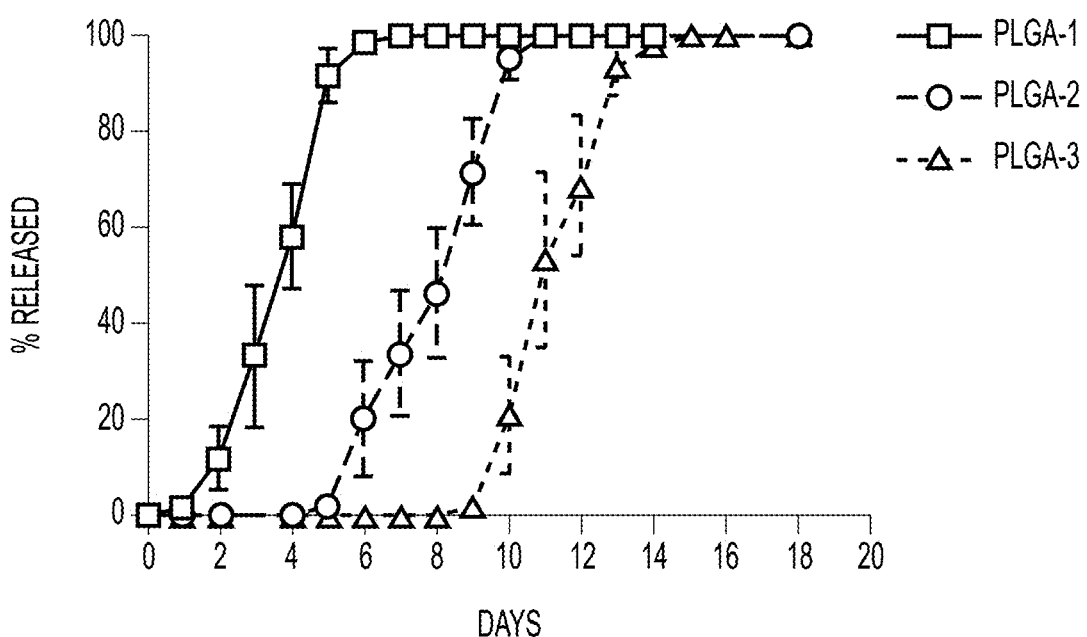

To study the release kinetics, PLGA microdevices with different polymer properties (Table 1) were filled with a fluorescently labeled macromolecule, Alexa Fluor 647-labeled dextran (AF647-dextran). These microdevices were sealed with corresponding caps and incubated in phosphate-buffered saline (PBS, pH=6.84) at 37° C. to mimic the acidic TME. PLGA microdevices released AF647-dextran in pulses at approximately 1±0, 4±0, 8±0, 11±1, 15±1, 18±1, and 97±2 days without detectable leakage prior to release (Table 1; FIGS. 2A-2G). To mimic the dosing regimen of four consecutive doses with 3 to 4 days between each dose that have been shown to be effective inhibiting tumor growth in animal models (Corrales L., et al., 2015), microdevices that release AF647-dextran at day 4 (PLGA-1), day 8 (PLGA-2), and day 11 (PLGA-3) were selected for further study (FIG. 2J). To validate the release kinetics in vivo, AF647-dextran-loaded PLGA-1, 2, and 3 microdevices were subcutaneously injected into hairless mice. The release of AF647-dextran was monitored by in vivo fluorescence imaging (IVIS). Released AF647-dextran showed an over 100-fold increase in fluorescence intensity compared to incorporated AF647-dextran due to the self-quenching effects of the fluorophore when dry or at an extremely high local concentration. Microdevices released AF647-dextran in vivo with similar release time as in vitro (FIG. 2K). The average releasing times of PLGA-1, 2, and 3 in vivo were 3.9±1.1, 8.1±1.5, 11.5±1.4 days, respectively.

TABLE 1

PLGA compositions and in vitro release time points of AF-647 dextran from different PLGA-MPs.

| Name | $M_n$ (kDa) | $M_w$ (kDa) | PDI | Chain end | Lactide: glycolide ratio | Release time (days) |
|---|---|---|---|---|---|---|
| PLGA-1 | 4.4 | 8.4 | 1.91 | acid | 50:50 | 4 ± 0 |
| PLGA-2 | 9.1 | 16.6 | 1.83 | acid | 50:50 | 8 ± 0 |
| PLGA-3 | 12.1 | 22.2 | 1.83 | acid | 60:40 | 11 ± 1 |
| PLGA-4 | 3.7 | 6.1 | 1.64 | acid | 50:50 | 1 ± 0 |
| PLGA-5 | 28.9 | 49.5 | 1.71 | acid | 50:50 | 15 ± 1 |
| PLGA-6 | 7.6 | 13.4 | 1.75 | ester | 50:50 | 18 ± 1 |
| PLGA-7 | 71.5 | 121.1 | 1.82 | ester | 75:25 | 97 ± 2 |

The molecular weight of PLGA was measured by a tetrahydrofuran gel permeation chromatography equipped with a light scattering detector (Malvern, UK). Data represent average±s.d. (n=6 to 8). Mn, Mw, and PDI represent number averaged molecular weight, weight averaged molecular weight, and polydispersity index, respectively.

Figure 2L:
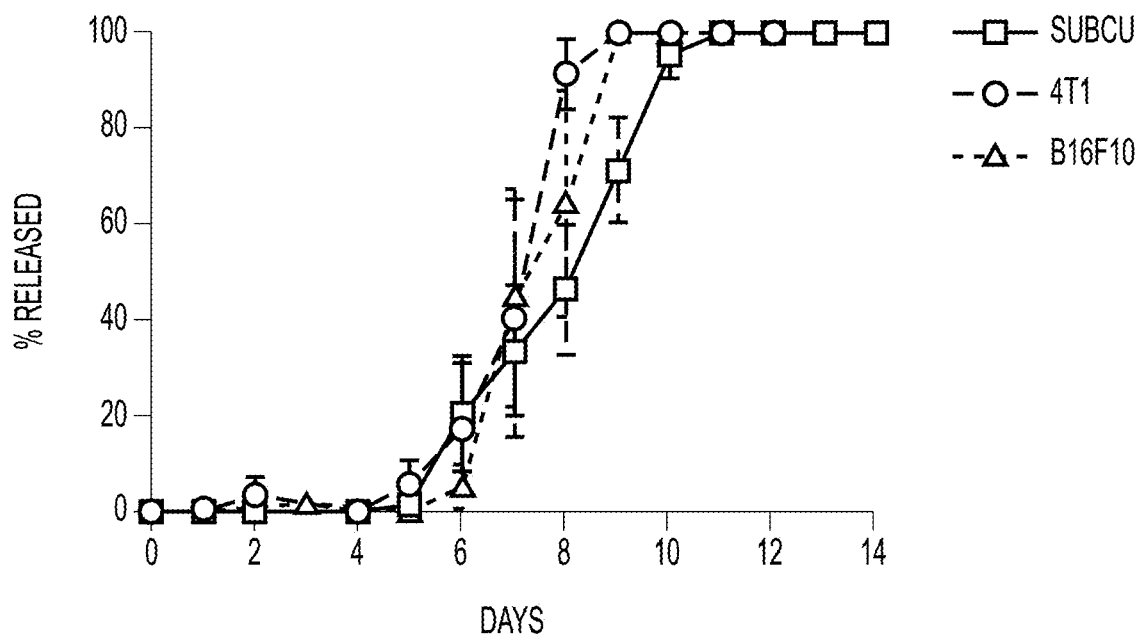
Figure 2M:
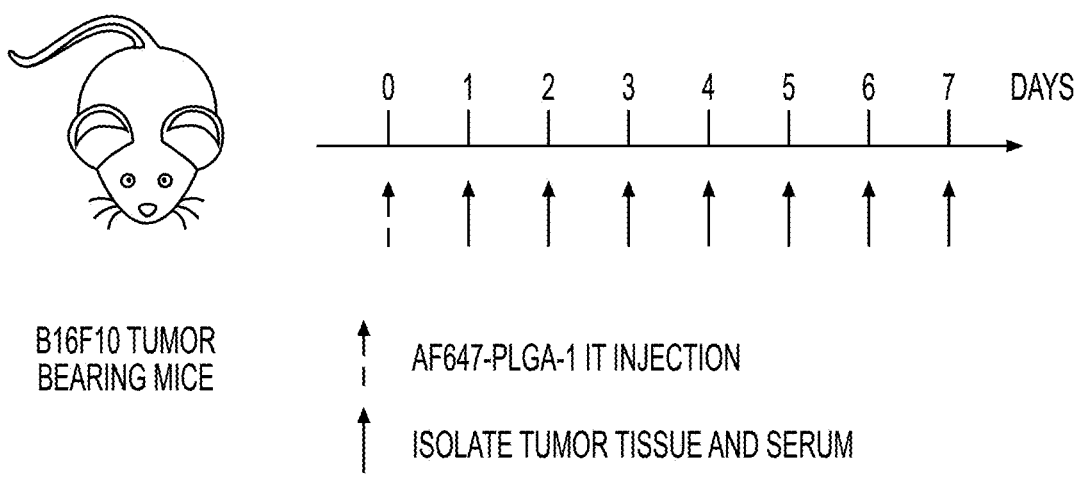
FIG. 2M is a schematic showing the treatment and sampling schedule of B16F10 tumor-bearing mice post intratumoral injections of AF647-loaded PLGA-1.
Figure 2N:
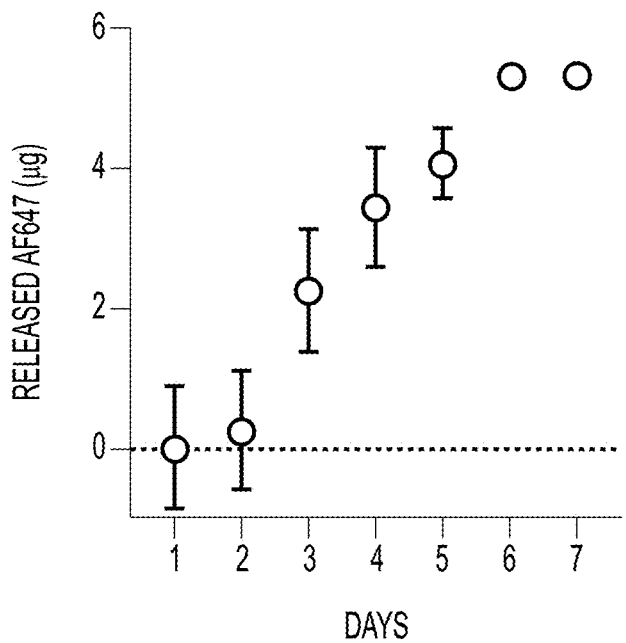
FIG. 2N is a graph showing cumulative in vivo release of AF647 from PLGA-1 in B16F10 tumors (n=4).
Figure 2O:
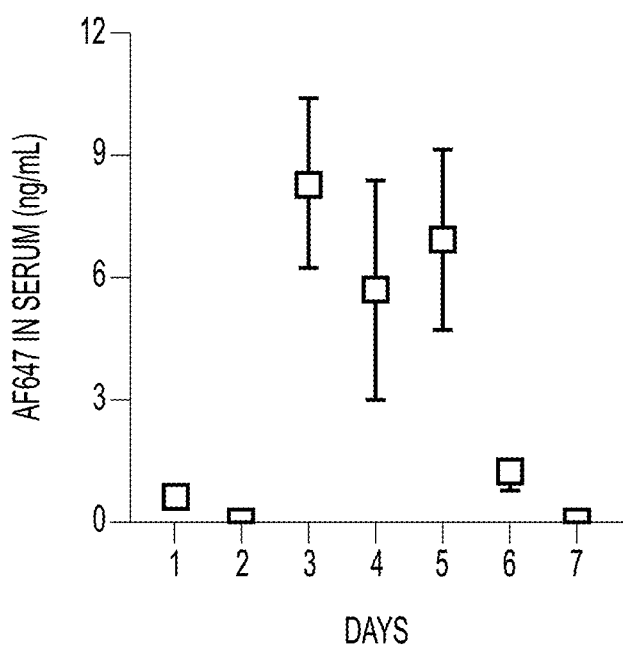
FIG. 2O is a graph showing AF647 concentration in serum after intratumoral injection of AF647-loaded PLGA-1 (n=4). Error bars represent s.e.m.

The influence of different TMEs on release kinetics was then evaluated. AF647-dextran-loaded PLGA-2 was intratumorally injected into mice bearing B16F10 or 4T1 tumors. Release kinetics were then monitored by daily IVIS imaging. PLGA-2 showed consistent release kinetics in both tumors and the subcutaneous environment (FIG. 2L). To study the distribution of microdevices in tumors, 5% phosphotungstic acid (PTA) was doped in PLGA-1 and the tumor was imaged using MicroCT. The microdevices were successfully injected into tumors and aggregated at the injection site due to the low mobility in confined environment. To further demonstrate that PLGA-MPs released all incorporated cargo during the release window, AF647-loaded PLGA-1 microdevices were fabricated and intratumorally injected into B16F10 tumor-bearing mice. AF647 is a small and hydrophilic molecule with a MW of 753.9, that is similar to that of cGAMP (MW of 675.1). Free AF647 was rapidly cleared from tumors after intratumoral injection (>95% within 2.5 hours). The amount of unreleased AF647 was measured in tumors every day and the amount of released AF647 was back-calculated (FIG. 2M). As shown in FIG. 2N, PLGA-1 completely released AF647 from 3 to 6 days in tumors. Some released AF647 also diffused into the blood stream as demonstrated by elevated AF647 concentration in serum from day 3 to 6 (FIG. 2O). These data demonstrated that PLGA-MPs released all incorporated cargos at anticipated time points in tumors.

Example 3: Single Injection of cGAMP-Loaded Microdevices Effectively Inhibited Tumor Growth Materials and Methods Microdevice Fabrication PLGA microdevices were fabricated as described in Example 1.

Release Kinetics

Release kinetics was evaluated as described in Example 2. For the sustained release systems, fast-dextran hydrogel kits (Part No. TURE2-1KT), fast-PVA hydrogel kits (Part No. TRUE4-1KT), and 3D collagen Kit (Part No. ECM675) were purchased from Millipore Sigma. 40 µg of cGAMP was loaded into 40 µL hydrogels according to the manufacturer's instructions. To study the in vitro release kinetics, cGAMP-loaded hydrogels were incubated on an orbital shaker at 37° C. The supernatant of each centrifuge tubes was collected at predetermined time points and analyzed by Nanodrop™.

Bioactivity of Released 3 '3'-cGAMP

To evaluate the activity of 3'3'-cGAMP after microdevice fabrication, cGAMP-loaded PLGA-2 were placed in PBS buffer and mechanically broken by a scalpel to release incorporated cargo. To evaluate the activity of cGAMP after release, cGAMP-loaded PLGA-2 were incubated on an orbital shaker in PBS buffer at 37° C. Supernatant was collected at release window and quantified by Nanodrop™. $5 \times 10^4$ RAW-Lucia™ ISG cells were plated in a 96-well plate. A serial dilution of cGAMP stock solutions, dissolved cGAMP after microdevice fabrication, and released cGAMP were incubated with cells for 24 h before adding QUANTI-Luc™ solution. The plate was then analyzed by a microplate reader. The results were quantified using a standard curve of a serial dilution of stock solutions.

Animals and Cell Lines

All animal procedures were approved by Massachusetts Institute of Technology Committee on Animal Care. Six to eight-week SKH1-E, C57BL/6, and BALB/c female mice were purchased from Charles River Laboratories Inc. The mouse breast cancer cell line 4T1 and melanoma cell line B16F10 were purchased from American Type Culture Collection. The RAW-Lucia™ ISG cell line was purchased from InvivoGen Inc. KPC (LSL-KrasG12D/+; LSL-Trp53R172H/+; Pdx-1-Cre) pancreatic cancer cells were kindly given by Dr. Serguei Kozlov (Frederick National Laboratory of Cancer Research). Cells were cultured in Dulbecco's modified Eagle medium (DMEM, B16F10), DMEM/F12 (KPC), and RPMI 1640 (4T1) supplemented with 10% fetal bovine serum (FBS), penicillin (100 units/ mL), and streptomycin (100 µg/mL) at 37° C. and with 5% CO2. RAW-Lucia™ ISG cells were cultured in DMEM supplemented with 2 mM L-glutamine, 10% FBS, 100 µg/ml Normocin™, and 200 µg/ml Zeocin™.

Treatment of B16F10 and 4T1 Tumors.

$2 \times 10^5$ 4 T1 or $2 \times 10^5$ B16F10 cells were subcutaneously injected to the right rear flank of BALB/c mice or C57BL/6 female mice respectively. For orthotopic 4T1 model, $2 \times 10^5$ 4 T1 cells were injected into the mammary fat pad. Seven days after tumor injection, B16F10 tumor-bearing mice were divided into 6 experimental groups (n=8 for each group): untreated, 1×empty microdevices(EP), 1×cGAMP-S plus EPs, 1×collagen gel, 4×cGAMP-S, and 1×cGAMP-S plus cGAMP-MPs, respectively (FIG. 3D). For the 4×cGAMP-S group, mice were intratumorally administered with 10 µg of cGAMP in 50 µL MC solution (cGAMP-S) at days 0, 4, 8, and 11 to replicate the four doses of soluble cGAMP. The overall does of cGAMP were 40 µg per mouse throughout the treatment period. For the 1×cGAMP-S+ cGAMP-MP group, mice were given a single intratumoral injection of a mixture of 10 µg cGAMP-S, 5 PLGA-1 microdevices containing 10 µg cGAMP, 5 PLGA-2 microdevices containing 10 µg cGAMP, and 5 PLGA-3 microdevices containing 10 µg cGAMP (40m total) in 50 µL MC solution via an 18G filter needle. For 1×EPs and 1×cGAMP-S+EPs groups, 5 each of empty PLGA-1, PLGA-2, and PLGA-3 microdevices with or without 40 µg cGAMP-S were injected intratumorally in 50 µL MC solution. Mice from untreated groups were injected intratumorally with 50 µL MC solution at day 7 post tumor inoculation. In the subcutaneous and orthotopic 4T1 models, tumor-bearing mice were subjected to untreated, 4×cGAMP-S, and 1×cGAMP-S+cGAMP-MPs treatments at day 7 post tumor inoculation (n=8 for each group). Tumor size was measured every other day starting at day 7 post tumor inoculation with a digital caliper. Tumor volume was calculated using the following formula: length (mm)×width$^2$ (mm)×0.5. Animals were euthanized when showing signs of poor health condition or when the tumor size exceeded 1500 mm$^3$.

Statistical Analysis

All statistical analyses were performed using the GraphPad Prism software package (PRISM 8.0.2; GraphPad Software, USA). Biological replicates were used in all experiments unless otherwise stated. Survival benefit was determined using a log-rank test. All experimental results were indicated as the mean±s.d. or the mean±s.e.m. One-way and two-way analysis of variance (ANOVA) were used when there were multiple comparisons.

Results

Figure 3A:
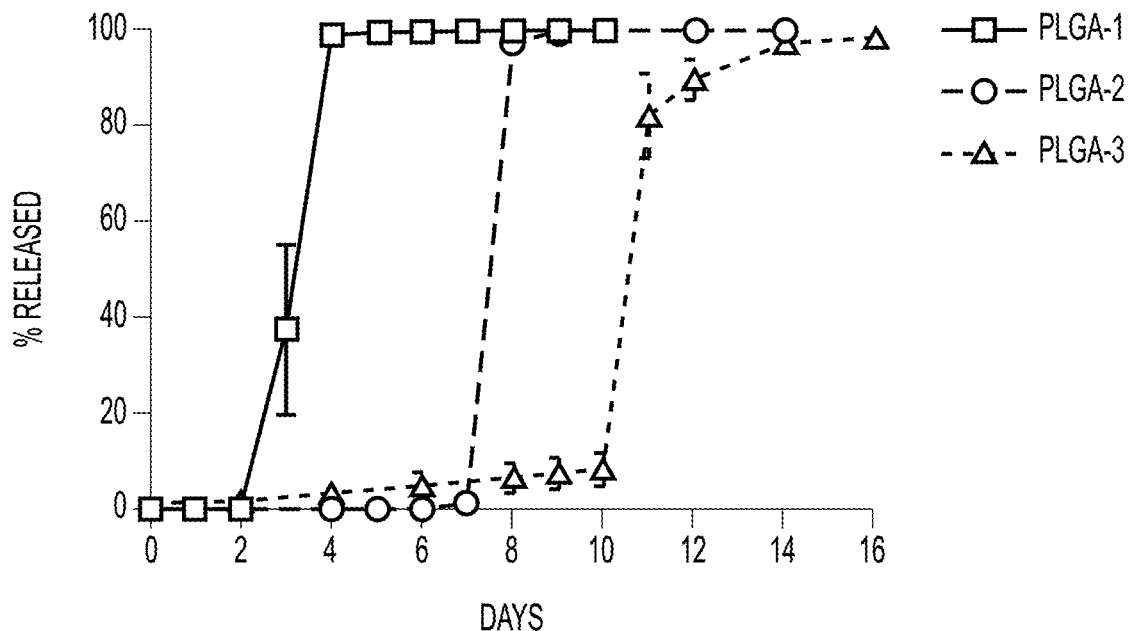
FIG. 3A is a graph showing the cumulative in vitro release of 3'3'-cGAMP from PLGA-1, 2, and 3 (n=6-8). Error bars represent s.e.m.
Figure 3B:
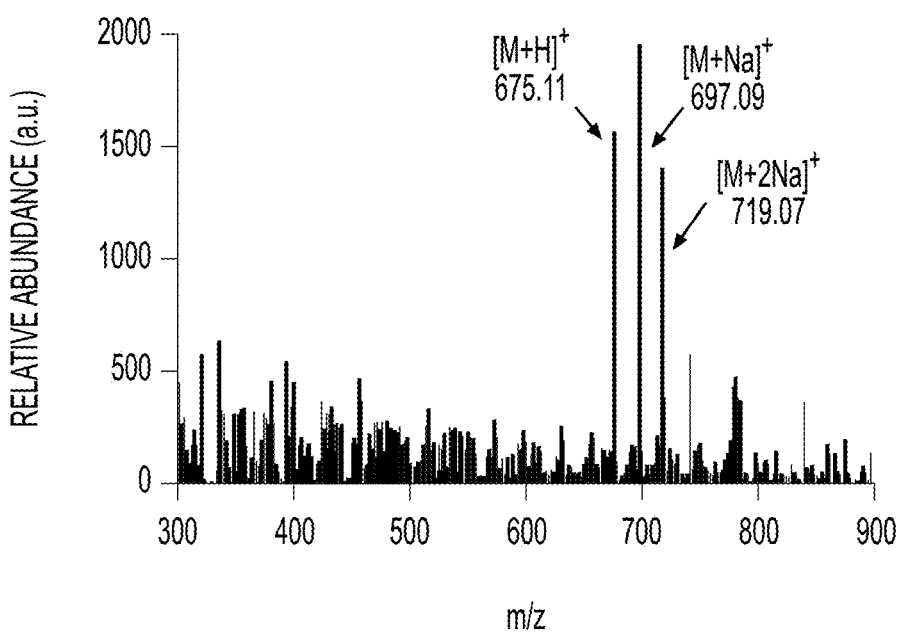
FIG. 3B is a mass spectrum of 3'3'-cGAMP released from PLGA-2 on day 8 showing molecular ions [M+H]+=675.11, [M+Na]+=697.09, [M+2Na]+=719.07. Microdevices were incubated at 37° C. in PBS.
Figure 3C:
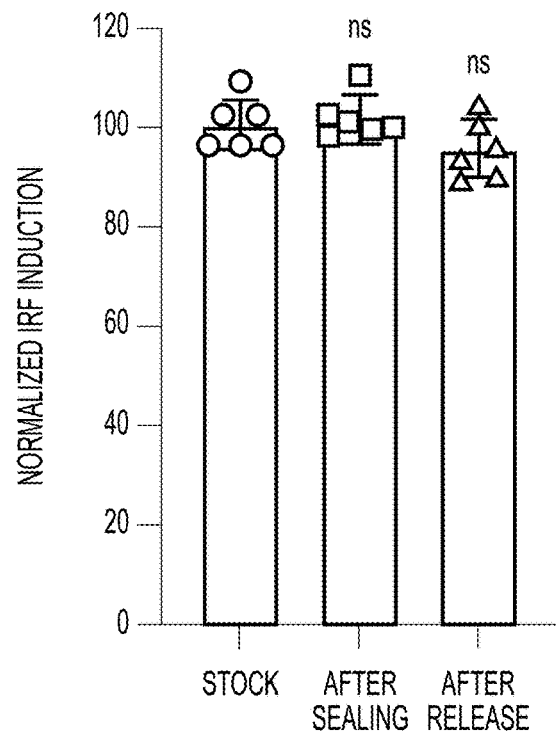
FIG. 3C is a bar graph showing the response of incorporated and released cGAMP from PLGA-2 on an interferon regulatory factor (IRF) reporter cell line (n=6). Error bars represent standard deviation. Statistical significance was calculated using one-way analysis of variance (ANOVA).
Figure 3D:
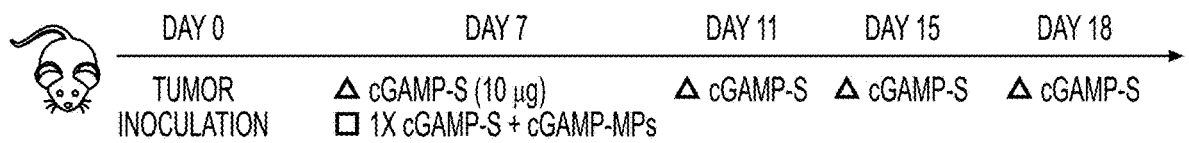
FIG. 3D is a schematic representation of the treatment scheme of B16F10 and 4T1 tumor-bearing mice treated with a single injection of 3'3'-cGAMP-loaded PLGA-1, 2, and 3 at day 7 or four injections of soluble 3'3'-cGAMP at days 7, 11, 15, and 18 post tumor inoculation.

STING agonist-loaded PLGA-1, 2, and 3 were fabricated with a drug loading of 2 µg per microdevice. 3'3'-cGAMP, a linkage isomer of naturally produced 2'3'-cGAMP, was used here due to the enhanced stability against ecto-nucleotide pyrophosphatase/phosphodiesterase 1 (ENPP1), which primarily hydrolyzes cGAMP (Kato K. et al., *Nat Commun.*, 9(1):4424(2018)). 3'3'-cGAMP released from PLGA-1, 2, and 3 in pulses at nearly identical time as the fluorescent molecules in vitro (FIG. 3A). The stability of incorporated cGAMP in physiological conditions is critical for the retention of bioactivity upon release. To study the stability of 3'3'-cGAMP in microdevices, cGAMP-loaded PLGA-2 microdevices were incubated in PBS at 37° C., and the structure integrity of cGAMP in the supernatant over time was analyzed by liquid chromatography-mass spectrometry (LC-MS). Released cGAMP showed identical elution time and molecular mass with standard 3'3'-cGAMP (FIG. 3B). The bioactivity of released cGAMP was also tested by an interferon regulatory factor (IRF)-reporter cell line (RAW-Lucia™ ISG cells). Released cGAMP from PLGA-2 maintained over 95% of bioactivity (FIG. 3C). Collectively, these data demonstrated that incorporated cGAMP remained stable and could be completely released from PLGA microdevices (Wu J., et al., Science, 339(6121):826-30 (2013)).

To determine if a single injection of several timed-release populations of cGAMP-loaded PLGA-MPs could stimulate anti-tumor immunity comparable to multiple injections of soluble cGAMP (cGAMP-S), mice bearing poorly immunogenic B16F10 melanoma tumors were treated intratumorally with 1) a single injection of cGAMP-S(10 µg) combined with cGAMP-loaded PLGA-1, 2, and 3 microdevices (cGAMP-MPs, 10 µg cGAMP per formulation) to mimic four doses; 2) four injections of cGAMP-S(10 µg cGAMP per injection) administered at multiple time points corresponding to PLGA release (FIG. 3D); 3) a single intratumoral injection of empty PLGA-1, 2, and 3 microdevices (EPs); and 4) a single intratumoral injection of high-dose cGAMP-S(40 µg) and EPs. Untreated mice were used as negative controls.

To compare the therapeutic efficacy of PLGA-MPs to other sustained release systems, three sustained release formulations including dextran hydrogel, polyvinyl alcohol (PVA) hydrogel, and collagen hydrogel were fabricated. The in vitro release kinetics study showed that over 99% of cGAMP released from all three hydrogel formulations within 24 hours, which is consistent with previously reported sustained release systems for cGAMP (Leach D G., et al., Biomaterials, 163:67-75(2018); Junkins R D. et al., J Control Release., 270:1-13 (2018)). Collagen gel, which exhibits the slowest release rate among tested gels, was loaded with 40 µg of cGAMP and intratumorally administered into tumor-bearing mice as controls.

Figure 3E:
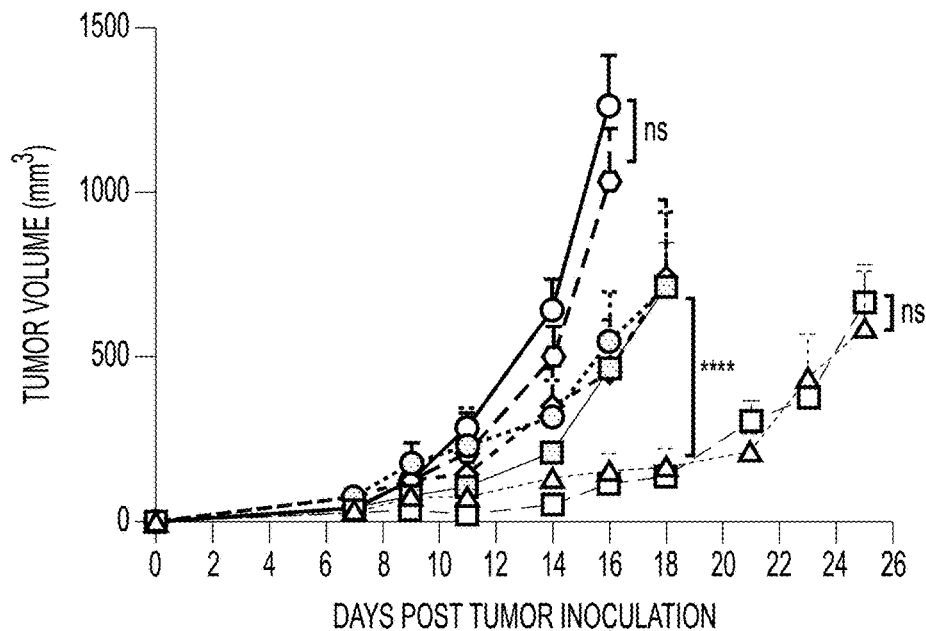
FIGS. 3E-3F are graphs showing the average tumor growth (FIG. 3E) and Kaplan-Meier survival curves (FIG. 3F) of B16F10 melanoma-bearing mice treated with different groups (n=8 biologically independent samples). The legend for FIG. 3E is shown in FIG. 3F.
Figure 3F:
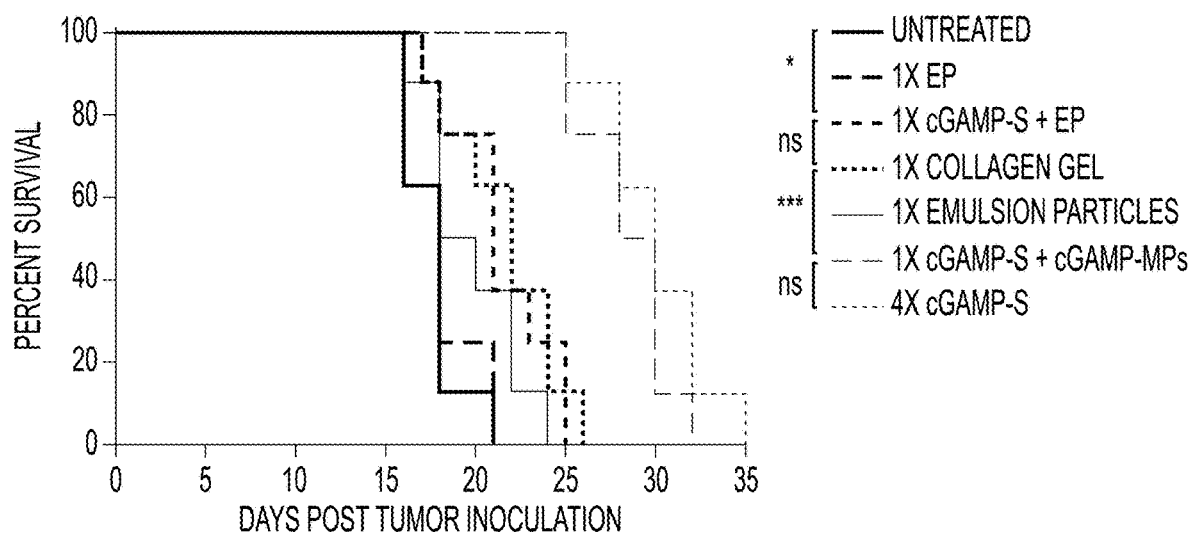
Figure 3G:
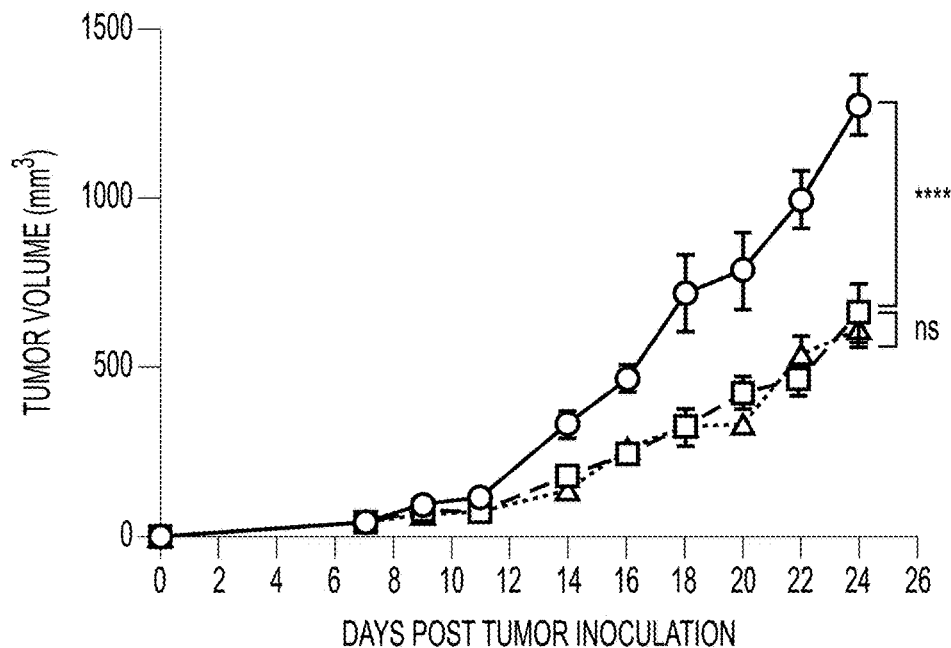
FIGS. 3G-3H are graphs showing the average tumor growth curve (FIG. 3G) and survival analysis (FIG. 3H) of mice bearing orthotopic 4T1 breast tumors (n=8 biologically independent samples). Statistical significance was calculated by two-way ANOVA and Tukey's multiple comparisons test: $*P<0.05$, $P<0.01$, $*P<0.001$, $****P<0.0001$. Data present mean±s.e.m.
Figure 3H:
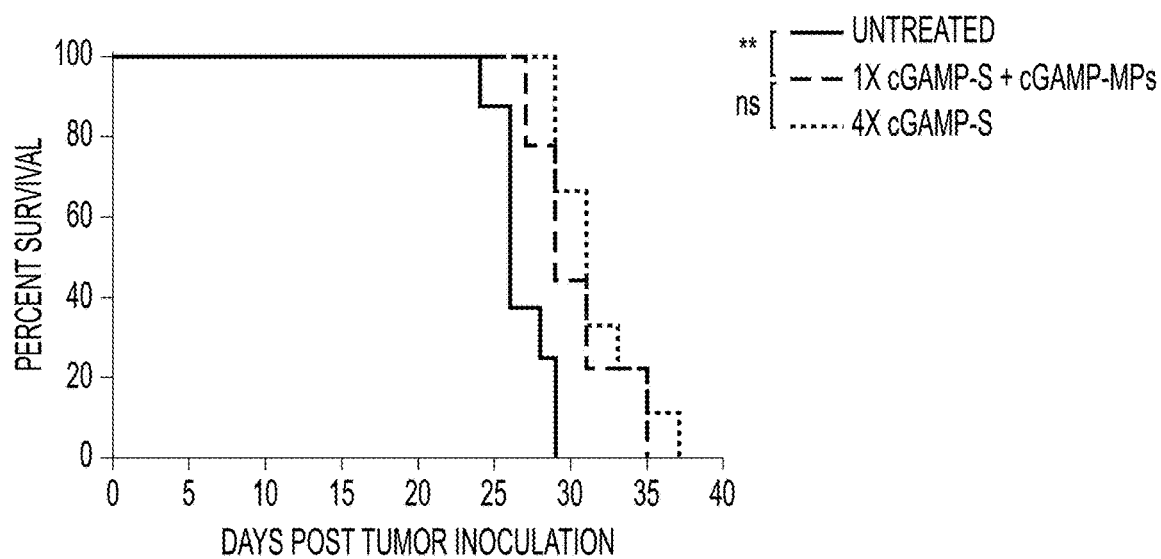

Tumors grew rapidly in untreated and EP-treated groups and all mice died within 21 days, indicating that PLGA microdevices alone did not inhibit tumor growth (FIGS. 3E and 3F). A single injection of high-dose cGAMP-S(40 µg) and EP exhibited an antitumor effect at early time points but failed to achieve sustained tumor inhibition. The survival time was slightly extended from 21 days for untreated mice to 25 days, indicating the necessity of multiple doses for effective tumor inhibition. Collagen gel did not show superior tumor inhibition or survival compared to cGAMP-S+EP. In contrast, a single injection of cGAMP-S with cGAMP-MPs significantly inhibited tumor growth and prolonged animal survival with no statistical difference compared to four injections of cGAMP-S at equivalent doses Similar results were also observed in both orthotopic (FIGS. 3G and 3H) and subcutaneous triple-negative breast cancer model (4T1) following the same treatments. The systemic interleukin-6 (IL-6) response of orthotopic 4T1 tumor-bearing mice was evaluated from day 1 to 7. The IL-6 levels were elevated in both cGAMP-MPs and 4×cGAMP-S treated groups, indicating the successful release of cGAMP from PLGA-MPs into tumors as well as the blood stream.

Example 4: Single Injection of cGAMP-MPs Stimulated Potent Antitumor Immunity Via STING Pathway Activation Materials and Methods Western Blot and Quantitative Polymerase Chain Reaction (qPCR)

Figure 4A:
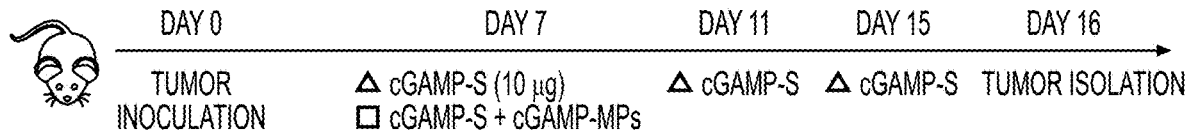
FIGS. 4A-4I show analysis of immune response and STING pathway activation.

Mice bearing B16F10 tumors were treated with the following 4 experimental groups (n=8): untreated, 1×EPs, 3×cGAMP-S, and 1×cGAMP-S plus cGAMP-MPs, respectively (FIG. 4A). Tumors were collected at day 16 post tumor inoculation and cut into 50-100 mg small pieces in a 1.5 mL microcentrifuge tube. The tumors were lysed in radioimmunoprecipitation assay (RIPA) buffer (Sigma-Aldrich), homogenized, and centrifuged at 20130 rcf for 10 min. The protein content in the supernatant was quantified using a bicinchoninic acid protein assay kit (Thermo Fisher Scientific, MA, USA). Equal amounts of proteins (20 µg) were separated on a 4 to 15% gradient SDS-polyacrylamide gel (Bio-Rad, Hercules, CA) and electro-transferred to nitrocellulose membrane. The membranes were then blocked with 5% milk in tris-buffered saline supplemented with 0.05% Tween 20 and further incubated with GAPDH monoclonal antibody (Invitrogen, CA, cat. no. MA5-27912), phospho-TBK1/NAK (Ser172) (D52C2) Rabbit mAb (Cell Signaling Technology, cat. no. 5483S), or phospho-IRF-3 (S396) Rabbit mAb (Cell Signaling Technology, cat. no. 4947S) at 4° C. overnight. The membranes were then incubated with goat anti-rabbit IgG (H+L) Secondary Antibody, HRP (Invitrogen, cat. no. TG266717) for 1 h at room temperature. Protein bands were visualized by chemiluminescence using the ECL Western Blotting Substrate (Thermo Fisher Scientific, MA).

For q-PCR experiments, total RNAs were extracted from tumors by RNeasy Kit (Qiagen, Inc.) according to manufacturer's protocol. Total RNA was then reversed-transcribed to cDNA using a high-capacity cDNA reverse transcription kit (Thermo Fisher Scientific, MA). The obtained cDNA was amplified with TaqMan Gene Expression Master mix (Thermo Fisher Scientific, MA) using a 384 well LightCycler 480 (Roche, Venlo, Netherlands). The primers used are IRF7 (Thermo Fisher, assay Id. Mm00516793_g1), CXCL10 (Thermo Fisher, assay Id. Mm00445235_m1), and GAPDH (Thermo Fisher, assay Id. Mm99999915_g1). Samples were analyzed in triplicates.

Flow Cytometry

To stain the cell surface markers for flow cytometry analysis, cells were pre-treated with anti-CD16/32-Fc blocker (Biolegend, cat. no. 101319) and stained with fluorophore-conjugated antibody solution according to manufacture suggested dilutions on ice for 1 h. To stain the intracellular marker, e.g., IFN-γ, cells were pre-stimulated with cell stimulation cocktail (eBioscience, cat. no. 00-4970-93) for 4-6 h, fixed and permeabilized using fixation/permeabilization solution kit (BD, cat. no. 554714), and then stained with both anti-IFN-γ and other surface antibodies. Antibodies used for flow cytometry studies were anti-CD86-BUV395 (BD, cat. no. 564199), anti-CD45-BUV737 (BD, cat. no. 564880), anti-TCRβ-BV421 (Biolegend, cat. no. 109229), anti-NK1.1-BV605 (Biolegend, cat. no. 108739), anti-NK1.1-BV605 (Biolegend, cat. no. 108739), anti-CD8a-FITC (BD, cat. no. 553030), anti-CD4-PerCP/Cy5.5 (BD, cat. no. 550954), anti-CD62L-PE (Biolegend, cat. no. 104407), anti-CD19-PE/Cy7 (eBioscience, cat. no. 25-0193-81), anti-CD3-PE/594 (Biolegend, cat. no. 100245), anti-FOXP3-APC (eBioscience, cat. no. 17-5773-80), anti-CD11b-AF700 (Biolegend, cat. no. 201222), anti-CD8a-BV421 (Biolegend, cat. no. 100737), anti-Ly6g-BV510 (Biolegend, cat. no. 127633), anti-Siglec F-BV605 (BD, cat. no. 740388), anti-MHC II-BV786 (BD, cat. no. 743875), anti-Ly6c-AF488 (Biolegend, cat. no. 128021), anti-CD11c-PerCP/Cy5.5 (Biolegend, cat. no. 117327), anti-CD206-PE (Biolegend, cat. no. 141705), anti-CD197-PE/594 (Biolegend, cat. no. 120121), anti-F4/80-PE/Cy7 (Biolegend, cat. no. 123113), anti-CD200R3-APC (Biolegend, cat. no. 142207), anti-CD11b-AF700 (Biolegend, cat. no. 101222), and viability dye eFluor 780 (eBiosciecne, cat. no.

65-0865-14). Flow cytometry data were acquired on an LSRFortessa cell analyzer (BD) and analyzed using FlowJo software.

Results

Figure 4B:
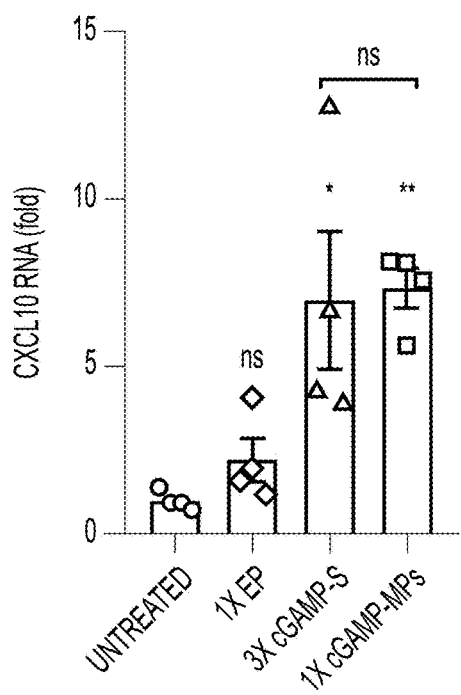
Figure 4C:
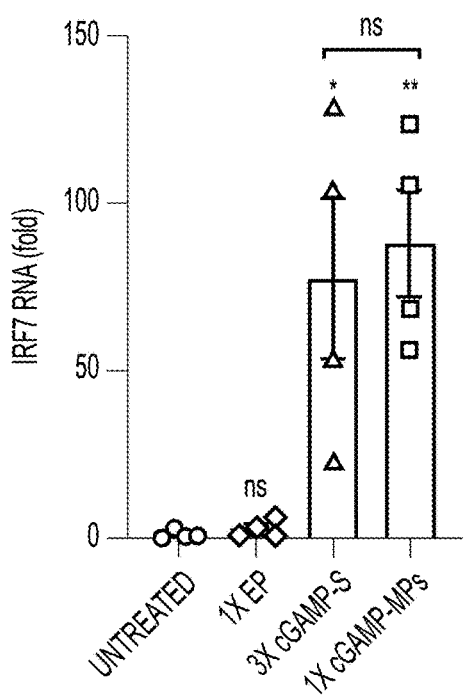

Next, the activation of STING pathway and antitumor immunity within the TME of B16F10 melanoma tumors was investigated. A combination of soluble cGAMP and cGAMP-loaded PLGA-1 and 2 microdevices was injected intratumorally at day 0 to mimic a total of three doses (FIG. 4A). cGAMP-MPs substantially inhibited tumor growth, which is consistent with the tumor inhibition findings. Tumors were isolated one day after the third cGAMP-S injection and analyzed by western blot and quantitative polymerase chain reaction (qPCR). cGAMP-MPs increased messenger RNA (mRNA) level of interferon-stimulated genes (ISGs) CXCL10 (6.8-fold over untreated) and IRF7 (58.5-fold over untreated), which are comparable to 3×cGAMP-S treated mice (7.2- and 66.5-fold increase of CXCL10 and IRF7, FIGS. 4B-4C). Additionally, tumors treated with cGAMP-MPs and 3×cGAMP-S showed high expression levels of phosphorylated-TBK1 (p-TBK1) and phosphorylated-IRF3 (p-IRF3). Untreated and EP treated tumors did not exhibit detectable expression of p-TBK1 and p-IRF3. These data demonstrate that cGAMP-MPs successfully activated the STING pathway and induced ISG production at a similar level to multiple injections (Burdette DL., et al., Nature, 478(7370):515-8 (2011); Corrales L., et al., J Clin Invest., 126(7):2404-11 (2016)). In contrast, empty microdevices did not trigger production of p-TBK1, p-IRF3 and ISGs.

Figure 4D:
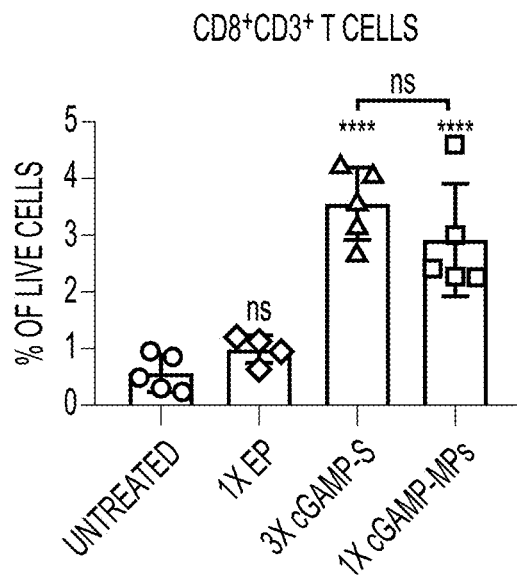
Figure 4E:
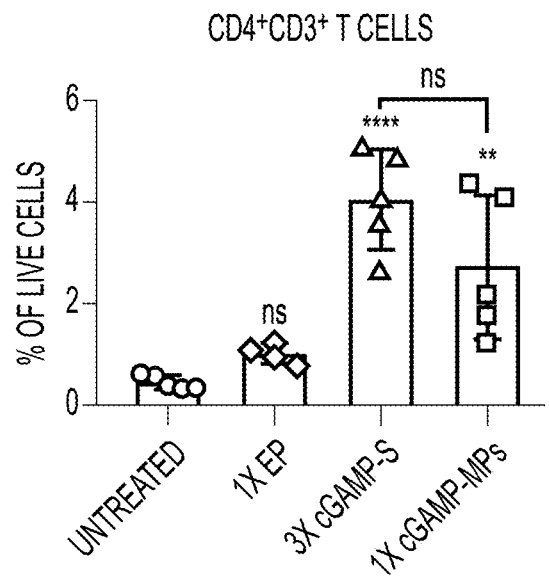
Figure 4F:
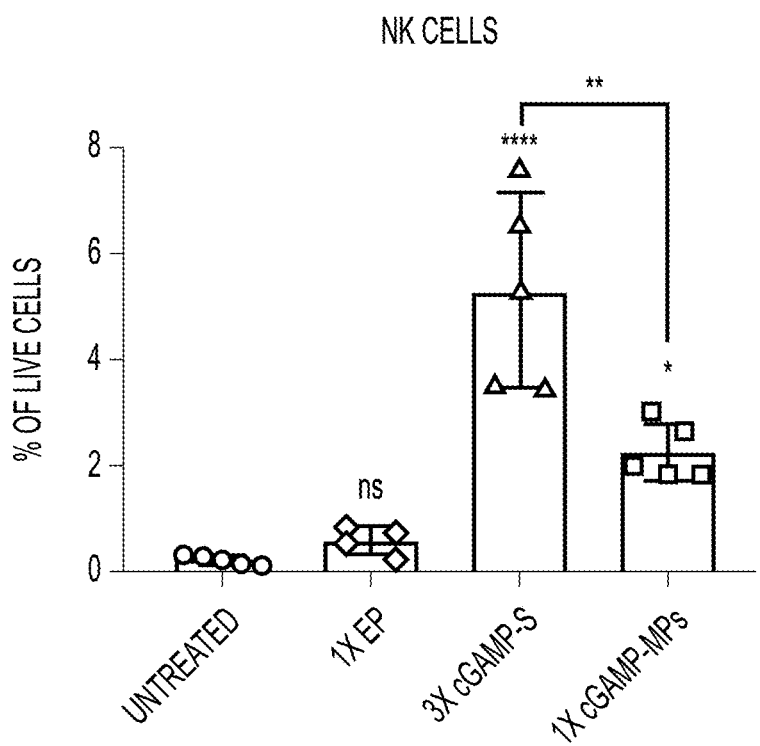

Activation of the STING pathway in the TME has been shown to promote lymphocyte infiltration, which is the major mediator for effective cancer immunotherapy (Cheng N., et al., JCI Insight, 3(22). pii: 120638 (2018)). Flow cytometry analysis of tumors showed that 3×cGAMP-S and cGAMP-MPs increased TILs by approximately 23.5- and 17.6-fold compared to the untreated group. Among these TILs, tumor-infiltrating CD8+ and CD4+ T cells were substantially increased by 24.4- and 23.6-fold for 3×cGAMP-S treated group, and 16.2- and 22.1-fold for cGAMP-MPs treated group, respectively (FIGS. 4D-4E). The amounts of CD8+ and CD4+ T cells of cGAMP-S treated group were slightly higher than for cGAMP-MP treated group, but the differences were not statistically significant. 3×cGAMP-S and cGAMP-MPs treatments also showed 1.2- and 1.5-fold increase of CD8+/CD4+ T cell ratio, which is a commonly reported positive prognostic indicator of immunotherapy (Rudqvist N P., et al., Cancer Immunol Res., 6(2):139-150 (2018); Shae D. et al., 2019). In agreement with this enriched CD8+ T cell infiltration and enhanced antitumor activity, terminal deoxynucleotidyl transferase-mediated deoxyuridine triphosphate nick end labeling (TUNEL) showed a greater abundance of apoptotic cells for the cGAMP-MPs and 3×cGAMP-S treated groups. Additionally, 3×cGAMP-S and cGAMP-MPs increased infiltrating natural killer (NK) cells (FIG. 4F), another important group of cytotoxic lymphocytes that shape the adaptive immune response and were found to be effective for spontaneous STING-mediated protection against B16F10 tumors (Marcus A., et al., Immunity, 49(4):754-763.e4 (2018). Alternatively, the group receiving empty microdevices did not increase TILs within the TME, confirming its inability to activate the STING pathway. Differences with regulatory T cells were not observed for all groups.

Figure 4G:
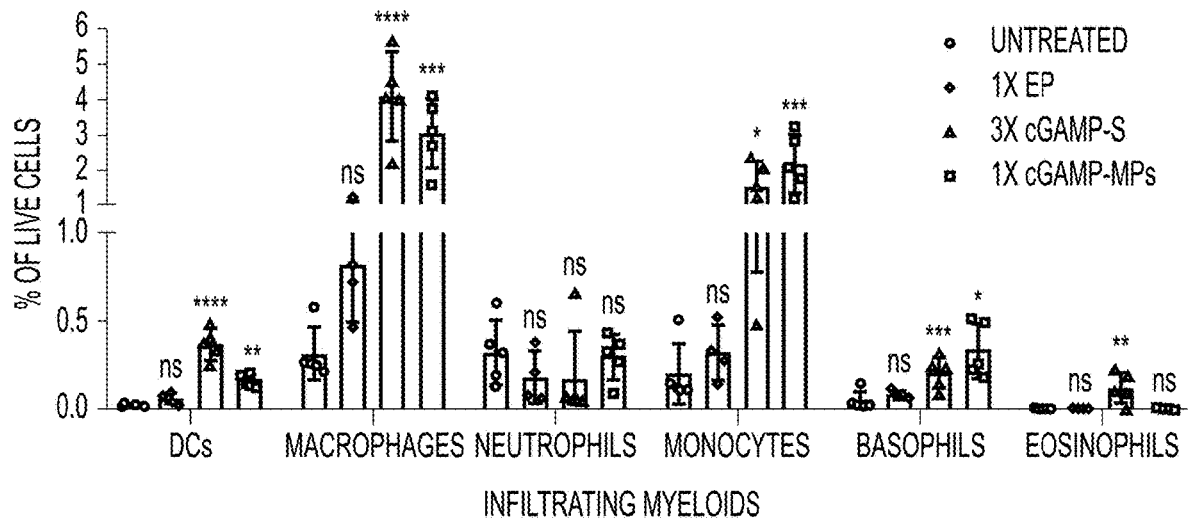
Figure 4H:
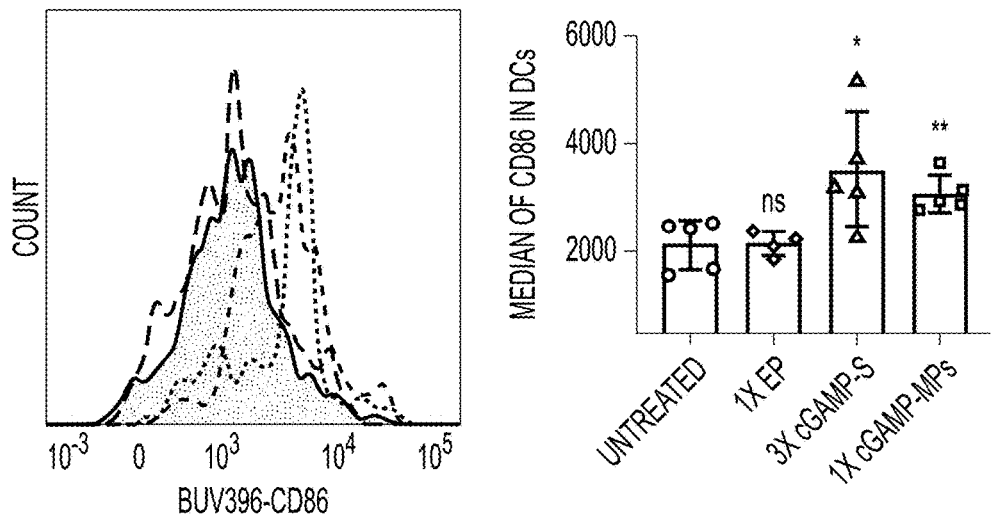

The changes in dendritic cells (DCs) and myeloid composition in B16F10 melanoma TME after treatments were then evaluated. Both 3×cGAMP-S and cGAMP-MPs promoted the influx of DCs (CD11b-CD11c+), basophils (CD11b+Gr-1-CD200R3+), monocytes (CD11b+F4/80-Ly6c+Ly6g−), and macrophages (CD11b+F4/80+), creating an innate inflammatory niche that potentially primes the adaptive immunity (FIG. 4G; Iwasaki A. and Medzhitov R., Nat Immunol., 16(4):343-53 (2015)). In contrast, empty microdevices did not increase the myeloid cell population, suggesting the low-immunogenicity of PLGA. Additionally, surface expression of CD86, which is a maturation marker overexpressed on activated tumor infiltrating DCs (Han TH., et al., J Immunother., 32(4):399-407 (2009)), was increased by 1.7- and 1.5-fold for 3×cGAMP-S and cGAMP-MPs treated groups (FIG. 4H).

Figure 4I:
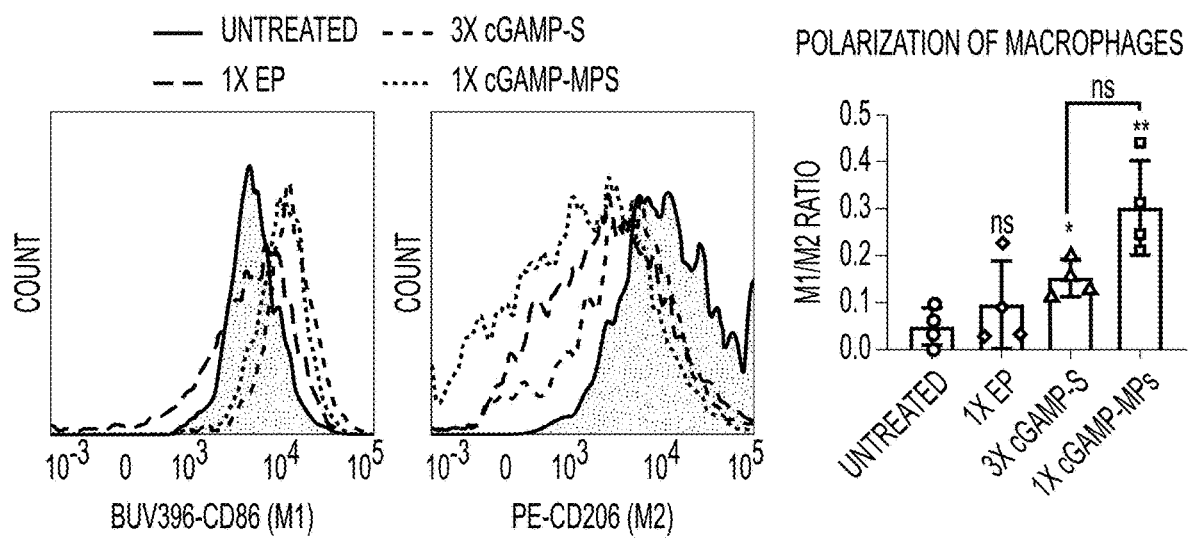

The maturation of DC in combination with enriched TILs and elevated intratumoral ISGs suggest potential activation of adaptive immunity (Bose D., Int J Mol Sci., 18(11) (2017); Vatner R E., Mol Immunol., 110:13-23 (2019)). The polarization of macrophages within the TME, another key function associated with cGAMP was then evaluated (Ohkuri T. Cancer Immunol Immunother., 66(6):705-716 (2017)). After 3 doses of soluble cGAMP or 1 dose of cGAMP-MPs, repolarization of M2-like macrophages in the tumor to M1-like phenotype was observed, which is consistent with previous studies of STING agonist-treated tumors and suggests reduced immunosuppressive TME. Notably, cGAMP-MPs consistently downregulated the canonical M2 surface marker (CD206) and upregulated M1 surface markers (CD86, FIG. 4I). Quantitative analysis showed that cGAMP-MPs induced approximately a 2-fold greater M1/M2 ratio than did the 3×cGAMP-S treated group. Empty microdevices slightly increased the M1/M2 ratio compared to the untreated group but without statistical difference. These data suggest that loading cGAMP in PLGA-MPs may promote M1-like polarization, possibly due to the acidic degradation products of PLGA, which have been shown to stimulate proinflammatory macrophages (Nilsson B., et al., Mol Immunol., 44(1-3):82-94 (2007); Amini A R., et al., J Long Term Eff Med Implants., 21(2): 93-122 (2011); Ceonzo K., et al., Tissue Eng., 12(2):301-8 (2006)). Further studies on macrophage polarization kinetics are required to fully elucidate the function of PLGA-MPs on macrophage polarization in the TME.

Example 5: Single Injection of cGAMP-MPs Triggers Potent Systemic Antitumor Immunity Materials and Methods Treatment of contralateral B16F10 tumors $2 \times 10^5$ B16F10 cells were subcutaneously injected to the right rear flank of C57BL/6 female mice at day 0. Another $2 \times 10^5$ B16F10 cells were subcutaneously injected to the left rear flank at day 2 to mimic metastatic tumor. Seven days after primary tumor inoculation, B16F10 tumor-bearing mice were divided into 4 experimental groups (n=8 for each group): untreated, cGAMP-MPs, anti-PD1, and cGAMP-MPs plus anti-PD1, respectively. cGAMP-MPs (10 µg of cGAMP-S, 5 PLGA-1 microdevices containing 10 µg of cGAMP, and 5 PLGA-2 microdevices containing 10 µg of cGAMP) in 50 µL MC solution were intratumorally injected to the primary tumor (on the right side). For anti-PD1 and cGAMP-MPs plus anti-PD1 treated groups, 100m of anti-PD1 anti body (Biolegend, cat. no. 114114) was intraperitoneally injected at days 7, 10, and 14 post primary tumor inoculation (FIG. 5D). The distant tumor (left side) did not receive any treatments. Tumor size was measured every other day started at day 7 post tumor inoculation with a digital caliper. Tumor volume was calculated using the following formula: length (mm)×width$^2$ (mm)×0.5. Animals were euthanized when showing signs of poor health condition or when the tumor size of either side exceeded 1500 mm$^3$.

Treatment of Metastatic 4T1 Model

2×10$^5$ 4 T1 cells were injected into the mammary fat pad. Seven days after injection, tumor-bearing mice were divided into 3 experimental groups: untreated, 3×cGAMP-S, and 1×cGAMP-S plus cGAMP-MPs (10m of cGAMP-S, 5 PLGA-1 microdevices containing 10 μg of cGAMP, and 5 PLGA-2 microdevices containing 10 μg of cGAMP). The primary tumor was surgically removed at day 18 to extend survival. Mice were euthanized at day 34. Lung tissues were stained with India ink and fixed in Fekete's solution. Metastatic foci on the lung were counted under a microscope. Unstained lung tissues were fixed in formalin and stained by H&E. Quantitation of metastatic tumor cells of H&E stained sections was performed using an Aperio ImageScope using tuned positive pixel count algorithm. Briefly, input hue value in the positive pixel count algorithm was tuned to positively select normal lung tissues in red to orange range, while the tumors were negatively selected in purple. Percentage area of tumor metastasis per total lung area was calculated by the number of negative counts (purple)/the number of total counts (purple, orange, and red)×100%. Three H&E sections per lung at different depths were analyzed and averaged to obtain the percentage of tumor over the lung for one mouse. Four or five mice were analyzed for each group.

Immunofluorescence Staining

Tumor sections (5 μm) were fixed with 4% paraformaldehyde, blocked with 3% bovine serum albumin, and permeabilized with 0.1% Triton X-100 in PBS. The tumor sections were then incubated with anti-CD8 alpha antibody (1:200, Abcam, cat. no. ab217344) at 4° C. overnight and goat anti-rabbit IgG H&L (Alexa Fluor® 488) (1:1000, Abcam, cat. no. ab150077) secondary antibody at room temperature for 1 h. Apoptotic tumor cells were stained using a in situ cell death detection kit (Roche) according to the manufacturer's instructions. Images were acquired on a Nikon A1R Ultra-Fast Spectral Scanning Confocal Microscope (Shinagawa, Tokyo).

Results

Figure 5A:
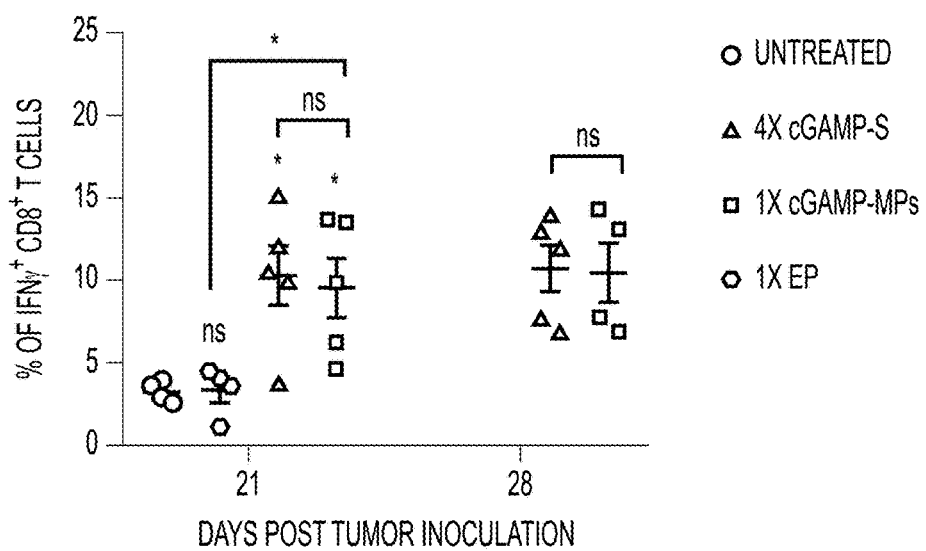
FIG. 5A is a graph showing quantitative analysis of IFNγ+CD8+ T cells in the serum collected at day 21 and 28 (n=4 to 5, treatment scheme shown in FIG. 3D). Untreated and 1×EP-treated mice did not survive at day 28. Data represent average±s.e.m.
Figure 5D:
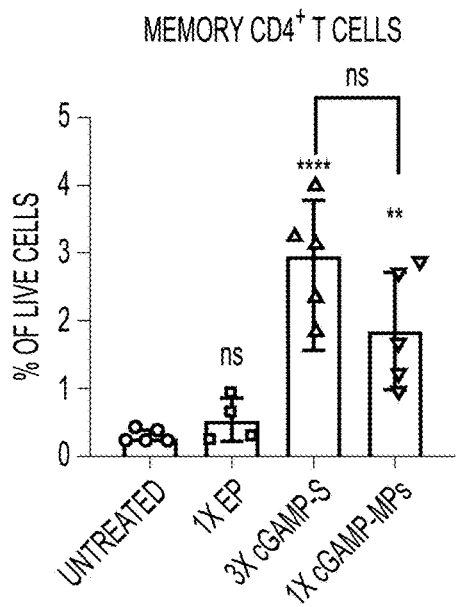
FIG. 5D is a schematic of treatment regimen on a contralateral B16F10 model. Tumors were inoculated on the right and left rear flanks of mice at days 0 and 2. The primary tumor (right side) was treated with a single intratumoral injection of cGAMP-S+cGAMP-MPs and three intraperitoneal injections of anti-PD-1 antibodies (ICB).
Figure 5D:
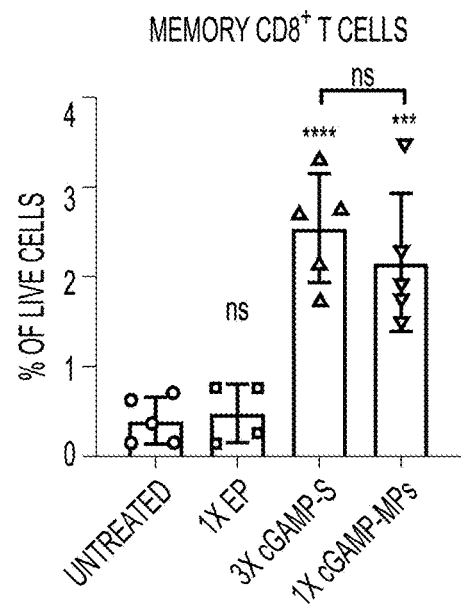
Figure 5D:
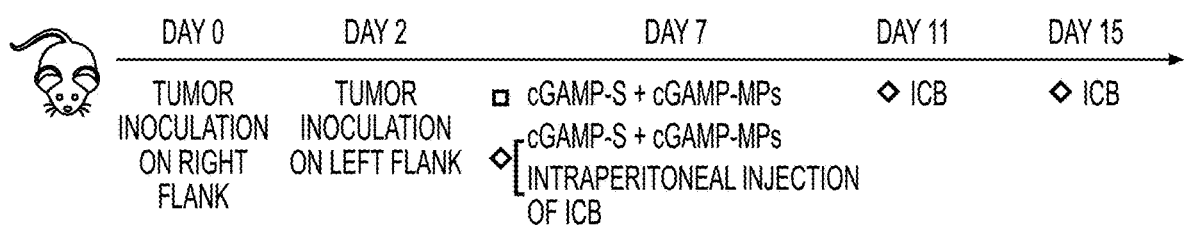

To study whether activation of STING in the TME triggers systemic antitumor immunity, mouse serum was collected from the antitumor efficacy study of B16F10 melanoma model (FIG. 3D) 21 and 28 days after tumor inoculation and analyzed by flow cytometry. cGAMP-MPs and 4×cGAMP-S treatments increased 5.1- and 4.9-fold of IFNγ+CD8+ T cells in serum at day 21 compared to the untreated group (FIG. 5A). The number of IFNγ+CD8+ T cells remained at an identical level at day 28, demonstrating long-lasting systemic immune response. In addition, cGAMP-MPs also increased the number of memory CD62L-CD44+CD4+ T cells (~6.2-fold over untreated group) and CD62L-CD44+CD8+ T cells (~5.4-fold over untreated group) in TME (FIGS. 5B-5C). Collectively, a single injection of cGAMP-MPs generated long-lived systemic antitumor immunity and local immunological memory, potentially preventing tumor recurrence and metastases.

Figure 5E:
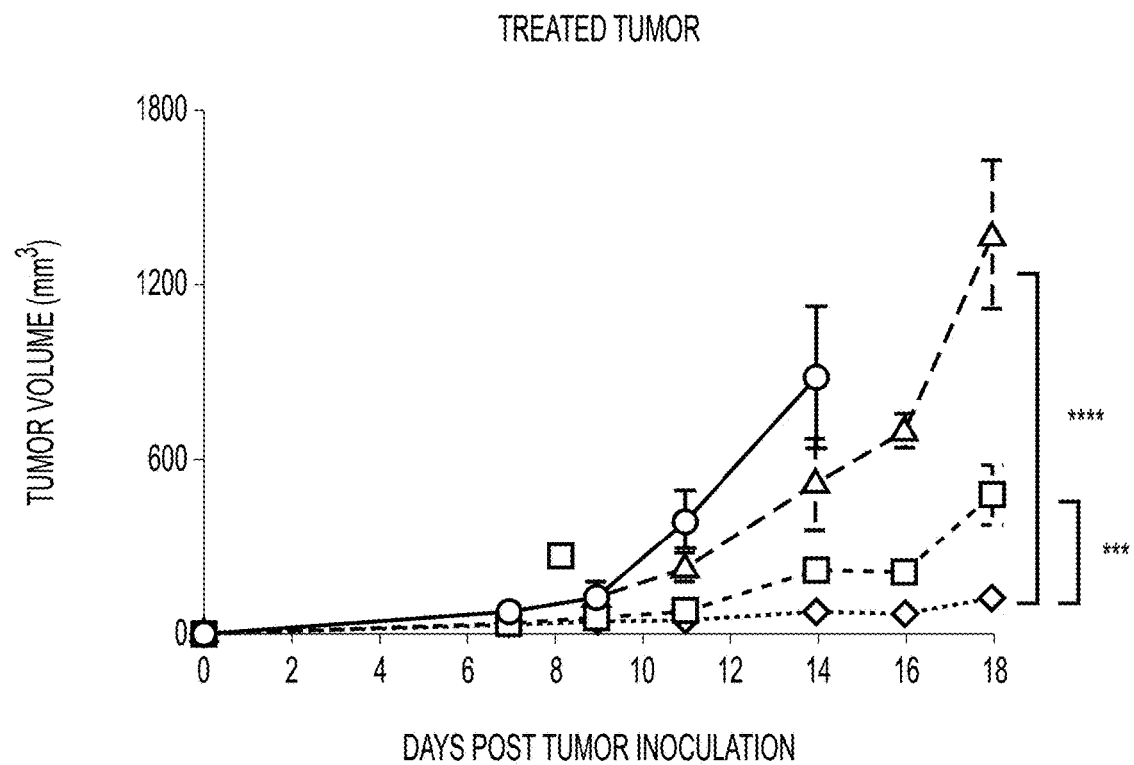
FIGS. 5E-5F are graphs showing the average tumor growth curves of treated (FIG. 5E) and distant tumors (FIG. 5F, n=8). Data represents average±s.e.m.
Figure 5F:
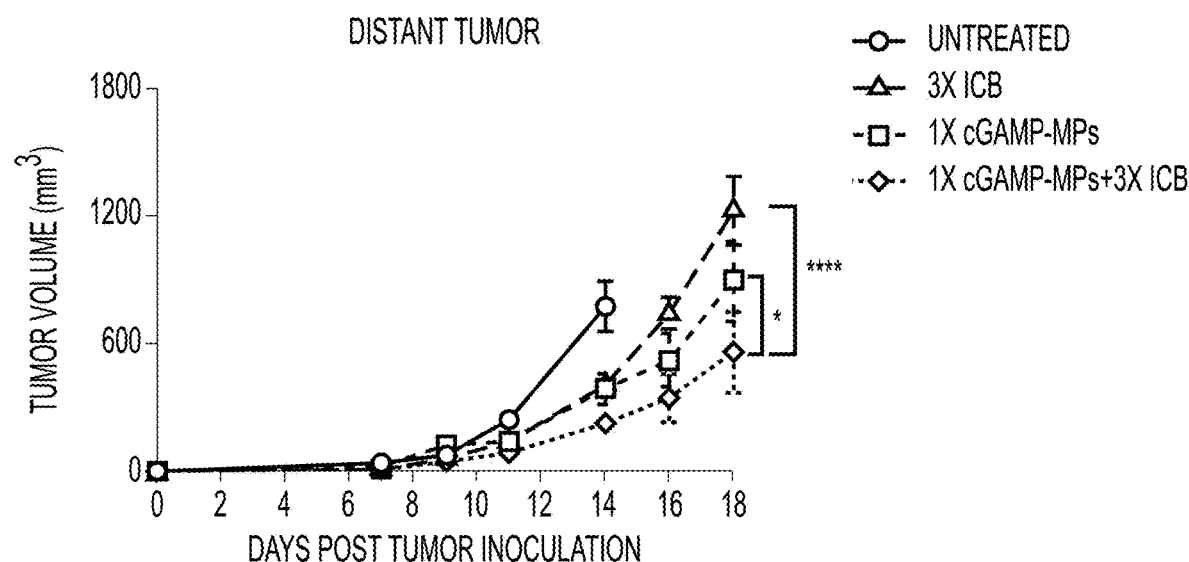

Next, a contralateral B16F10 tumor model was used to study whether cGAMP-MPs could inhibit the growth of distant tumors. The primary tumor was treated by a single intratumoral injection of cGAMP-S, cGAMP-loaded PLGA-1, and PLGA-2 to achieve overall three doses at days 0, 4, and 8, respectively. The distant tumor did not receive any treatment (FIG. 5D). cGAMP-MPs significantly inhibited the growth of both the primary and distant tumors compared with the untreated group, thereby demonstrating strong systemic antitumor immunity (FIGS. 5E and 5F).

To evaluate whether cGAMP-MPs could improve the antitumor efficacy of immune checkpoint blockade (ICB) therapy, a combination therapy of cGAMP-MPs with anti-programmed death 1 was tested in the same contralateral B16F10 tumor model. Indeed, the combination of cGAMP-MPs and ICB showed greater inhibition on primary and distant tumor growth than individual therapies by themselves (FIGS. 5E and 5F), demonstrating the potential of combining cGAMP-MPs with ICB to potentiate the therapeutic effect.

The effect of cGAMP-MPs on inhibiting metastasis was then investigated using an orthotopic 4T1 model. The primary tumor was treated with a single injection of cGAMP-MPs at day 7 or multiple injections of cGAMP-S at days 7, 11, and 15 post tumor inoculation. The primary tumors were surgically removed at day 18 to extend survival time, which is needed to allow the development of metastasis. Lungs were then isolated and metastasis analyzed at day 34. cGAMP-MPs and 3×cGAMP-S treatments significantly decreased the number of metastatic foci on lung surfaces (FIG. 5H) and reduced the relative area of tumors in the lungs compared to untreated groups (FIG. 5I). cGAMP-MPs also exhibited a greater ability to decrease the percentage of metastatic tumor cells within lungs compared to 3×cGAMP-S (FIG. 5I), suggesting the benefits of a single injection for decreasing metastasis.

Example 6: Single Injection of cGAMP-MPs Inhibits Tumor Recurrence and Metastasis and Facilitates Treatment of Hard-to-Reach Tumors Materials and Methods Treatment of Surgically Removed B16F10 Tumor 2×10$^5$ B16F10 cells were subcutaneously injected to the right rear flank of C57BL/6 female mice. Six days after tumor inoculation, B16F10 tumor-bearing mice were randomly divided into 4 experimental groups (n=8 for each group): untreated, 1×cGAMP-S plus EPs, 3×cGAMP-S, and 1×cGAMP-S plus cGAMP-MPs, respectively. ~99% of tumor volume was surgically removed, leaving ~1% residual tumor to mimic residual microtumors. Upon the removal of tumors, cGAMP-MPs (10m of cGAMP-S, 5 PLGA-1 microdevices containing 10 μg of cGAMP, and 5 PLGA-2 microdevices containing 10 μg of cGAMP) or 1×cGAMP-S plus EPs (10m of cGAMP-S, 5 each of empty PLGA-1 and PLGA-2 microdevices) in 50 μL MC solution were directly applied to the surgical bed through a micropipette. For 3×cGAMP-S treated group, 10 μg of cGAMP-S was applied to the surgical bed after surgery followed by intratumoral injections of 10 μg of cGAMP at days 4 and 8 post-surgery (FIG. 6A). The wound was closed by an autoclip wound clip system. Tumor size was measured with a digital caliper every other day starting at day 7 post tumor inoculation. For the re-challenge experiment, 2×10$^5$ B16F10 cells were subcutaneously injected to the left rear flank of treated mice with complete responses. Tumor size was measured every other day with a digital caliper.

Treatment of an Orthotopic Pancreatic Tumor Model

A small incision was made to exteriorize the spleen and pancreas of C57BL/6 female mice. 5×10$^5$ KPC cells in 50 μL of PBS and Matrigel (1:1 mixture by volume) were injected into the tail of the pancreas. cGAMP-MPs (10 μg of cGAMP-S, 5 PLGA-1 microdevices containing 10 μg of cGAMP and 5 PLGA-2 microdevices containing 10 µg of cGAMP) or 1×cGAMP-S plus EPs (30m of cGAMP-S, 5 each of empty PLGA-1 and PLGA-2 microdevices) in 50 µL MC solution were also injected into the tail of the pancreas. The wound was then closed by an autoclip wound clip system. Mice were euthanized 25 days after tumor inoculation. The tumors were isolated and weighted by a balance. Metastasis to lungs was evaluated by H&E staining of lung sections.

Biodegradation of PLGA-MPs

Five empty PLGA-2 microdevices were subcutaneously injected into the rear flank of SKH1-E mice. Mice were euthanized at days 2, 8, and 30 after injection. The skin and subdermal tissue were collected and fixed in formalin-free fixative (Sigma-Aldrich) for 24 h. Tissues were then embedded in paraffin, cut into 5 µm tissue sections, stained with H&E, and imaged using an Aperio AT2 Slide Scanner (Leica Biosystems, Buffalo Grove, IL).

Results

Figure 6D:
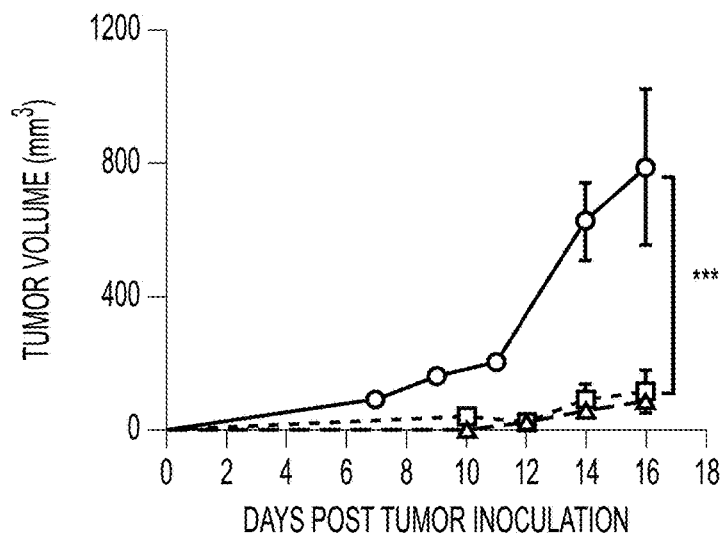

In the clinic, patients often develop recurrent tumors after surgery because of residual micro-tumors and circulating tumor cells (Demicheli R., et al., Ann Oncol., 19(11):1821-8 (2008); Alieva M., et al., Clin Exp Metastasis, 35(4):319-331 (2018); Al-Sahaf O., et al., Ann Surg., 252(6):1037-43 (2010)). To further expand the clinical applications of cGAMP-MPs, a surgical resection tumor model was adopted to evaluate the efficacy of cGAMP-MPs on inhibiting tumor recurrence (Wang C., et al., Nat Biomed Eng., 1(2017), doi:10.1038/s41551-016-0011; Chen Q., et al., Nat Nanotechnol., 14(1):89-97 (2019)). Six days after tumor inoculation, approximately 99% of B16F10 tumors were surgically removed. A combination of soluble cGAMP, cGAMP-loaded PLGA-1, and PLGA-2 was then directly deposited at the fresh surgical bed to achieve overall three doses at days 0, 4, and 8, respectively (FIG. 6A). Improved tumor inhibition (FIG. 6B) and enhanced survival (FIG. 6C) were observed in mice treated with cGAMP-MPs. The tumor recurrence rates of cGAMP-MPs and 3×cGAMP-S treated groups were both 25%, which was significantly lower than that of the untreated group (100%), whereas, a single dose of cGAMP-S plus EPs had limited efficacy with a high recurrence rate of 87.5%. Six out of eight cGAMP-MPs treated mice were tumor-free and survived for over 60 days after inoculation (FIG. 6C). These tumor-free mice were then re-challenged through subcutaneous injection of B16F10 cells. The tumors grew significantly slower in cGAMP-MPs and 3×cGAMP-S treated mice than in naïve mice (FIG. 6D). Survival analysis also showed prolonged survival time for treated groups (FIG. 6E), suggesting that cGAMP-MPs and 3×cGAMP-S provided protective immunity.

Figure 6E:
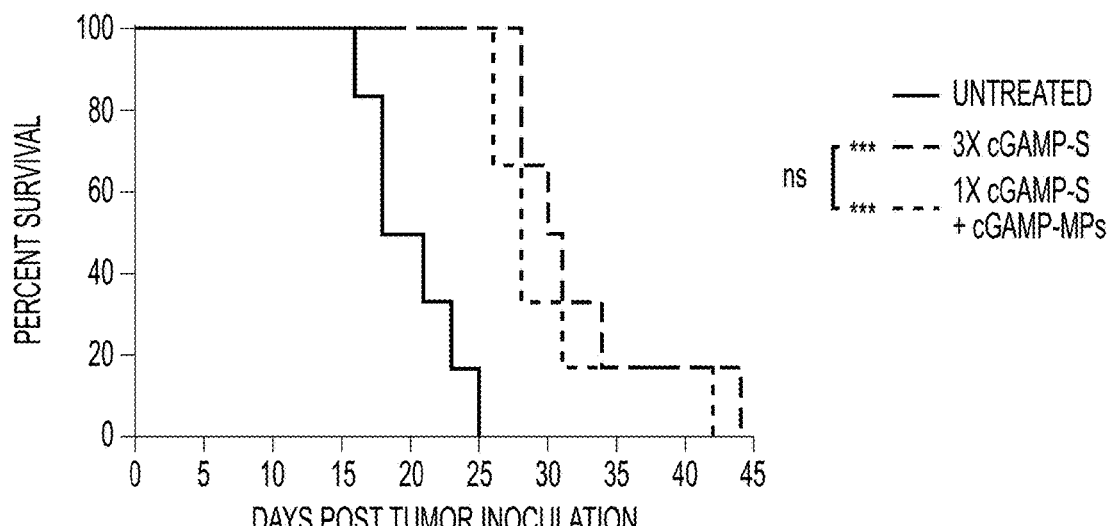
Figure 6F:
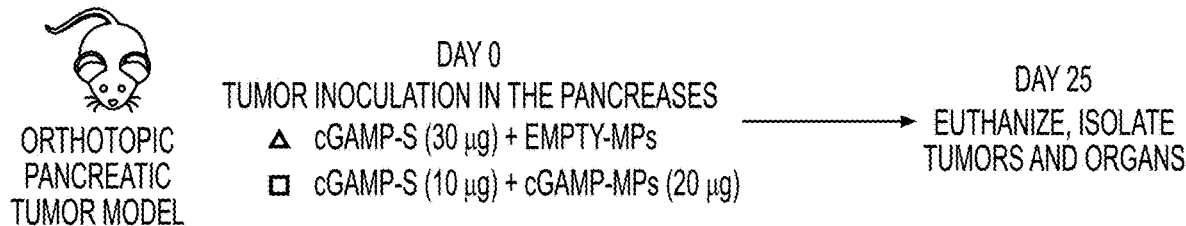
Figure 6G:
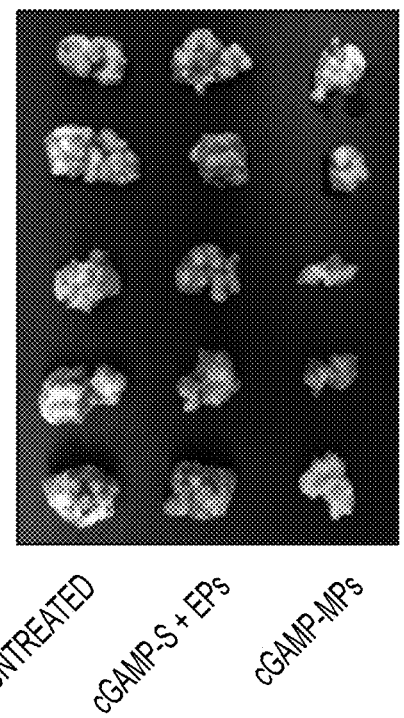
Figure 6H:
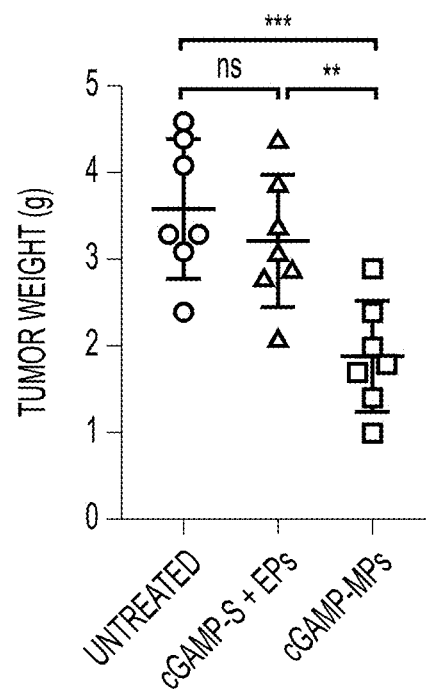

The therapeutic efficacy of cGAMP-MPs was further tested on an allograft model of pancreatic cancer (KPC model). A combination of soluble cGAMP, cGAMP-loaded PLGA-1, and PLGA-2 was injected after tumor inoculation in the pancreas to achieve overall three doses (10m per dose) at days 0, 4, and 8, respectively (FIG. 6F). Multiple intratumoral injections of soluble cGAMP are extremely difficult on such hard-to-reach tumors. Therefore, a single injection of a high dose cGAMP-S(30 µg) with EPs was performed at day 0. Untreated mice were used as negative controls. The tumor growth and metastasis was then analyzed 25 days post treatment. cGAMP-MPs significantly inhibited primary tumor growth in the pancreas and metastasis to lungs compared with untreated group (FIGS. 6G-6H and data not shown). In contrast, a high dose of cGAMP-S with EPs did not show benefits on tumor growth or metastasis. Collectively, these data demonstrate cGAMP-MPs are useful for hard-to-reach tumors and suggest the necessity of multiple doses at extended time points for effective therapy.

Toxicity Analysis

PLGA has been used in many FDA-approved medical devices owing to its biodegradability and biocompatibility (Makadia H K. and Siegel S J., Polymers (Basel)., 3(3): 1377-1397 (2011)). Flow cytometry analysis of immune cells in TME indicated that intratumorally administered empty PLGA-MPs induced minimal inflammation in situ (FIG. 4D-4H). In addition, weight loss and behavior changes was not observed in any of the animals throughout the treatment period for all in vivo studies (not shown). Hematoxylin and eosin (H&E) staining of histological sections of major organs (heart, liver, spleen, lung, and kidney) showed no clear change in morphology (not shown). The biodegradability of PLGA-MPs was further studied by subcutaneously injecting empty PLGA-2 into immunocompetent mice and H&E staining of skin tissues at days 2, 8, and 30 post-injection was performed. At day 2, PLGA-MPs exhibited cubic morphology under the skin with few lymphocytes and leucocytes around the microdevice, suggesting the presence of minimal inflammation. The microdevices then deformed to an ellipse shape due to hydrolysis of PLGA with diminished immune cells at day 8, just around the release window, which is consistent with flow cytometry analysis. There was no observance of any microdevices left in mice at day 30, which indicates complete degradation and clearance. Collectively, these data demonstrate that microfabricated PLGA-MPs exhibit minimal toxicity and can be completely degraded and cleared in vivo.

Adherence to current STING agonist-based therapy is challenging because of the frequent injections over a long period of time and the need of trained healthcare professionals for each injection. Poor patient adherence represents a significant challenge leading to treatment failures and large financial costs (Osterberg L., et al., 2005; Brown M T and Bussell J K., Mayo Clin Proc., 86(4):304-14 (2011)). Frequent injections for cancer treatment also cause a significant burden to daily lives of patients (Haithcox S., et al., BMC Nurs., 2(1):2 (2003)). Current research efforts have mainly focused on improving the cellular uptake of STING agonist and tumor targeting efficacy after systemic administration (Shae D. et al., 2019; Cheng N., et al., 2018; Koshy S T., et al., Adv Biosyst., 1(1-2). pii: 1600013 (2017)). The Examples demonstrate a unique approach of improving the overall effectiveness of STING agonist therapy by ensuring that patients receive every required dose at the correct time.

To replace multiple intratumoral injections of soluble STING agonist, PLGA-MPs could stay inside of tumors and release biologically active cargo at predetermined times. MicroCT analysis showed that these microdevices aggregated at the tumor injection site due to low mobility. LC-MS and in vitro analysis in cells showed cGAMP maintained >95% of bioactivity after release from PLGA-MPs. As demonstrated in the Examples, the release kinetics of PLGA-MPs were independent of the cargo released (AF647, AF647-dextran, and STING agonist, FIGS. 2A, 2B, 2E, 2F, and 3A) and the in vivo microenvironment (subcutaneous, B16F10, and 4T1 tumors, FIG. 2C). These observations are consistent with the degradation of PLGA being predominantly driven by hydrolysis. Enzymatic activity has negligible effect on PLGA degradation (Brown M T, et al., 2011)). The slightly acidic tumor microenvironment did not accelerate the release of low MW PLGAs (FIG. 2C), but may have effects on the long-term release of PLGA-MPs because of the acid-catalyzed hydrolysis of PLGA. Therefore, testing in vitro release in an acidic environment can be used to estimate release kinetics in tumors (FIG. 2A).

Pulsatile release over long periods of time is usually achieved by implantable drug delivery devices, which require invasive surgery to administer and remove (Farra R., et al., *Sci Transl Med.*, 4(122):122ra21 (2012)). One benefit of the PLGA-MPs is that they could be injected using a regular needle and completely degrade over time, thus improving patient compliance. Other injectable long-term drug release systems, such as emulsion-based microdevices (including PLGA formulations) or hydrogels, often show an initial phase of burst release and then a second phase of sustained release for hydrophilic drugs (Formiga F R., et al, *J Control Release.*, 147(1):30-7 (2010); Shahani K. and Panyam J., *J Pharm Sci.*, 100(7):2599-609 (2011)). Such release kinetics lead to an initial high dose, which could cause toxic side effects. Additionally, achieving sustained release of small/hydrophilic drugs, such as STING agonists, over weeks is extremely challenging. Drug encapsulation efficacy is also relatively low for emulsion-based microdevices (Yeo Y. and Park K., *Arch Pharm Res.*, 27(1):1-12 (2004)). The PLGA microdevices can achieve essentially 100% drug encapsulation efficacy and be combined to exhibit multiple burst release events at time points up to months (see FIGS. 2A-2G). The Examples demonstrate that low MW PLGA can achieve release times within the previously reported treatment schedules using cGAMP in animal models (FIG. 2). By tuning the MW, chain-end functionality, and copolymer ratio of PLGA, the release kinetics of the MPs can encompass pulsatile release over months or even a year. Therefore, customizable doses can be administered by physically mixing PLGA-MPs with different release profiles within one injection.

As shown in the Examples, the antitumor efficacy of single-administered PLGA-MPs is comparable with multiple injections of cGAMP solutions in multiple mouse models (FIGS. 3E to 3H). PLGA-MPs treated B16F10 tumors showed consistently high levels of ISGs and phosphorylated TBK-1 and IRF-3 proteins 16 days after treatment, suggesting the successful activation of the STING pathway by a sequence of pulsatile releases of cGAMP. PLGA-MPs induced an immunogenic TME as demonstrated by significantly increased tumor-infiltrating CD8+ T cells, NK cells, DCs, and the shift from an M2 to an M1 macrophage phenotype (FIG. 4). An increased number of memory T cells in tumors and circulating IFNγ+CD8+ T cells was observed, which contributed to the inhibition of distant tumor growth (FIGS. 5E and 5F), reduction in metastasis (FIGS. 5H and 5I), and protective immunity against re-challenge (FIGS. 6D and 6E). Both cGAMP-MPs and 3×cGAMP-S treated mice did not completely reject tumor re-challenge. This observation is consistent with a report that repetitive intratumoral injections of STING-agonist attenuated systematic T cell responses (Sivick K E., et al., *Cell Rep.*, 25(11):3074-3085.e5 (2018)). Nonetheless, multiple doses showed a better tumor inhibition effect than a single dose of soluble STING agonist. PLGA-MPs do not exhibit apparent toxicity and could be completely degraded as supported by body weight and histology analysis, respectively. Collectively, these results demonstrated the efficacy and safety of PLGA-MPs to recapitulate multiple soluble injections.

Current STING-agonist therapies in clinical trials focus on easily accessible tumors. Intratumoral injection of therapeutics into major organs in the clinic is usually achieved under CT or ultrasound guidance (Aznar M A., et al., *J Immunol.*, 198(1):31-39. (2017)). Therefore, applying STING-agonist therapy to hard-to-reach tumors is challenging because of the complexity and high financial cost of multiple imaging-guided injections. The Examples demonstrate that cGAMP-MPs can be administered into orthotopic pancreatic tumors and effectively inhibit tumor growth and metastasis with one injection (FIGS. 6G and 6H). As such, cGAMP-MPs can not only benefit readily accessible tumors (e.g., melanoma) but also other major organ cancers. Additionally, cGAMP-MPs may be used after surgical resection of tumors that are not compatible with multiple intratumoral injections, to prevent tumor recurrence (FIGS. 6A to 6E). It is contemplated that cGAMP-MPs allow for broadening the scope of STING agonist-based therapies.

The drug loading of MPs can be increased in order to maximize the achievable number of doses within a single injection. One way to increase drug loading is to reduce microdevice wall thickness while maintaining the outer dimensions. For example, decreasing wall thickness from 100 μm to 50 μm will increase drug loading by 450%. 10 μg of cGAMP was loaded into each microdevice using microdevices with thinner walls. The dose of STING agonist in some current clinical trials is 100 μg/injection, which requires ~10 microdevices to match the same dose. The volume of 10 microdevices is $4.8 \times 10^{-4}$ cm$^3$. The overall volume of PLGA-MPs for 20 doses is $9.6 \times 10^{-3}$ cm$^3$, which is less than 1% of the volume of a 1 cm$^3$ tumor. The size and geometry of PLGA-MPs can also be optimized to increase drug loading and/or enable injections using smaller needles. The fabrication process for PLGA-MPs uses a combination of photo lithography, soft lithography, and ultralow volume dispensing technologies.

In summary, by engineering polymers such as PLGA into a compartment-shell microstructure, a fully degradable delivery system for STING agonist was developed that can improve patient adherence and lower financial costs by eliminating repeated injections and doctor visits, decrease the risk of metastasis, and lead to better effectiveness of STING agonist-based cancer immunotherapy. The PLGA-MPs expand the scope of STING agonist-based therapy to hard-to-reach tumors and as an adjuvant therapy to prevent tumor recurrence after surgery. The platform is compatible with any hydrophilic drug (e.g., pemetrexed and CpG DNA, see FIGS. 2H-2I) and even delivering different drugs at different times for synergistic cancer therapies.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising a population of microdevices, each microdevice comprising a biocompatible biodegradable polymeric shell containing therein at least one discrete compartment comprising one or more cytosolic immune receptor binding agents, wherein the one or more cytosolic immune receptor binding agents are a stimulator of interferon genes (STING) agonist, wherein the shell is made by an additive process, wherein each of the microdevices in the population has at least one external dimension between 50 micrometer (μm) and 1000 μm, wherein the population of microdevices is configured to release the one or more cytosolic immune receptor binding agents in one or more time periods, wherein when the release occurs for two or more time periods, (i) the two or more time periods are different in terms of time when release commences and (ii) the durations of the release are the same or different, in an effective amount to elicit an immune response.

2. The pharmaceutical composition of claim 1, wherein the population of microdevices is formed by three-dimensional printing, micromolding, lithography, or a combination thereof.

3. The pharmaceutical composition of claim 1, wherein the population of microdevices releases the one or more cytosolic immune receptor binding agents at multiple times or time periods.

4. The pharmaceutical composition of claim 1, wherein the one or more time periods comprise a release time period which is independently selected from about 1 day, about 4 days, about 8 days, about 11 days, about 15 days, about 18 days, about 97 days, about 1 month, about 2 months, about 3 months, about 4 months, about 5 months, about 6 months, and about 1 year.

5. The pharmaceutical composition of claim 1, wherein the biocompatible biodegradable polymeric shell comprises a polymer or co-polymer, wherein a rate of release of the one or more cytosolic immune receptor binding agents is controlled by a number-averaged molecular weight of the polymer or co-polymer in the population of microdevices, the weight-averaged molecular weight of the polymer or co-polymer, polydispersity index of the polymer or co-polymer, chain end functionality of the polymer or co-polymer, a ratio of co-polymers in the population of microdevices, a blending ratio of salts in each microdevice in the population of microdevices when present, a blending ratio of the polymer or co-polymer in the population of microdevices, a thickness of the shell, a compartment matrix, or a combination thereof.

6. The pharmaceutical composition of claim 1, wherein the STING agonist is a nucleic acid or a small molecule.

7. The pharmaceutical composition of claim 6, wherein the STING agonist is a cyclic dinucleotide or non-cyclic dinucleotide.

8. The pharmaceutical composition of claim 6, wherein the STING agonist is selected from the group consisting of cGAMP, DMXAA, MK-1454, MK-2118, E7766, MIW815 (ADU-S100), BMS-986301, GSK3745417, IMSA-101, SYNB18911, SITX-799, and SB-11285.

9. The pharmaceutical composition of claim 1, wherein the population of microdevices comprises a microdevice that is cuboidal- or cube-shaped.

10. The pharmaceutical composition of claim 1, wherein the shell and, optionally, boundaries of the one or more compartments, are formed of a biodegradable, biocompatible polymer, wherein the polymer is selected from the group consisting of polyhydroxyacids, polyhydroxyalkanoates, and polyanhydrides, and copolymers comprising one or more of these polymers.

11. The pharmaceutical composition of claim 10, wherein the polymer is poly(lactic acid), poly(glycolic acid), and/or copolymers comprising one or more of these polymers.

12. The pharmaceutical composition of claim 1, wherein the population of microdevices is formed by three-dimensional printing.

13. The pharmaceutical composition of claim 1 wherein the population of microdevices is formed by micromolding of a polymer forming the biocompatible biodegradable polymeric shell.

14. The pharmaceutical composition of claim 1 wherein the population of microdevices is formed by stereolithography of a polymer forming the biocompatible biodegradable polymeric shell.

15. The pharmaceutical composition of claim 1, wherein the composition comprises distinct populations of microdevices, wherein a first population is configured to release the one or more cytosolic immune receptor binding agents in about 4 days post administration, a second population is configured to release the one or more cytosolic immune receptor binding agents in about 8 days post administration, and a third population is configured to release the one or more cytosolic immune receptor binding agents in about 11 days post administration.

16. The pharmaceutical composition of claim 15, wherein the distinct population of microdevices comprises the same or different STING agonists.

17. The pharmaceutical composition of claim 15, wherein the composition is in a dosage for administration locally in an effective amount to induce a local or systemic immune response and/or inflammatory response in the subject.

18. The pharmaceutical composition of claim 15, wherein the composition is in a dosage comprising an effective amount to induce or increase STING pathway activity in the subject when administered locally, intratumorally, subcutaneously, intramuscularly, or peritoneally.

19. The pharmaceutical composition of claim 1, wherein the biocompatible biodegradable polymeric shell comprises a polyester.

20. The pharmaceutical composition of claim 19, wherein the population of microdevices is configured to release the one or more cytosolic immune receptor binding agents in two or more time periods.

21. A method of locally delivering one or more immune response inducing or enhancing agents to a subject at more than one time period comprising administering to the subject the pharmaceutical composition of claim 1.

22. The method of claim 21 comprising administering to the subject the pharmaceutical composition of claim 1 an effective amount to induce an immune response and/or inflammatory response at or adjacent to a tumor.

23. The method of claim 21, wherein the composition is administered intratumorally.

24. The method of claim 21, wherein the composition is administered as a single injection.

25. The method of claim 21, wherein the composition is administered in an effective amount to induce or increase an interferon response in the subject.

26. The method of claim 21, wherein the composition is administered in an effective amount to induce infiltration into the tumor microenvironment of lymphocytes, basophils, macrophages, and/or dendritic cells.

27. The method of claim 21, wherein the composition is administered in an effective amount to reduce immunosuppression within the tumor microenvironment.

28. The method of claim 21, wherein the administering to the subject the pharmaceutical composition produces a immune response, inflammatory response, induction or increase in STING pathway activity, induction or increase in a interferon response, tumor infiltration, and/or reduced immunosuppression that lasts for about 1 day to about 30 days, about 21 days to about 28 days, about 1 week to about 4 weeks, about 1 month to about 6 months, or about 6 months to about 1 year post administration.

29. The method of claim 21, wherein administration reduces or prevents tumor recurrence and/or metastasis.

30. The method of claim 21 further comprising administering an additional cancer therapy to the subject.

31. The method of claim 30, wherein the additional cancer therapy comprises surgery, radiotherapy, chemotherapy, immunotherapy, cryotherapy, or gene therapy.

32. The method of claim 31, wherein the additional therapy is immunotherapy comprising administration of one or more STING agonists, one or more immune-checkpoint blockage agents, or a combination thereof.

33. The method of claim 32, wherein the immune-checkpoint blockage agents is an antibody or antigen-binding fragment thereof.

34. The method of claim 33, wherein the antibody or antigen-binding fragment thereof is an inhibitor of CTLA-4, PD-1, PD-L1, PD-L2, TIM-3, LAG3, or a combination thereof.

35. The method of claim 21, wherein the subject has a cancer wherein the cancer is melanoma, cervical cancer, breast cancer, ovarian cancer, prostate cancer, pancreatic cancer, kidney cancer, liver cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, hepatocellular cancer, malignant mesothelioma, leukemia, lymphoma, multiple myeloma, transitional cell carcinoma, neuroblastoma, plasma cell neoplasms, Wilm's tumor, astrocytoma, ependymoma, glioma, meningioma, medulloblastoma, neuroblastoma, or hepatocellular carcinoma.

* * * * *